(12) United States Patent
Hu et al.

(10) Patent No.: US 10,604,527 B2
(45) Date of Patent: Mar. 31, 2020

(54) PYRAZINE COMPOUNDS FOR THE TREATMENT OF HEPATITIS B INFECTION

(71) Applicant: Hoffmann-La Roche Inc., Little Falls, NJ (US)

(72) Inventors: Taishan Hu, Shanghai (CN); Haixia Liu, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/196,324

(22) Filed: Nov. 20, 2018

(65) Prior Publication Data

US 2019/0185476 A1 Jun. 20, 2019

Related U.S. Application Data

(63) Continuation of application No. PCT/EP2017/061904, filed on May 18, 2017.

(30) Foreign Application Priority Data

May 20, 2016 (WO) ................ PCT/CN2016/082773

(51) Int. Cl.
 *C07D 487/04* (2006.01)
 *A61P 31/20* (2006.01)
(52) U.S. Cl.
 CPC ............ *C07D 487/04* (2013.01); *A61P 31/20* (2018.01)
(58) Field of Classification Search
 CPC .................................................. C07D 487/04
 See application file for complete search history.

(56) References Cited

FOREIGN PATENT DOCUMENTS

| EP | 3 150 600 A1 | 4/2017 |
|---|---|---|
| WO | 2009/085983 A1 | 7/2009 |
| WO | 2013/096744 A1 | 6/2013 |
| WO | 2014/033167 A1 | 3/2014 |
| WO | 2014/033170 A1 | 3/2014 |
| WO | 2014/111871 A1 | 7/2014 |
| WO | 2014/152725 A1 | 9/2014 |
| WO | 2015/180631 A1 | 12/2015 |
| WO | 2016/113273 A1 | 7/2016 |

OTHER PUBLICATIONS

Bethel et al., "Optimized scale up of 3-pyrimidinylpyrazolo[1,5-a]pyridine via Suzuki coupling; a general method of accessing a range of 3-(hetero)arylpyrazolo[1,5-a]pyridines" Tetrahedron 68:5434-5444 (2012).
ISR and Wiitten Opinion for PCT/EP2017/061904 (dated Jul. 5, 2017).
Padiya et al., "Unprecedented "In Water" Imidazole Carbonylation: Paradigm Shift for Preparation of Urea and Carbamate" Org. Lett 14(11):2814-2817 (2012).

*Primary Examiner* — Bruck Kifle
(74) *Attorney, Agent, or Firm* — Genentech, Inc.; Richard G. A. Bone

(57) ABSTRACT

The present invention relates to compounds of the formula (I),

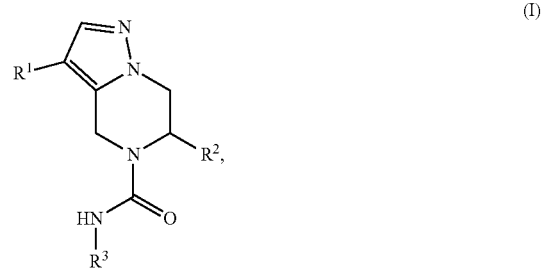

or pharmaceutically acceptable salts, enantiomer or diastereomer thereof, wherein $R^1$ to $R^3$ are as described above. The compounds may be useful for the treatment or prophylaxis of hepatitis B virus infection.

15 Claims, No Drawings

PYRAZINE COMPOUNDS FOR THE TREATMENT OF HEPATITIS B INFECTION

RELATED APPLICATIONS

This application is a continuation of International Application No. PCT/EP2017/061904, filed May 18, 2017, which claims priority to Application No. PCT/CN2016/082773, filed May 20, 2016, each of which are incorporated herein by reference in its entirety.

The present invention relates to organic compounds useful for therapy and/or prophylaxis in a mammal, and in particular for treating hepatitis B virus infection, and their pharmaceutical activity, manufacture, pharmaceutical compositions containing them and their potential use as medicaments.

FIELD OF THE INVENTION

The present invention relates to compounds of the formula (I),

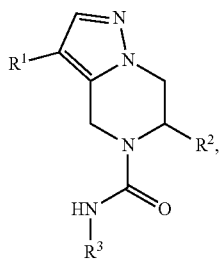

(I)

or pharmaceutically acceptable salt, enantiomer or diastereomer thereof, wherein $R^1$ to $R^3$ are as described below. The compounds of this invention are useful for the treatment or prophylaxis of hepatitis B virus infection.

Hepatitis B virus (HBV) infection is a major public health problem worldwide, roughly 30% of the world's population show serological evidence of current or past infection. Despite the introduction of a safe and effective prophylactic vaccine against the virus in the early 1980s, it is estimated that there are still more than 240 million chronic HBV carriers worldwide, a high percentage of whom will eventually develop liver cirrhosis or hepatocellular carcinoma (HCC) (WHO Hepatitis B. Fact Sheet No 204). In the 2010 Global Burden of Disease study (R Lozano, et al. Lancet, 380 (2012), 2095-2128), HBV infection ranked in the top health priorities in the world, and was the tenth leading cause of death (780,000 deaths per year). Recent studies have shown that progression to liver cirrhosis and HCC in patients with chronic HBV infection is significantly associated with circulating HBV DNA levels. Thus, antiviral therapy against HBV is critical to prevent the progression to cirrhosis or development of HCC.

HBV is a small, enveloped virus that belongs to the Hepadnaviridae family. It contains a partly double-stranded DNA genome with approximately 3200 base pairs. HBV have a strong preference for infecting human hepatocytes. The life cycle begins when HBV attaches to the host cell membrane via its envelope proteins. The precise mechanism of viral entry has not been fully elucidated. The viral relaxed circular DNA (rcDNA) containing nucleocapsids are released into the cytoplasm and transported to the nucleus. In the nucleus, the rcDNA is repaired by both viral and cellular enzymes to form covalently closed circular DNA (cccDNA). There is evidence that each infected cell contains 1-50 cccDNA molecules as unique episomal minichromosomes. Both subgenomic RNA (sgRNA) and pregenomic RNA (pgRNA) are transcribed from the cccDNA using the cellular transcriptional machinery. After nuclear export, the pgRNA is translated into the core protein and the viral polymerase. The sgRNA is translated into the regulatory X protein and the three envelope proteins. Self-assembly of the RNA-containing viral nucleocapsid takes place via complex formation of the pgRNA with the core protein and the polymerase. Inside the nucleocapsid, the pgRNA is reverse transcribed into negative-strand DNA. rcDNA is then generated by plus-strand synthesis from the negative-strand DNA. The nucleocapsids are either re-imported to the nucleus for cccDNA amplification or enveloped and released via the endoplasmic reticulum (ER). The reverse transcriptase lacks proofreading activity; thus, mutations of the viral genome are frequent and result in the coexistence of genetically distinct viral species in infected individuals (quasispecies).

Currently, seven treatments are approved for chronic hepatitis B (CHB), including two formulations of interferon (IFN) (conventional IFN and PEG-IFN) and five nucleos(t)ide analogues (NUCs: lamivudine, adefovir dipivoxil, entecavir, telbivudine, and tenofovir disoproxil). The main difference between immunomodulatory agents and NUCs is that PEG-IFN has the advantage of a finite duration of use, whereas the use of NUCs is indefinite. The major drawback of PEG-IFN is its high frequency of adverse events. Some viral genotypes do not show good responses to interferon therapy. Long-term use of NUCs, on the other hand, poses the risk of drug resistance. The ultimate goal of antiviral therapy for CHB is to prevent progression to cirrhosis or HCC via eradication of HBV or persistent viral suppression. The majority of currently treated patients fail to achieve this goal. As indicated above, nucleocapsid assembly is a critical step for HBV genome replication. As the synthesis of viral DNA takes place exclusively within the nucleocapsid, the assembly and disassembly of nucleocapsid must be precisely regulated to ensure correct packaging and release of the viral genome. Nucleocapsid assembly is an evolutionary constraint process that limits the diversity of HBV, and it is highly sensitive to even subtle molecular disturbances. Both assembly and disassembly of nucleocapsid make the process an attractive therapeutic target for the development of new antiviral therapies against various HBV genotypes and drug resistance isolates. A few capsid related anti-HBV compounds have been reported. For example, heteroaryldihydropyrimidines (HAP), including compounds named Bay 41-4109, Bay 38-7690 and Bay 39-5493 (Deres K. et al. Science 2003, 893), and phenylpropenamide derivatives such as AT-61 and AT-130 (Feld J. et al. Antiviral Research 2007, 168-177). Capsid has become a promising drug target with several molecules under clinical stage. There is still a need to develop new treatments for the prophylaxis and treatment of hepatitis B virus infection.

SUMMARY OF THE INVENTION

The present invention relates to novel compounds of formula (I),

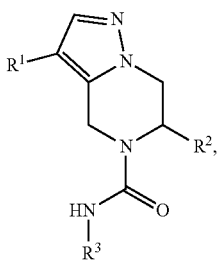

wherein
R[1] is —OR[4], wherein R[4] is $C_{1-6}$alkyl, $C_{3-7}$cycloalkyl, tetrahydrofuranyl, tetrahydropyranyl, oxopyrrolidinyl, $C_{1-6}$alkylsulfonylpiperidinyl, pyridinyl, halopyridinyl or pyrimidinyl;
—$SO_2R^5$, wherein R[5] is $C_{1-6}$alkyl, $C_{3-7}$cycloalkyl, hydroxy$C_{3-7}$cycloalkyl, $C_{1-6}$alkylamino, ($C_{1-6}$alkyl)$_2$amino, hydroxy$C_{1-6}$alkylamino, tetrahydrofuranylamino, pyrrolidinyl, halopyrrolidinyl, hydroxypyrrolidinyl, morpholinyl, haloazetidinyl, tetrahydrofuranyl or tetrahydropyranyl; or
—NR[6]R[7], wherein R[6] and R[7] are independently selected from H, $C_{1-6}$alkyl, $C_{1-6}$alkylcarbonyl, $C_{3-7}$cycloalkylcarbonyl, benzyloxycarbonyl, $C_{1-6}$alkoxy$C_{1-6}$alkylsulfonyl, $C_{1-6}$alkylsulfonyl and $C_{3-7}$cycloalkylsulfonyl;
R[2] is H or $C_{1-6}$alkyl;
R[3] is phenyl, said phenyl is unsubstituted or substituted once, twice or three times by halogen; or
pyridinyl, said pyridinyl is unsubstituted or substituted by halogen or halo$C_{1-6}$alkyl; or pharmaceutically acceptable salt, enantiomer or diastereomer thereof.

Objects of the present invention are novel compounds of formula (I), their manufacture, medicaments based on a compound in accordance with the invention and their production as well as the use of compounds of formula (I) as HBV inhibitors and for the treatment or prophylaxis of HBV infection.

DETAILED DESCRIPTION OF THE INVENTION

Definitions

The term "$C_{1-6}$alkyl" denotes a monovalent linear or branched saturated hydrocarbon group of 1 to 6 carbon atoms. In particular embodiments, $C_{1-6}$alkyl has 1 to 6 carbon atoms, and in more particular embodiments 1 to 4 carbon atoms. Examples of $C_{1-6}$alkyl include methyl, ethyl, propyl, isopropyl, n-butyl, iso-butyl, sec-butyl or tert-butyl.

The term "halo" or "halogen" are used interchangeably herein and denote fluoro, chloro, bromo or iodo.

The term "halo$C_{1-6}$alkyl" denotes a $C_{1-6}$alkyl group wherein at least one of the hydrogen atoms of the $C_{1-6}$alkyl group has been replaced by same or different halogen atoms, particularly fluoro atoms. Examples of halo$C_{1-6}$alkyl include monofluoro-, difluoro- or trifluoro-methyl, -ethyl or -propyl, for example 3,3,3-trifluoropropyl, 2-fluoroethyl, trifluoroethyl, fluoromethyl, difluoromethyl, difluoroethyl or trifluoromethyl.

The term "halopyridinyl" denotes a pyridinyl substituted once, twice or three times by halogen. Examples of halopyridinyl include, but not limited to, bromopyridinyl, chloropyridinyl, difluoropyridinyl, fluoropyridinyl and fluorochloropyridinyl.

The term "haloazetidinyl" denotes a azetidinyl substituted once, twice or three times by halogen. Example of haloazetidinyl includes, but not limited to, difluoroazetidinyl.

The term "halopyrrolidinyl" denotes a pyrrolidinyl substituted once, twice or three times by halogen. Examples of halopyrrolidinyl include, but not limited to, difluoropyrrolidinyl.

The term "oxo" denotes a divalent oxygen atom =O.

The term "heterocyclyl" denotes a monovalent saturated or partly unsaturated mono or bicyclic ring system of 3 to 10 ring atoms, comprising 1 to 5 ring heteroatoms selected from N, O and S, the remaining ring atoms being carbon. In particular embodiments, heterocyclyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocyclyl are aziridinyl, oxiranyl, azetidinyl, oxetanyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl, and lactam include, but not limited to, oxopyrrolidinyl, oxomorpholinyl, oxooxazolidinyl and oxooxazinanyl; monocyclic saturated heterocyclyl can be further substituted by $C_{1-6}$alkyl, halogen, hydroxy, cyano and $C_{1-6}$alkylsulfonyl. Examples for substituted monocyclic saturated heterocyclyl include, but not limited to difluoroazetidinyl, difluoropyrrolidinyl, hydroxypyrrolidinyl and methylsulfonylpiperidinyl.

The term "diastereomer" denotes a stereoisomer with two or more centers of chirality and whose molecules are not mirror images of one another. Diastereomers have different physical properties, e.g. melting points, boiling points, spectral properties, activities and reactivities.

The term "enantiomers" denotes two stereoisomers of a compound which are non-superimposable mirror images of one another.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethylamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Compounds of the general formula (I) which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitor of HBV

The present invention provides (i) novel compounds having the general formula (I),

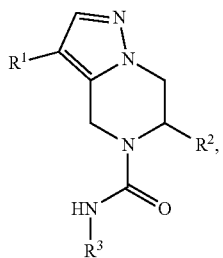

(I)

wherein
$R^1$ is —$OR^4$, wherein $R^4$ is $C_{1-6}$alkyl, $C_{3-7}$cycloalkyl, tetrahydrofuranyl, tetrahydropyranyl, oxopyrrolidinyl, $C_{1-6}$alkylsulfonylpiperidinyl, pyridinyl, halopyridinyl or pyrimidinyl;
—$SO_2R^5$, wherein $R^5$ is $C_{1-6}$alkyl, $C_{3-7}$cycloalkyl, hydroxy$C_{3-7}$cycloalkyl, $C_{1-6}$alkylamino, ($C_{1-6}$alkyl)$_2$amino, hydroxy$C_{1-6}$alkylamino, tetrahydrofuranylamino, pyrrolidinyl, halopyrrolidinyl, hydroxypyrrolidinyl, morpholinyl, haloazetidinyl, tetrahydrofuranyl or tetrahydropyranyl; or
—$NR^6R^7$, wherein $R^6$ and $R^7$ are independently selected from H, $C_{1-6}$alkyl, $C_{1-6}$alkylcarbonyl, $C_{3-7}$cycloalkylcarbonyl, benzyloxycarbonyl, $C_{1-6}$alkoxy$C_{1-6}$alkylsulfonyl, $C_{1-6}$alkylsulfonyl and $C_{3-7}$cycloalkylsulfonyl;
$R^2$ is H or $C_{1-6}$alkyl;
$R^3$ is phenyl, said phenyl is unsubstituted or substituted once, twice or three times by halogen; or
pyridinyl, said pyridinyl is unsubstituted or substituted by halogen or halo$C_{1-6}$alkyl; or pharmaceutically acceptable salt, enantiomer or diastereomer thereof.

A further embodiment of the present invention is (ii) a compound of formula (I), wherein
$R^1$ is isopropoxy, cyclopentoxy, tetrahydrofuranyloxy, tetrahydropyranyloxy, oxopyrrolidinyloxy, methylsulfonylpiperidinyloxy, pyridinyloxy, fluoropyridinyloxy, pyrimidinyloxy, cyclopentylsulfonyl, cyclopropylsulfonyl, difluoroazetidinylsulfonyl, difluoropyrrolidinylsulfonyl, dimethylaminosulfonyl, hydroxycyclopentylsulfonyl, hydroxydimethylethylaminosulfonyl, hydroxypyrrolidinylsulfonyl, isobutylsulfonyl, isopropylsulfonyl, isopropylaminosulfonyl, morpholinylsulfonyl, pyrrolidinylsulfonyl, tetrahydrofuranylsulfonyl, tetrahydrofuranylaminosulfonyl, tetrahydropyranylsulfonyl, acetylamino, acetyl(methyl)amino, cyclopentylcarbonylamino, benzyloxycarbonyl(methyl)amino, methoxyethylsulfonyl(methyl)amino, ethylsulfonyl(methyl)amino or cyclopropylsulfonyl(methyl)amino;
$R^2$ is H or methyl;
$R^3$ is fluorochlorophenyl, trifluorophenyl, chloropyridinyl or difluoromethylpyridinyl; or pharmaceutically acceptable salt, enantiomer or diastereomer thereof.

Another embodiment of the present invention is (iii) a compound of formula (I), wherein
$R^1$ is —$OR^4$, wherein $R^4$ is $C_{1-6}$alkyl, $C_{3-7}$cycloalkyl, tetrahydrofuranyl, tetrahydropyranyl, oxopyrrolidinyl, $C_{1-6}$alkylsulfonylpiperidyl, pyridinyl, halopyridinyl or pyrimidinyl;
$R^2$ is $C_{1-6}$alkyl;
$R^3$ is phenyl, said phenyl is unsubstituted or substituted once, twice or three times by halogen;
or pharmaceutically acceptable salt, enantiomer or diastereomer thereof.

A further embodiment of the present invention is (iv) a compound of formula (I), wherein
$R^1$ is isopropoxy, cyclopentoxy, tetrahydrofuranyloxy, tetrahydropyranyloxy, oxopyrrolidinyloxy, methylsulfonylpiperidinyloxy, pyridinyloxy, fluoropyridinyloxy or pyrimidinyloxy;
$R^2$ is methyl;
$R^3$ is fluorochlorophenyl or trifluorophenyl;
or pharmaceutically acceptable salt, enantiomer or diastereomer thereof.

In another embodiment of the present invention, particular compounds of the present invention are (v) selected from:
N-(3-chloro-4-fluoro-phenyl)-3-isopropoxy-6-methyl-6,7-dihydro-4H-pyrazolo[1,5-a]pyrazine-5-carboxamide;
N-(3-chloro-4-fluoro-phenyl)-3-(cyclopentoxy)-6-methyl-6,7-dihydro-4H-pyrazolo[1,5-a]pyrazine-5-carboxamide;
(6S)-N-(3-chloro-4-fluoro-phenyl)-6-methyl-3-tetrahydrofuran-3-yloxy-6,7-dihydro-4H-pyrazolo[1,5-a]pyrazine-5-carboxamide;
(6S)-N-(3-chloro-4-fluoro-phenyl)-6-methyl-3-tetrahydropyran-4-yloxy-6,7-dihydro-4H-pyrazolo[1,5-a]pyrazine-5-carboxamide;
(6S)-N-(3-chloro-4-fluoro-phenyl)-6-methyl-3-(2-oxopyrrolidin-3-yl)oxy-6,7-dihydro-4H-pyrazolo[1,5-a]pyrazine-5-carboxamide;
(6S)-N-(3-chloro-4-fluoro-phenyl)-6-methyl-3-[(1-methylsulfonyl-4-piperidyl)oxy]-6,7-dihydro-4H-pyrazolo[1,5-a]pyrazine-5-carboxamide;
(6S)-6-methyl-3-(2-pyridyloxy)-N-(3,4,5-trifluorophenyl)-6,7-dihydro-4H-pyrazolo[1,5-a]pyrazine-5-carboxamide;
(6S)-6-methyl-3-pyrimidin-2-yloxy-N-(3,4,5-trifluorophenyl)-6,7-dihydro-4H-pyrazolo[1,5-a]pyrazine-5-carboxamide; and
(6S)-3-[(5-fluoro-2-pyridyl)oxy]-6-methyl-N-(3,4,5-trifluorophenyl)-6,7-dihydro-4H-pyrazolo[1,5-a]pyrazine-5-carboxamide;
or pharmaceutically acceptable salt, enantiomer or diastereomer thereof.

Another embodiment of the present invention is (vi) a compound of formula (I), wherein
$R^1$ is —$SO_2R^5$, wherein $R^5$ is $C_{1-6}$alkyl, $C_{3-7}$cycloalkyl, hydroxy$C_{3-7}$cycloalkyl, $C_{1-6}$alkylamino, ($C_{1-6}$alkyl)$_2$amino, hydroxy$C_{1-6}$alkylamino, tetrahydrofuranylamino, pyrrolidinyl, halopyrrolidinyl, hydroxypyrrolidinyl, morpholinyl, haloazetidinyl, tetrahydrofuranyl or tetrahydropyranyl;

$R^2$ is $C_{1-6}$alkyl;

$R^3$ is phenyl, said phenyl is unsubstituted or substituted once, twice or three times by halogen; or pyridinyl, said pyridinyl is unsubstituted or substituted by halogen or halo$C_{1-6}$alkyl;

or pharmaceutically acceptable salt, enantiomer or diastereomer thereof.

A further embodiment of the present invention is (vii) a compound of formula (I), wherein $R^1$ is cyclopentylsulfonyl, cyclopropylsulfonyl, difluoroazetidinylsulfonyl, difluoropyrrolidinylsulfonyl, dimethylaminosulfonyl, hydroxycyclopentylsulfonyl, hydroxydimethylethylaminosulfonyl, hydroxypyrrolidinylsulfonyl, isobutylsulfonyl, isopropylsulfonyl, isopropylaminosulfonyl, morpholinylsulfonyl, pyrrolidinylsulfonyl, tetrahydrofuranylsulfonyl, tetrahydrofuranylaminosulfonyl or tetrahydropyranylsulfonyl;

$R^2$ is methyl;

$R^3$ is fluorochlorophenyl, trifluorophenyl, chloropyridinyl or difluoromethylpyridinyl;

or pharmaceutically acceptable salt, enantiomer or diastereomer thereof.

In another embodiment of the present invention, particular compounds of the present invention are (viii) selected from:

N-(3-chloro-4-fluoro-phenyl)-6-methyl-3-tetrahydrofuran-3-ylsulfonyl-6,7-dihydro-4H-pyrazolo[1,5-a]pyrazine-5-carboxamide;

N-(3-chloro-4-fluoro-phenyl)-3-cyclopentylsulfonyl-6-methyl-6,7-dihydro-4H-pyrazolo[1,5-a]pyrazine-5-carboxamide;

N-(3-chloro-4-fluoro-phenyl)-3-isopropylsulfonyl-6-methyl-6,7-dihydro-4H-pyrazolo[1,5-a]pyrazine-5-carboxamide;

N-(3-chloro-4-fluoro-phenyl)-3-isobutylsulfonyl-6-methyl-6,7-dihydro-4H-pyrazolo[1,5-a]pyrazine-5-carboxamide;

(6S)-N-(3-chloro-4-fluoro-phenyl)-6-methyl-3-tetrahydrofuran-3-ylsulfonyl-6,7-dihydro-4H-pyrazolo[1,5-a]pyrazine-5-carboxamide;

(6S)-N-(3-chloro-4-fluoro-phenyl)-6-methyl-3-tetrahydropyran-4-ylsulfonyl-6,7-dihydro-4H-pyrazolo[1,5-a]pyrazine-5-carboxamide;

(6S)-6-methyl-3-tetrahydrofuran-3-ylsulfonyl-N-(3,4,5-trifluorophenyl)-6,7-dihydro-4H-pyrazolo[1,5-a]pyrazine-5-carboxamide;

(6S)-N-(2-chloro-4-pyridyl)-6-methyl-3-tetrahydrofuran-3-ylsulfonyl-6,7-dihydro-4H-pyrazolo[1,5-a]pyrazine-5-carboxamide;

(6S)-N-(2-chloro-4-pyridyl)-3-isopropylsulfonyl-6-methyl-6,7-dihydro-4H-pyrazolo[1,5-a]pyrazine-5-carboxamide;

(6S)-N-(2-chloro-4-pyridyl)-3-cyclopentylsulfonyl-6-methyl-6,7-dihydro-4H-pyrazolo[1,5-a]pyrazine-5-carboxamide;

(6S)-3-isopropylsulfonyl-6-methyl-N-(3,4,5-trifluorophenyl)-6,7-dihydro-4H-pyrazolo[1,5-a]pyrazine-5-carboxamide;

(6S)-N-[2-(difluoromethyl)-4-pyridyl]-3-isopropylsulfonyl-6-methyl-6,7-dihydro-4H-pyrazolo[1,5-a]pyrazine-5-carboxamide;

(6S)-3-cyclopropylsulfonyl-6-methyl-N-(3,4,5-trifluorophenyl)-6,7-dihydro-4H-pyrazolo[1,5-a]pyrazine-5-carboxamide;

(6S)-N-(3-chloro-4-fluoro-phenyl)-6-methyl-3-pyrrolidin-1-ylsulfonyl-6,7-dihydro-4H-pyrazolo[1,5-a]pyrazine-5-carboxamide;

(6S)-N-(3-chloro-4-fluoro-phenyl)-3-(dimethylsulfamoyl)-6-methyl-6,7-dihydro-4H-pyrazolo[1,5-a]pyrazine-5-carboxamide;

(6S)-N-(3-chloro-4-fluoro-phenyl)-3-(isopropylsulfamoyl)-6-methyl-6,7-dihydro-4H-pyrazolo[1,5-a]pyrazine-5-carboxamide;

(6S)-N-(3-chloro-4-fluoro-phenyl)-6-methyl-3-[[(3S)-tetrahydrofuran-3-yl]sulfamoyl]-6,7-dihydro-4H-pyrazolo[1,5-a]pyrazine-5-carboxamide;

(6S)-3-[(2-hydroxy-1,1-dimethyl-ethyl)sulfamoyl]-6-methyl-N-(3,4,5-trifluorophenyl)-6,7-dihydro-4H-pyrazolo[1,5-a]pyrazine-5-carboxamide;

(6S)-3-(3,3-difluoropyrrolidin-1-yl)sulfonyl-6-methyl-N-(3,4,5-trifluorophenyl)-6,7-dihydro-4H-pyrazolo[1,5-a]pyrazine-5-carboxamide;

(6S)-3-[(3R)-3-hydroxypyrrolidin-1-yl]sulfonyl-6-methyl-N-(3,4,5-trifluorophenyl)-6,7-dihydro-4H-pyrazolo[1,5-a]pyrazine-5-carboxamide;

(6S)-6-methyl-3-[[(3R)-tetrahydrofuran-3-yl]sulfamoyl]-N-(3,4,5-trifluorophenyl)-6,7-dihydro-4H-pyrazolo[1,5-a]pyrazine-5-carboxamide;

(6S)-3-(3,3-difluoroazetidin-1-yl)sulfonyl-6-methyl-N-(3,4,5-trifluorophenyl)-6,7-dihydro-4H-pyrazolo[1,5-a]pyrazine-5-carboxamide;

(6S)-6-methyl-3-morpholinosulfonyl-N-(3,4,5-trifluorophenyl)-6,7-dihydro-4H-pyrazolo[1,5-a]pyrazine-5-carboxamide;

(6S)-3-[(3S)-3-hydroxypyrrolidin-1-yl]sulfonyl-6-methyl-N-(3,4,5-trifluorophenyl)-6,7-dihydro-4H-pyrazolo[1,5-a]pyrazine-5-carboxamide; and (6S)-3-(3-hydroxycyclopentyl)sulfonyl-6-methyl-N-(3,4,5-trifluorophenyl)-6,7-dihydro-4H-pyrazolo[1,5-a]pyrazine-5-carboxamide;

or pharmaceutically acceptable salt, enantiomer or diastereomer thereof.

Another embodiment of the present invention is (ix) a compound of formula (I), wherein $R^1$ is —$NR^6R^7$, wherein $R^6$ and $R^7$ are independently selected from H, $C_{1-6}$alkyl, $C_{1-6}$alkylcarbonyl, $C_{3-7}$cycloalkylcarbonyl, benzyloxycarbonyl, $C_{1-6}$alkoxy$C_{1-6}$alkylsulfonyl, $C_{1-6}$alkylsulfonyl and $C_{3-7}$cycloalkylsulfonyl;

$R^2$ is H or $C_{1-6}$alkyl;

$R^3$ is phenyl, said phenyl is unsubstituted or substituted once, twice or three times by halogen;

or pharmaceutically acceptable salt, enantiomer or diastereomer thereof.

A further embodiment of the present invention is (x) a compound of formula (I), wherein $R^1$ is acetylamino, acetyl(methyl)amino, cyclopentylcarbonylamino, benzyloxycarbonyl(methyl)amino, methoxyethylsulfonyl(methyl)amino, ethylsulfonyl(methyl)amino or cyclopropylsulfonyl(methyl)amino;

$R^2$ is H or methyl;

$R^3$ is fluorochlorophenyl or trifluorophenyl;

or pharmaceutically acceptable salt, enantiomer or diastereomer thereof.

In another embodiment of the present invention, particular compounds of the present invention are (xi) selected from:

3-acetamido-N-(3-chloro-4-fluoro-phenyl)-6,7-dihydro-4H-pyrazolo[1,5-a]pyrazine-5-carboxamide;

N-(3-chloro-4-fluoro-phenyl)-3-(cyclopentanecarbonylamino)-6,7-dihydro-4H-pyrazolo[1,5-a]pyrazine-5-carboxamide;

benzyl N-methyl-N-[(6S)-6-methyl-5-[(3,4,5-trifluorophenyl)carbamoyl]-6,7-dihydro-4H-pyrazolo[1,5-a]pyrazin-3-yl]carbamate;

(6S)-3-[acetyl(methyl)amino]-6-methyl-N-(3,4,5-trifluorophenyl)-6,7-dihydro-4H-pyrazolo[1,5-a]pyrazine-5-carboxamide;

(6S)-3-[2-methoxyethylsulfonyl(methyl)amino]-6-methyl-N-(3,4,5-trifluorophenyl)-6,7-dihydro-4H-pyrazolo[1,5-a]pyrazine-5-carboxamide;

(6S)-3-[ethylsulfonyl(methyl)amino]-6-methyl-N-(3,4,5-trifluorophenyl)-6,7-dihydro-4H-pyrazolo[1,5-a]pyrazine-5-carboxamide; and (6S)-3-[cyclopropylsulfonyl(methyl)amino]-6-methyl-N-(3,4,5-trifluorophenyl)-6,7-dihydro-4H-pyrazolo[1,5-a]pyrazine-5-carboxamide;

or pharmaceutically acceptable salt, enantiomer or diastereomer thereof.

Synthesis

The compounds of the present invention can be prepared by any conventional means. Suitable processes for synthesizing these compounds as well as their starting materials are provided in the schemes below and in the examples. All substituents, in particular, $R^1$ to $R^7$ are as defined above unless otherwise indicated. Furthermore, and unless explicitly otherwise stated, all reactions, reaction conditions, abbreviations and symbols have the meanings well known to a person of ordinary skill in organic chemistry.

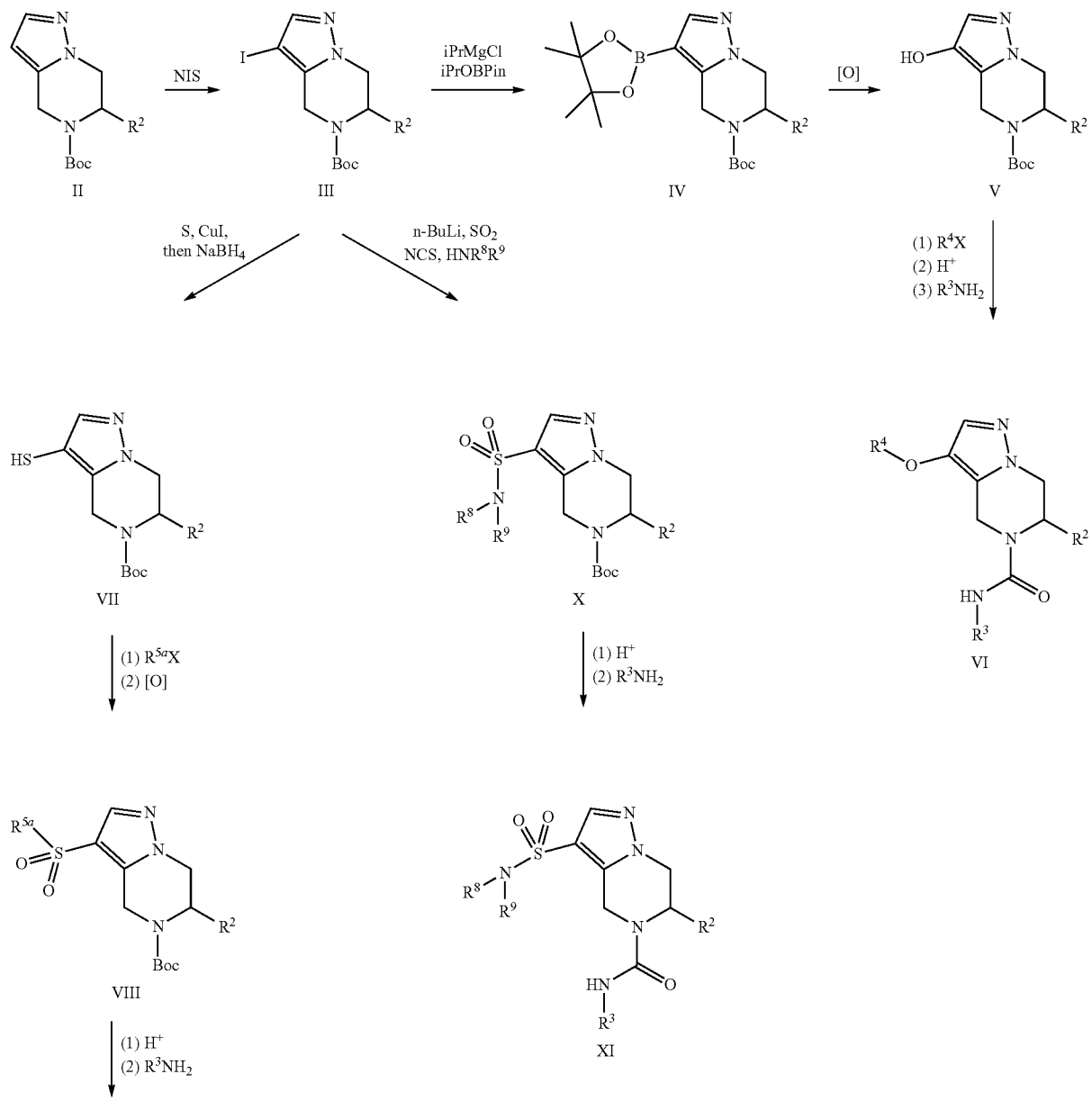

Scheme 1:

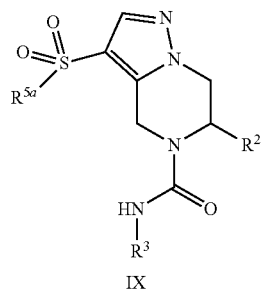

IX $R^{5a}$ is $C_{1-6}$alkyl, $C_{3-7}$cycloalkyl, hydroxy$C_{3-7}$cycloalkyl, tetrahydrofuranyl or tetrahydropyranyl. $R^8$ and $R^9$ are independently selected from H, $C_{1-6}$alkyl, tetrahydrofuranyl and hydroxy$C_{1-6}$alkyl, or $R^8$ and $R^9$ together with the nitrogen atom they are attached to form a 3-7 membered heterocyclyl, such as, but not limited to, azetidinyl, pyrrolidinyl and morpholinyl which can be further substituted with hydroxy or halogen once or twice. X is halogen.

As depicted in Scheme 1, the synthesis of compounds of the present invention started from bicyclic compound II, which was treated with iodinating reagents, such as N-iodosuccinimide, to give iodide III. Boronic acid pinacol ester IV was prepared according to a known procedure (Bethel, P. A. et al. *Tetrahedron* 2012, 68, 5434) by reacting iodide III with Grignard reagent, such as iPrMgCl, and boronic ester, such as iPrOBPin. Intermediate V was prepared from the oxidation of boronic acid pinacol ester IV with an oxidizing reagent, such as mCPBA. Intermediate V was alkylated with alkyl halide $R^4X$ in a basic condition, such as NaH or t-BuOK, and deprotected in an acidic condition such as HCl/EtOAc or TFA/DCM, followed by urea formation with amine $R^3NH_2$ in the presence of a phosgene equivalent, such as triphosgene and carbonyldiimidazole, then afforded final compound VI. In the aforementioned urea formation reaction, a suitable isocyanate or phenyl carbamate was also applied (Padiya, K. J. et al. *Org Lett.* 2012, 14, 2814 and references cited therein). On the other hand, copper catalyzed coupling reaction of iodide III with sulfur to afford a disulfide intermediate which was reduced with reducing reagent, such as $NBH_4$ to give intermediate VII. Intermediate VII was alkylated with alkyl halide $R^{5a}X$, followed by oxidation by an oxidizing reagent, such as mCPBA, to give intermediate VIII, which was then converted into final compound IX by Boc-deprotection and then employing suitable urea formation methods mentioned above. Moreover, treatment of iodide III with base such as n-BuLi to form an organometallic species, followed by reaction with $SO_2$ and NCS to give a sulfonyl chloride intermediate which was then condensed with amine $HNR^8R^9$ to afford intermediate X. Intermediate X was converted into final compound XI by employing suitable urea formation methods mentioned above.

Scheme 2:

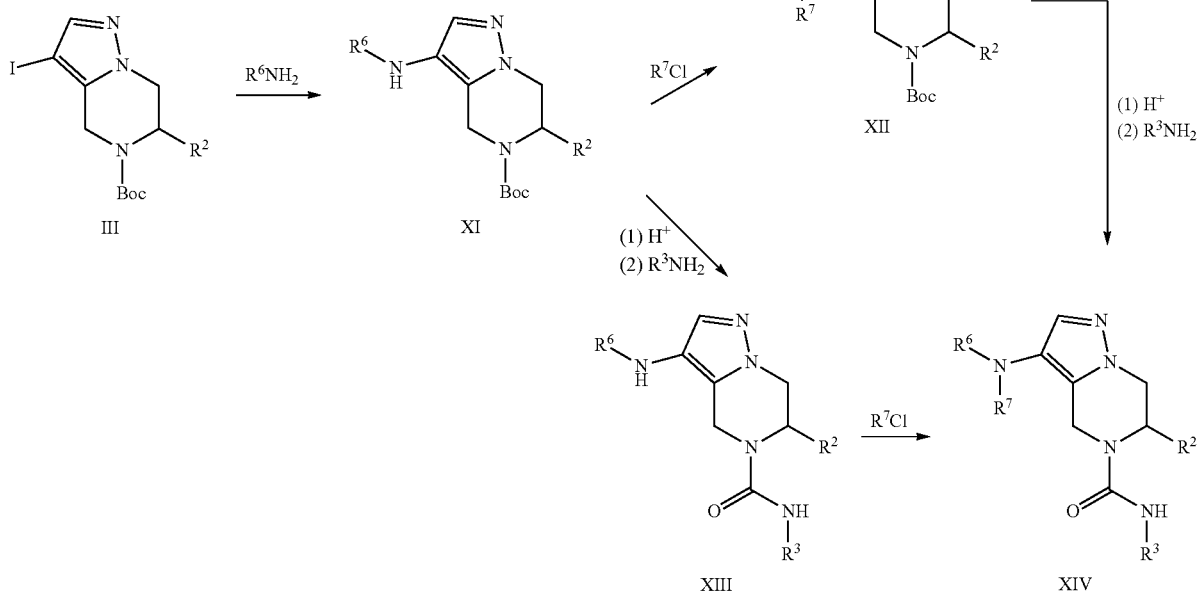

The synthesis of final compounds XIII and XIV was depicted in Scheme 2. Copper catalyzed coupling reaction of iodide III with amine or amide R⁶NH₂ afforded intermediate XI, which was converted into final compound XIII by employing suitable urea formation methods mentioned above. When R⁶NH₂ was amine, compound XIII was further converted into final compound XIV by condensation with acyl chloride or sulfonyl chloride R⁷Cl. Alternatively, when R⁶NH₂ was amine, intermediate XI first reacted with acyl chloride or sulfonyl chloride R⁷Cl to give intermediate XII, which was then converted to the final compound XIV by employing suitable urea formation methods mentioned above.

This invention also relates to a process for the preparation of a compound of formula (I) comprising the reaction of:

(a) the reaction of a compound of formula (V),

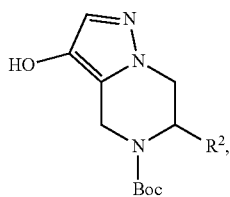

(V)

with an alkyl halide R⁴X and an acid followed by urea formation with amine R³NH₂ in the presence of a phosgene equivalent;

(b) the reaction of a compound of formula (VIII),

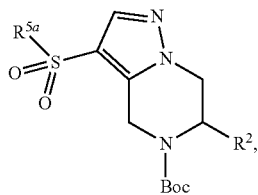

(VIII)

with an acid followed by urea formation with amine R³NH₂ in the presence of a phosgene equivalent;

(c) the reaction of a compound of formula (IX),

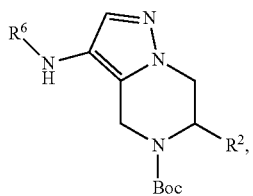

(IX)

with an acid followed by urea formation with amine R³NH₂ in the presence of a phosgene equivalent;

(d) the reaction of a compound of formula (X),

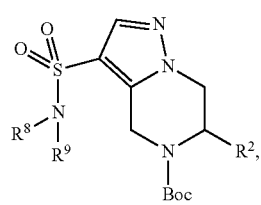

(X)

with an acid followed by urea formation with amine R³NH₂ in the presence of a phosgene equivalent;

(e) the reaction of a compound of formula XII),

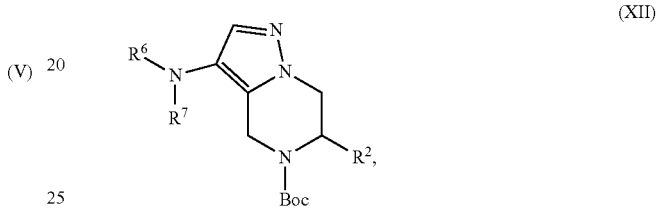

(XII)

with an acid followed by urea formation with amine R³NH₂ in the presence of a phosgene equivalent;

(f) the reaction of a compound of formula (XIII),

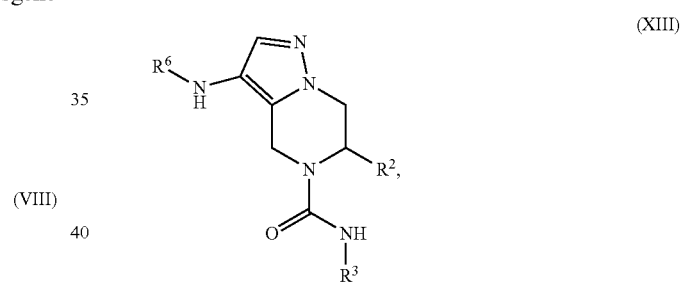

(XIII)

with an acyl chloride or sulfonyl chloride R⁷Cl;

wherein R¹ to R⁷ are defined above; R⁵ᵃ is $C_{1-6}$alkyl, $C_{3-7}$cycloalkyl, hydroxy$C_{3-7}$cycloalkyl, tetrahydrofuranyl or tetrahydropyranyl; R⁸ and R⁹ are independently selected from H, $C_{1-6}$alkyl, tetrahydrofuranyl and hydroxy$C_{1-6}$alkyl, or R⁸ and R⁹ together with the nitrogen atom they are attached to form a 3-7 membered heterocyclyl, such as, but not limited to, azetidinyl, pyrrolidinyl and morpholinyl which can be further substituted with hydroxy or halogen once or twice; X is halogen.

In step (a), alkyl halide R⁴X can be, for example, 2-iodopropane.

In step (a), (b), (c), (d) and (e), the acid can be, for example, HCl in EtOAc and TFA in DCM; phosgene equivalent can be, for example, triphosgene and carbonyldiimidazole.

In step (f), the acyl chloride or sulfonyl chloride R⁷Cl can be, for example, cyclopentanecarbonyl chloride and 2-methoxyethanesulfonyl chloride.

A compound of formula (I) when manufactured according to the above process is also an object of the invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to the suppression of serum HBV DNA levels, or HBeAg seroconversion to HBeAb, or HBsAg loss, or normalization of alanine aminotransferase levels and improvement in liver histology. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 mg to 1000 mg of the compound of the invention compounded with about 30 mg to 90 mg anhydrous lactose, about 5 mg to 40 mg sodium croscarmellose, about 5 mg to 30 mg polyvinylpyrrolidone (PVP) K30, and about 1 mg to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 mg to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I), or a stereoisomer or pharmaceutically acceptable salt thereof. In a further embodiment includes a pharmaceutical composition comprising a compound of formula (I), or a stereoisomer or pharmaceutically acceptable salt thereof, together with a pharmaceutically acceptable carrier or excipient.

Indications and Methods of Treatment

The compounds of the invention can inhibit HBV's DNA synthesis and reduce HBV DNA levels. Accordingly, the compounds of the invention are useful for the treatment or prophylaxis of HBV infection.

The invention relates to the use of a compound of formula (I) for the treatment or prophylaxis of HBV infection.

The use of a compound of formula (I) for the preparation of medicaments useful in the treatment or prophylaxis diseases that are related to HBV infection is an object of the invention.

The invention relates in particular to the use of a compound of formula (I) for the preparation of a medicament for the treatment or prophylaxis of HBV infection.

Another embodiment includes a method for the treatment or prophylaxis of HBV infection which method comprises administering an effective amount of a compound of formula (I), a stereoisomer, tautomer, prodrug or pharmaceutically acceptable salt thereof.

EXAMPLES

The invention will be more fully understood by reference to the following examples. They should not, however, be construed as limiting the scope of the invention.

Abbreviations used herein are as follows:
DIPEA: N,N-diisopropylethylamine
DCM: dichloromethane
DMAc: N,N-dimethylacetamide
DMAP: 4-dimethylaminopyridine
DMF: N,N-dimethylformamide
DMSO: dimethyl sulfoxide
EA or EtOAc: ethyl acetate
$EC_{50}$: half maximal effective concentration HPLC: high performance liquid chromatography
iPrOBPin: 2-isopropyl-4,4,5,5-tetramethyl-[1,3,2]dioxaborolane
LCMS liquid chromatography-mass spectrometry
mCPBA: meta-chloroperoxybenzoic acid
min(s): minute(s)
MS: mass spectrometry
MsCl: methanesulfonyl chloride
NCS: N-chlorosuccinimide
NIS: N-iodosuccinimide
PE: petroleum ether
prep-HPLC: preparative high performance liquid chromatography
prep-TLC: preparative thin layer chromatography
SFC: supercritical fluid chromatography
t-BuXPhos: 2-di-tert-butylphosphino-2',4',6'-triisopropylbiphenyl
TEA: trimethylamine
TFA: trifluoroacetic acid
THF: tetrahydrofuran
$Pd_2(dba)_3$: Tris(dibenzylideneacetone)dipalladium(0)
pgRNA: pre-genomic RNA
qPCR: quantitative polymerase chain reaction
v/v volume ratio

GENERAL EXPERIMENTAL CONDITIONS

Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C18 (5 μm, OBD™ 30×100 mm) column or SunFire™ Prep-C18 (5 μm, OBD™ 30×100 mm) column. Waters AutoP purification System (Column: XBridge™ Prep-C18, 30×100 mm, Sample Manager 2767, Pump 2525, Detector: Micromass ZQ and UV 2487, solvent system: acetonitrile and 0.1% ammonium hydroxide in water). For SFC chiral separation, intermediates were separated by chiral column (Daicel chiralpak IC, 5 μm, 30×250 mm) using Mettler Toledo SFC-Multigram III system, solvent system: 95% $CO_2$ and 5% IPA (0.5% TEA in IPA), back pressure 100 bar, detection UV@ 254 nm.

LC/MS spectra of compounds were obtained using a LC/MS (Waters™ Alliance 2795-Micromass ZQ), LC/MS conditions were as follows (running time 6 mins):

Acidic condition: A: 0.1% formic acid in $H_2O$; B: 0.1% formic acid in acetonitrile;

Basic condition: A: 0.1% $NH_3$—$H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(MH)^+$.

NMR Spectra were obtained using Bruker Avance 400 MHz.

The microwave assisted reactions were carried out in a Biotage Initiator Sixty microwave synthesizer.

All reactions involving air-sensitive reagents were performed under an argon atmosphere. Reagents were used as received from commercial suppliers without further purification unless otherwise noted.

The following examples are intended to illustrate the meaning of the present invention but should by no means represent a limitation within the meaning of the present invention:

Preparative Examples

The invention will be more fully understood by reference to the following examples. They should not, however, be construed as limiting the scope of the invention.

Example 1

N-(3-chloro-4-fluoro-phenyl)-3-isopropoxy-6-methyl-6,7-dihydro-4H-pyrazolo[1,5-a]pyrazine-5-carboxamide

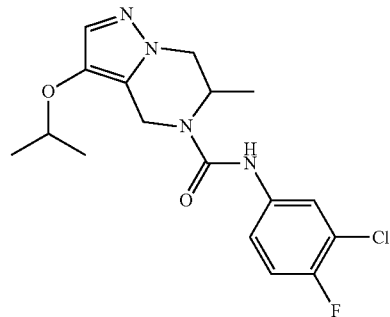 [SMILES: CC(C)Oc1cnn2c1CN(C(=O)Nc1ccc(F)c(Cl)c1)C(C)C2]

The title compound was prepared according to the following scheme:

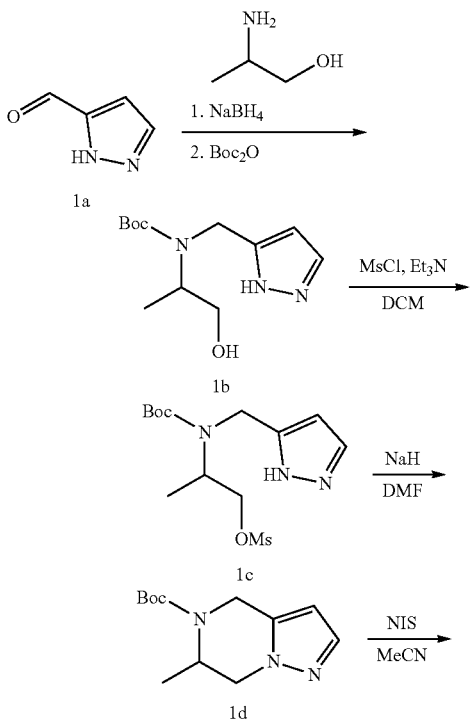

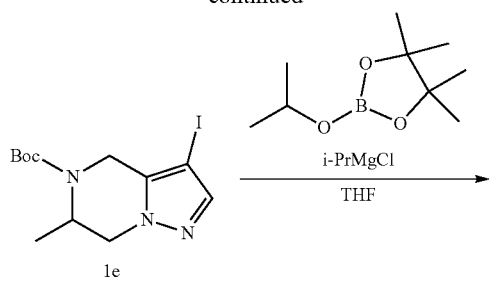

1e

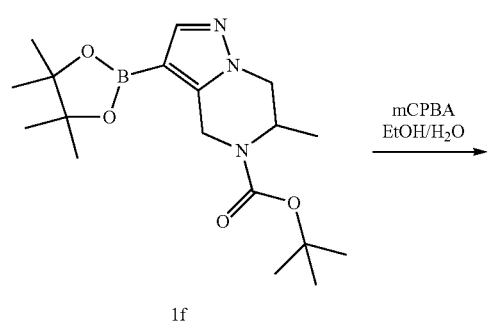

1f

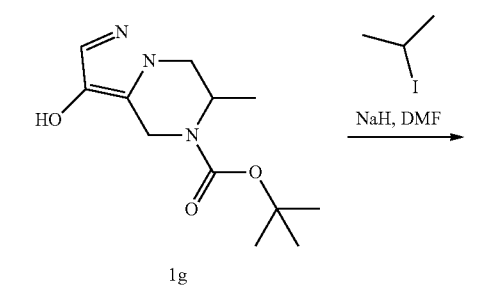

1g

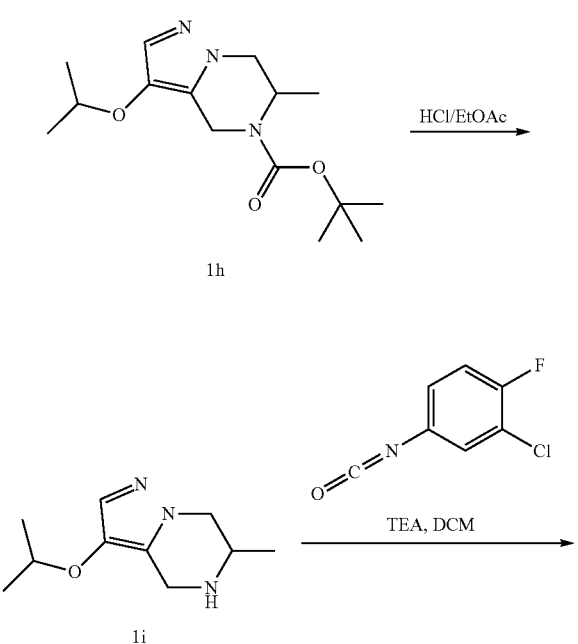

1h

1i

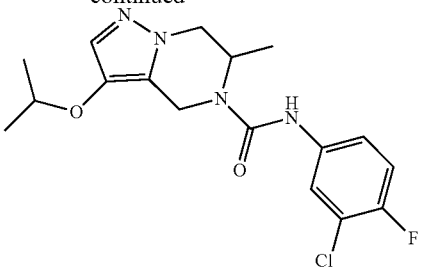

1

Step 1: Preparation of tert-butyl N-(2-hydroxy-1-methyl-ethyl)-N-(1H-pyrazol-5-ylmethyl)carbamate (compound 1b)

To a solution of 1H-pyrazole-5-carbaldehyde (compound 1a, 54.0 g, 562.5 mmol) in MeOH (300 mL) was added 2-aminopropan-1-ol (41.2 g, 675.0 mmol) and the reaction mixture was stirred at room temperature for 1 hour. NaBH$_4$ (25.9 g, 675.0 mmol) was added at 0° C. and the reaction mixture was stirred for another hour followed by addition of H$_2$O (300 mL) and Boc$_2$O (147.1 g, 675.0 mmol). The resulting mixture was then stirred at room temperature for another 12 hours, and extracted with EtOAc (600 mL). The organic layer was dried over Na$_2$SO$_4$, filtered and concentrated. The residue was purified by column chromatography (eluting with 0%~5% MeOH in DCM) to afford compound 1b (80 g) as a colorless oil. $^1$H NMR (400 MHz, CHLOROFORM-d) δ ppm 7.55-7.46 (m, 1H), 6.30-6.07 (m, 1H), 4.62-4.37 (m, 2H), 4.33-3.99 (m, 1H), 3.74-3.47 (m, 2H), 1.54-1.27 (m, 9H), 1.12 (d, J=7.0 Hz, 3H).

Step 2: Preparation of 2-[tert-butoxycarbonyl(1H-pyrazol-5-ylmethyl)amino]propyl methanesulfonate (compound 1c)

To a mixture of tert-butyl N-(2-hydroxy-1-methyl-ethyl)-N-(1H-pyrazol-5-ylmethyl)carbamate (compound 1b, 80.0 g, 117.2 mmol) and Et$_3$N (100.5 g, 995.6 mmol) in DCM (800 mL) was added MsCl (57.3 g, 497.8 mmol) slowly at 0° C. The resulting reaction mixture was stirred at room temperature for 2 hours, then washed with water (500 mL) and brine (500 mL), and dried over Na$_2$SO$_4$. The organic layer was concentrated to afford compound 1c (100 g, crude) which was used directly in next step.

Step 3: Preparation of tert-butyl 6-methyl-6,7-dihydro-4H-pyrazolo[1,5-a]pyrazine-5-carboxylate (compound 1d)

To a solution of 2-[tert-butoxycarbonyl(1H-pyrazol-5-ylmethyl)amino]propyl methanesulfonate (compound 1c, 100.0 g, 313.4 mmol) in DMF (1 L) was added NaH (15.0 g, 376.2 mmol) in portions at 0° C. The reaction mixture was then stirred at room temperature for 12 hours, poured into water (2 L) and extracted with EtOAc (1 L) twice. The combined organic layer was concentrated and the residue was purified by column chromatography (eluting with 10%~80% EtOAc in petroleum ether) to afford compound 1d (18.0 g) as a colorless oil. LCMS (M+H$^+$): 238. $^1$H NMR (400 MHz, CHLOROFORM-d) δ ppm 7.55-7.46 (m, 1H), 6.20 (s, 1H), 4.98-4.91 (m, 1H), 4.85-4.76 (m, 1H), 4.45-4.33 (m, 1H), 4.26-4.18 (m, 1H), 4.16-4.08 (m, 1H), 1.53 (s, 9H), 1.23-1.10 (m, 3H).

Step 4: Preparation of tert-butyl 3-iodo-6-methyl-6, 7-dihydro-4H-pyrazolo[1,5-a]pyrazine-5-carboxylate (compound 1e)

To a solution of tert-butyl 6-methyl-6,7-dihydro-4H-pyrazolo[1,5-a]pyrazine-5-carboxylate (compound 1d, 3.3 g, 14.8 mmol) in $CH_3CN$ (40 mL) was added NIS (5.0 g, 22.1 mmol) slowly. The reaction mixture was stirred at room temperature for 16 hours and then extracted with EtOAc (50 mL), washed with brine (50 mL). The organic layer was dried over $Na_2SO_4$ and concentrated, and the residue was purified by column chromatography (eluting with 10%~80% EtOAc in petroleum ether) to afford compound 1e (4.8 g) as a white solid.

Step 5: Preparation of tert-butyl 6-methyl-3-(4,4,5,5-tetramethyl-1,3,2-dioxaborolan-2-yl)-6,7-dihydro-4H-pyrazolo[1,5-a]pyrazine-5-carboxylate (compound 1f)

To a solution of tert-butyl 3-iodo-6-methyl-6,7-dihydro-4H-pyrazolo[1,5-a]pyrazine-5-carboxylate (compound 1e, 3.0 g, 8.26 mmol) in THF (50.0 ml) was added i-PrMgCl (12.4 mL, 24.8 mmol) at 0° C., the reaction mixture was stirred at 0° C. for 1 hour. Then to the solution was added 2-isopropoxy-4,4,5,5-tetramethyl-1,3,2-dioxaborolane (4.61 g, 24.8 mmol). The reaction mixture was stirred at room temperature for 2 hours, then quenched with sat. $NH_4Cl$ (10.0 mL), extracted with EtOAc (50 mL) three times. The combined organic layer was washed with brine, dried over $Na_2SO_4$ and concentrated to give a crude product which was purified by column chromatography (eluted with PE:EtOAc=20:1~10:1) to afford compound 1f (2.5 g) as a white solid. LCMS (M+H$^+$): 364.

Step 6: Preparation of tert-butyl 3-hydroxy-6-methyl-6,7-dihydro-4H-pyrazolo[1,5-a]pyrazine-5-carboxylate (compound 1g)

To a solution of tert-butyl 6-methyl-3-(4,4,5,5-tetramethyl-1,3,2-dioxaborolan-2-yl)-6,7-dihydro-4H-pyrazolo[1,5-a]pyrazine-5-carboxylate (compound 1f, 1.0 g, 2.75 mmol) in $H_2O$/EtOH (12 mL, v/v=½) was added mCPBA (476.9 mg, 2.75 mmol) at room temperature. The reaction mixture was stirred at room temperature for 6 hours, then quenched with aq. $Na_2SO_3$, extracted with EtOAc (50 mL) three times. The combined organic layer was washed with bine, dried over $Na_2SO_4$ and concentrated. The residue was purified by column chromatography (eluted with PE:EA=10:1-1:1) to afford compound 1g (480.0 mg) as a yellow oil. LCMS (M+H$^+$): 254.

Step 7: Preparation of tert-butyl 3-isopropoxy-6-methyl-6,7-dihydro-4H-pyrazolo[1,5-a]pyrazine-5-carboxylate (compound 1h)

To a solution of tert-butyl 3-hydroxy-6-methyl-6,7-dihydro-4H-pyrazolo[1,5-a]pyrazine-5-carboxylate (compound 1g, 150.0 mg, 0.59 mmol) and 2-iodopropane (151 mg, 0.89 mmol) in DMF (4.0 mL) was added NaH (35 mg, 0.89 mmol) at room temperature in one portion. The reaction mixture was stirred at room temperature for 3 hours, then quenched with water (5 mL) and diluted with EtOAc (60 mL). The organic layer was washed with water and brine, dried over $Na_2SO_4$ and concentrated. The residue was purified by column chromatography (eluted with PE:EtOAc=10:1-1:1) to afford compound 1h (120.0 mg) as a yellow oil. LCMS (M+H$^+$): 296.

Step 8: Preparation of 3-isopropoxy-6-methyl-4,5,6,7-tetrahydropyrazolo[1,5-a]pyrazine (compound 1i)

To a solution of tert-butyl 3-isopropoxy-6-methyl-6,7-dihydro-4H-pyrazolo[1,5-a]pyrazine-5-carboxylate (compound 1h, 120.0 mg, 0.406 mmol) in EtOAc (5.0 mL) was added HCl/EA (4 M, 5.0 mL) at room temperature. The reaction mixture was stirred for 1 hour, then concentrated to give compound 1i (100.0 mg, crude) as a white solid which was used directly in next step. LCMS (M+H$^+$): 196.

Step 9: Preparation of N-(3-chloro-4-fluoro-phenyl)-3-isopropoxy-6-methyl-6,7-dihydro-4H-pyrazolo[1,5-a]pyrazine-5-carboxamide (Example 1)

To a solution of 3-isopropoxy-6-methyl-4,5,6,7-tetrahydropyrazolo[1,5-a]pyrazine (compound 1i, 70.0 mg, 0.408 mmol) and TEA (82.4 mg, 0.816 mmol) in DCM (3.0 mL) was added 2-chloro-1-fluoro-4-isocyanato-benzene (79.7 mg, 0.408 mmol) at room temperature. The reaction mixture was stirred for 1 hour, then concentrated. The residue was purified by prep-HPLC to give Example 1 (55.0 mg) as a white solid. LCMS (M+H$^+$): 367. $^1$H NMR (400 MHz, METHANOL-d$_4$) δ ppm 7.62 (dd, J=2.6, 6.7 Hz, 1H), 7.37-7.29 (m, 2H), 7.15 (t, J=9.0 Hz, 1H), 4.93 (d, J=16.4 Hz, 1H), 4.97-4.89 (m, 1H), 4.41 (d, J=16.3 Hz, 1H), 4.31-4.18 (m, 2H), 4.06 (d, J=12.7 Hz, 1H), 1.29 (d, J=6.1 Hz, 6H), 1.19 (d, J=6.8 Hz, 3H).

Example 2

N-(3-chloro-4-fluoro-phenyl)-3-(cyclopentoxy)-6-methyl-6,7-dihydro-4H-pyrazolo[1,5-a]pyrazine-5-carboxamide

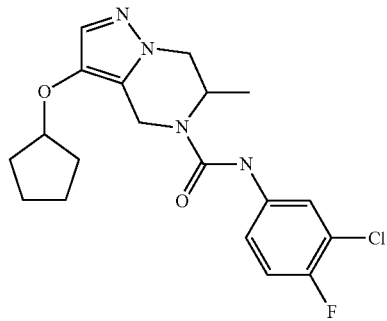 [SMILES: CC1Cn2ncc(OC3CCCC3)c2CN1C(=O)Nc1ccc(F)c(Cl)c1]

Preparation of N-(3-chloro-4-fluoro-phenyl)-3-(cyclopentoxy)-6-methyl-6,7-dihydro-4H-pyrazolo[1,5-a]pyrazine-5-carboxamide (Example 2)

The title compound was prepared in analogy to the preparation of Example 1 by using iodocyclopentane instead of 2-iodopropane. Example 2 (32 mg) was obtained as a white solid. LCMS (M+H$^+$): 393. $^1$H NMR (400 MHz, METHANOL-d$_4$) δ ppm 7.63 (dd, J=2.6, 6.7 Hz, 1H), 7.36-7.30 (m, 2H), 7.16 (t, J=9.0 Hz, 1H), 4.93 (d, J=16.4

Hz, 1H), 4.98-4.90 (m, 1H), 4.66-4.59 (m, 1H), 4.41 (d, J=16.2 Hz, 1H), 4.22 (dd, J=4.2, 12.6 Hz, 1H), 4.06 (dd, J=1.1, 12.7 Hz, 1H), 1.90-1.73 (m, 6H), 1.71-1.57 (m, 2H), 1.20 (d, J=6.8 Hz, 3H).
Example 3
(6S)-N-(3-chloro-4-fluoro-phenyl)-6-methyl-3-tetra-hydrofuran-3-yloxy-6,7-dihydro-4H-pyrazolo[1,5-a]pyrazine-5-carboxamide
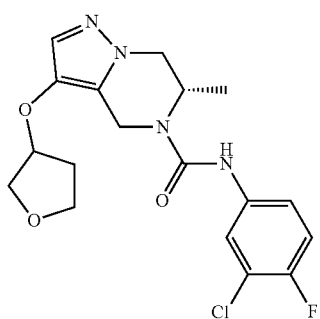 [SMILES: C[C@H]1Cn2ncc(OC3CCOC3)c2CN1C(=O)Nc1ccc(F)c(Cl)c1]
The title compound was prepared according to the following scheme:
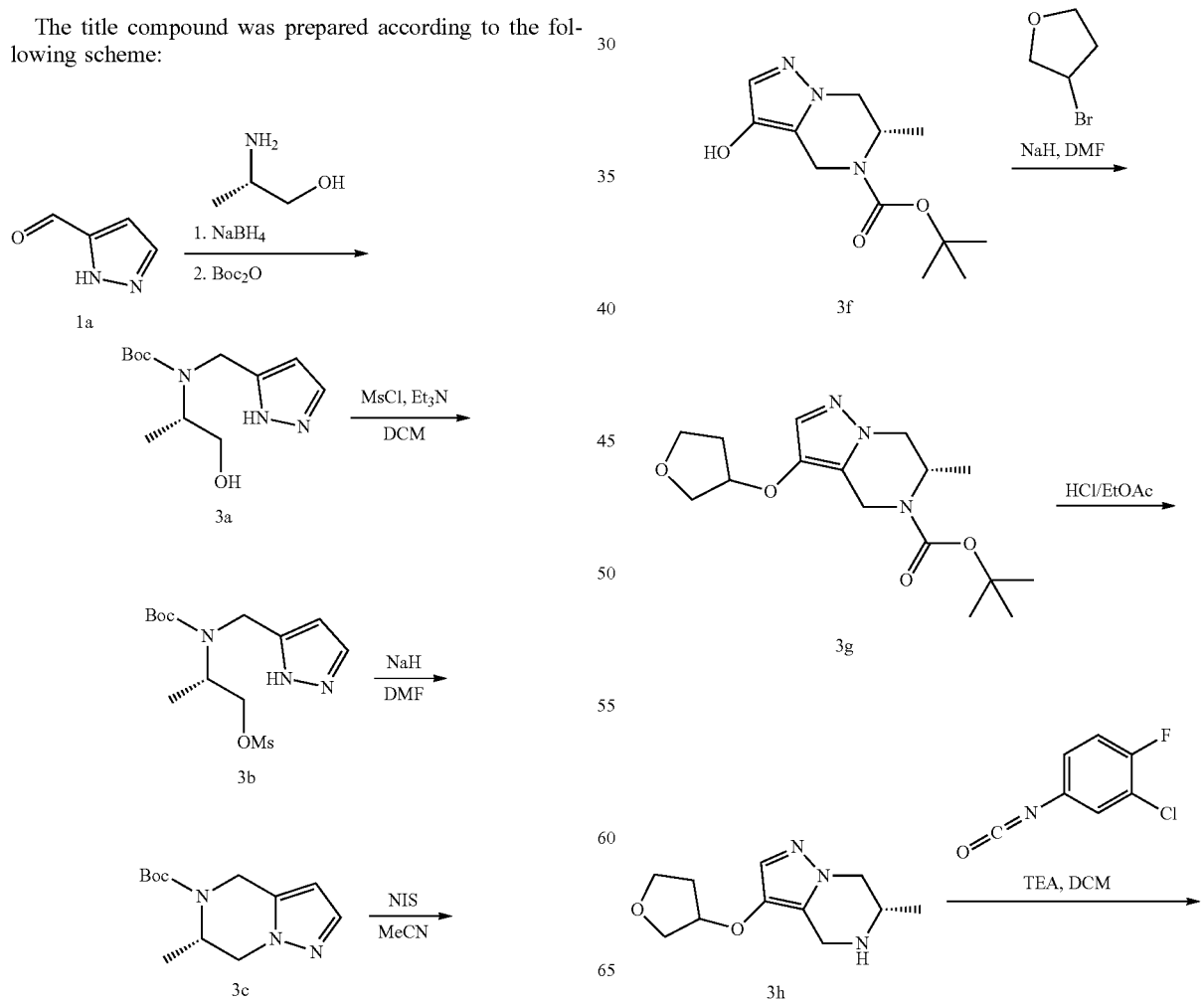

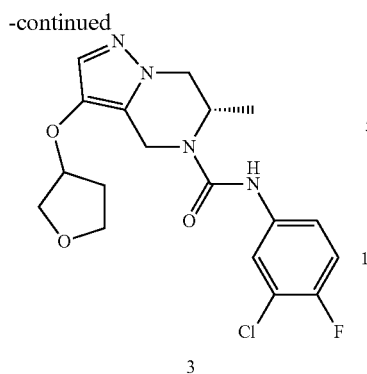

3

Preparation of tert-butyl (6S)-3-hydroxy-6-methyl-6,7-dihydro-4H-pyrazolo[1,5-a]pyrazine-5-carboxylate (compound 3f)

Compound 3f was prepared in analogy to the preparation of compound 1g by using (2S)-2-aminopropan-1-ol instead of 2-aminopropan-1-ol. Compound 3f (70 mg) was obtained as a white solid. LCMS (M+H$^+$): 254.

Preparation of tert-butyl (6S)-6-methyl-3-tetrahydrofuran-3-yloxy-6,7-dihydro-4H-pyrazolo[1,5-a]pyrazine-5-carboxylate (compound 3g)

To a solution of tert-butyl (6S)-3-hydroxy-6-methyl-6,7-dihydro-4H-pyrazolo[1,5-a]pyrazine-5-carboxylate (compound 3f, 70.0 mg, 0.277 mmol) and 3-bromotetrahedronfuran (62.7 mg, 0.415 mmol) in DMF (4.0 ml) was added NaH (16.6 mg, 0.415 mmol) at room temperature. The reaction mixture was stirred at room temperature for 3 h, then quenched with water (5.0 mL), diluted with EtOAc (60 mL). The organic layer was washed with water and brine, dried over Na$_2$SO$_4$ and concentrated. The residue was purified by column chromatography (eluted with PE:EA=10:1-1:1) to afford compound 3g (50.0 mg) as a yellow oil. LCMS (M+H$^+$): 324.

Preparation of (6S)-6-methyl-3-tetrahydrofuran-3-yloxy-4,5,6,7-tetrahydropyrazolo[1,5-a]pyrazine (compound 3h)

To a solution of tert-butyl (6S)-6-methyl-3-tetrahydrofuran-3-yloxy-6,7-dihydro-4H-pyrazolo[1,5-a]pyrazine-5-carboxylate (compound 3g, 50.0 mg, 0.155 mmol) in EtOAc (5 mL) was added HCl/EA (4 M, 5.0 mL). The reaction mixture was stirred at room temperature for 1 hour, then concentrated to give compound 3h (30.0 mg, crude) which was used directly in the next step without purification. LCMS (M+H$^+$): 224.

Preparation of (6S)-N-(3-chloro-4-fluoro-phenyl)-6-methyl-3-tetrahydrofuran-3-yloxy-6,7-dihydro-4H-pyrazolo[1,5-a]pyrazine-5-carboxamide (Example 3)

To a solution of (6S)-6-methyl-3-tetrahydrofuran-3-yloxy-4,5,6,7-tetrahydropyrazolo[1,5-a]pyrazine (compound 3h, 30.0 mg, 0.175 mmol) and TEA (35.4 mg, 0.350 mmol) in DCM (3.0 mL) was added 2-chloro-1-fluoro-4-isocyanato-benzene (39.1 mg, 0.175 mmol) at room temperature. The reaction mixture was stirred at room temperature for 1 hour, solvent was removed under reduced pressure. The residue was purified by prep-HPLC to afford Example 3 (8.0 mg) as a white solid. LCMS (M+H$^+$): 395. $^1$H NMR (400 MHz, METHANOL-d$_4$) δ ppm 7.63 (dd, J=2.6, 6.7 Hz, 1H), 7.38-7.30 (m, 2H), 7.15 (t, J=9.0 Hz, 1H), 4.99-4.91 (m, 2H), 4.83 (m, 1H), 4.42 (d, J=16.3 Hz, 0.5H), 4.41 (d, J=16.3 Hz, 0.5H), 4.22 (dd, J=4.3, 12.7 Hz, 1H), 4.07 (d, J=12.8 Hz, 1H), 4.00-3.92 (m, 2H), 3.91-3.83 (m, 2H), 2.24-2.10 (m, 2H), 1.20 (d, J=6.8 Hz, 3H).

Example 4

(6S)-N-(3-chloro-4-fluoro-phenyl)-6-methyl-3-tetrahydropyran-4-yloxy-6,7-dihydro-4H-pyrazolo[1,5-a]pyrazine-5-carboxamide

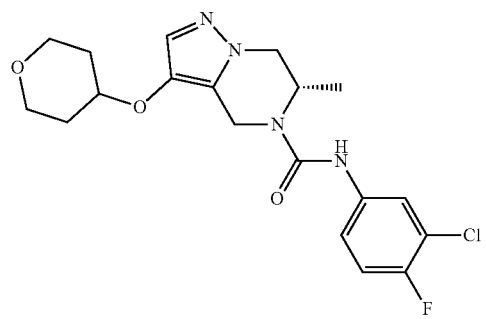 [SMILES: C[C@H]1Cn2ncc(OC3CCOCC3)c2CN1C(=O)Nc1ccc(F)c(Cl)c1]

Preparation of (6S)-N-(3-chloro-4-fluoro-phenyl)-6-methyl-3-tetrahydropyran-4-yloxy-6,7-dihydro-4H-pyrazolo[1,5-a]pyrazine-5-carboxamide (Example 4)

The title compound was prepared in analogy to the preparation of Example 3 by using 4-bromotetrahedronpyran instead of 3-bromotetrahedronfuran. Example 4 (20 mg) was obtained as a white solid. LCMS (M+H$^+$): 409. $^1$H NMR (400 MHz, DMSO-d$_6$) δ ppm 8.89 (s, 1H), 7.78 (dd, J=2.5, 6.8 Hz, 1H), 7.50-7.42 (m, 1H), 7.38 (s, 1H), 7.36-7.29 (m, 1H), 4.93 (d, J=16.3 Hz, 1H), 4.89-4.82 (m, 1H), 4.31 (d, J=16.3 Hz, 1H), 4.20-4.10 (m, 2H), 4.03 (d, J=12.5 Hz, 1H), 3.84-3.83 (m, 2H), 3.47-3.37 (m, 2H), 2.01-1.87 (m, 2H), 1.63-1.49 (m, 2H), 1.09 (d, J=6.8 Hz, 3H).

Example 5

(6S)-N-(3-chloro-4-fluoro-phenyl)-6-methyl-3-(2-oxopyrrolidin-3-yl)oxy-6,7-dihydro-4H-pyrazolo[1,5-a]pyrazine-5-carboxamide

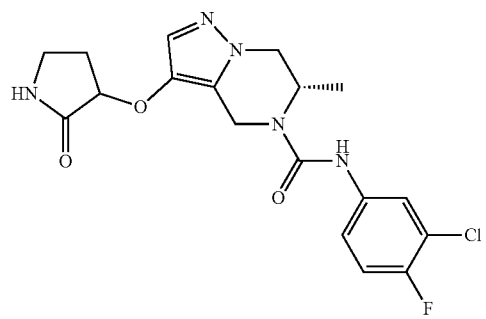 [SMILES: C[C@H]1Cn2ncc(OC3CCNC3=O)c2CN1C(=O)Nc1ccc(F)c(Cl)c1]

Preparation of (6S)-N-(3-chloro-4-fluoro-phenyl)-6-methyl-3-(2-oxopyrrolidin-3-yl)oxy-6,7-dihydro-4H-pyrazolo[1,5-a]pyrazine-5-carboxamide (Example 5)

The title compound was prepared in analogy to the preparation of Example 3 by using 3-bromopyrrolidin-2-one instead of 3-bromotetrahedronfuran. Example 5 (20 mg) was obtained as a white solid. LCMS (M+H$^+$): 408. $^1$H NMR (400 MHz, DMSO-d$_6$) δ ppm 8.92 (s, 0.5H), 8.91 (s, 0.5H), 8.05 (s, 1H), 7.78 (dd, J=2.3, 6.8 Hz, 1H), 7.50-7.43 (m, 1H), 7.39 (s, 1H), 7.32 (t, J=9.0 Hz, 1H), 4.96 (d, J=16.1 Hz, 1H), 4.87 (m, 1H), 4.65-4.55 (m, 1H), 4.33 (d, J=16.3 Hz, 1H), 4.17-4.08 (m, 1H), 4.07-4.00 (m, 1H), 3.33-3.09 (m, 2H), 2.55-2.45 (m, 1H), 2.08-1.92 (m, 1H), 1.10 (d, J=6.0 Hz, 1.5H), 1.08 (d, J=6.0 Hz, 1.5H).

Example 6

(6S)-N-(3-chloro-4-fluoro-phenyl)-6-methyl-3-[(1-methylsulfonyl-4-piperidyl)oxy]-6,7-dihydro-4H-pyrazolo[1,5-a]pyrazine-5-carboxamide

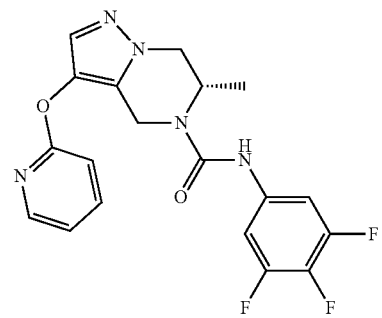 [SMILES: C[C@H]1Cn2ncc(Oc3ccccn3)c2CN1C(=O)Nc1cc(F)c(F)c(F)c1]

Preparation of (6S)-N-(3-chloro-4-fluoro-phenyl)-6-methyl-3-[(1-methylsulfonyl-4-piperidyl)oxy]-6,7-dihydro-4H-pyrazolo[1,5-a]pyrazine-5-carboxamide (Example 6)

The title compound was prepared in analogy to the preparation of Example 3 by using 4-bromo-1-methylsulfonyl-piperidine instead of 3-bromotetrahedronfuran. Example 6 (20 mg) was obtained as a white solid. LCMS (M+H$^+$): 486. $^1$H NMR (400 MHz, DMSO-d$_6$) δ ppm 8.93 (s, 1H), 7.78 (dd, J=2.5, 6.8 Hz, 1H), 7.49-7.42 (m, 1H), 7.39 (s, 1H), 7.36-7.29 (m, 1H), 4.94 (d, J=16.3 Hz, 1H), 4.87 (m, 1H), 4.31 (d, J=16.3 Hz, 1H), 4.18-4.09 (m, 2H), 4.08-3.96 (m, 1H), 3.45-3.35, (m, 2H), 3.11-3.00 (m, 2H), 2.90 (s, 3H), 1.95-2.05 (m, 2H), 1.77-1.63 (m, 2H), 1.10 (d, J=6.8 Hz, 3H).

Example 7

(6S)-6-methyl-3-(2-pyridyloxy)-N-(3,4,5-trifluoro-phenyl)-6,7-dihydro-4H-pyrazolo[1,5-a]pyrazine-5-carboxamide

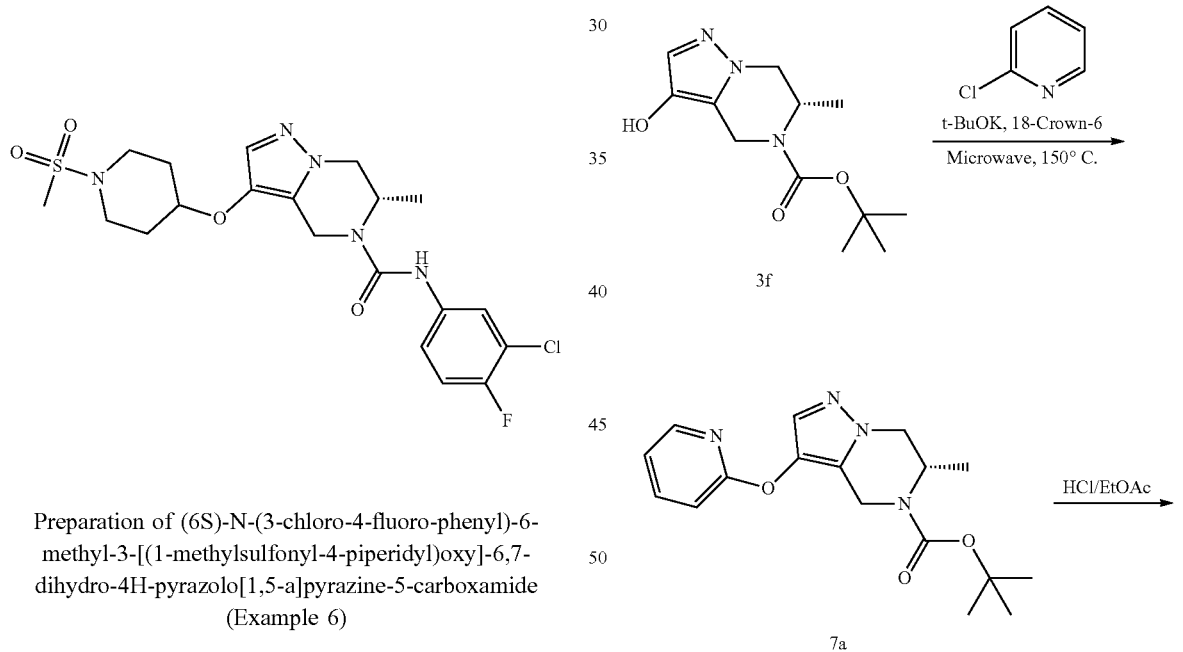

The title compound was prepared according to the following scheme:

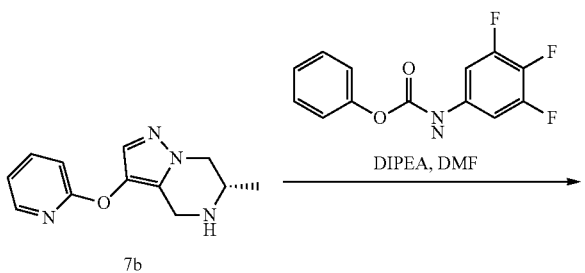

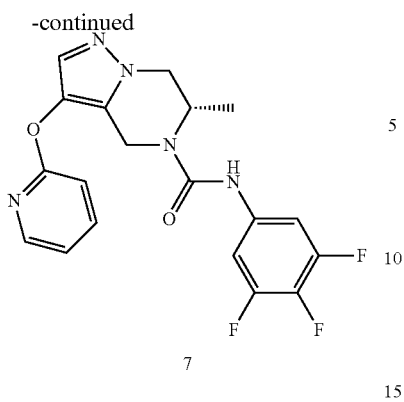

7

Step 1: Preparation of tert-butyl (6S)-6-methyl-3-(2-pyridyloxy)-6,7-dihydro-4H-pyrazolo[1,5-a]pyrazine-5-carboxylate (compound 7a)

To a solution of tert-butyl (6S)-3-hydroxy-6-methyl-6,7-dihydro-4H-pyrazolo[1,5-a]pyrazine-5-carboxylate (compound 3f, 50.0 mg, 0.2 mmol) in 2-chloropyridine (1.0 mL) and 18-crown-6 (26.4 mg, 0.1 mmol) was added t-BuOK (44.8 mg, 0.4 mmol) at room temperature. The reaction mixture was stirred at 150° C. under microwave for 30 min, then solvent was removed. The residue was purified by prep-HPLC to afford compound 7a (20.0 mg) as a yellow oil. LCMS (M+H$^+$): 331.

Step 2: Preparation of (6S)-6-methyl-3-(2-pyridyloxy)-4,5,6,7-tetrahydropyrazolo[1,5-a]pyrazine (compound 7b)

To a solution of tert-butyl (6S)-6-methyl-3-(2-pyridyloxy)-6,7-dihydro-4H-pyrazolo[1,5-a]pyrazine-5-carboxylate (compound 7a, 20.0 mg, 0.06 mmol) in EtOAc (5.0 mL) was added HCl/EtOAc (5.0 ml). The reaction mixture was stirred at room temperature for 1 hour, then solvent was removed under reduced pressure to afford compound 7b (16.1 mg, crude) as a white solid. LCMS (M+H$^+$): 231.

Step 3: Preparation of (6S)-6-methyl-3-(2-pyridyloxy)-N-(3,4,5-trifluorophenyl)-6,7-dihydro-4H-pyrazolo[1,5-a]pyrazine-5-carboxamide (Example 7)

To a solution of (6S)-6-methyl-3-(2-pyridyloxy)-4,5,6,7-tetrahydropyrazolo[1,5-a]pyrazine (compound 7b, 16.0 mg, 0.06 mmol) in DMF (2.0 mL) was added DIPEA (31.0 mg, 0.24 mmol) and phenyl N-(3,4,5-trifluorophenyl)carbamate (23.9 mg, 0.09 mmol) at room temperature. The reaction mixture was stirred at 40° C. for 2 h, then concentrated. The residue was purified by prep-HPLC to afford Example 7 (9.3 mg) as a white solid. LCMS (M+H$^+$): 404. $^1$H NMR (400 MHz, DMSO-d$_6$) δ ppm 9.21-9.11 (m, 1H), 8.17 (d, J=3.8 Hz, 1H), 7.88-7.83 (m, 1H), 7.51 (s, 1H), 7.45 (dd, J=6.5, 10.8 Hz, 2H), 7.15-7.11 (m, 1H), 7.05 (d, J=8.3 Hz, 1H), 4.98-4.89 (m, 1H), 4.89 (d, J=16.4 Hz, 1H), 4.30-4.21 (m, 2H), 4.13 (d, J=12.8 Hz, 1H), 1.16 (d, J=6.7 Hz, 3H).

Example 8

(6S)-6-methyl-3-pyrimidin-2-yloxy-N-(3,4,5-trifluorophenyl)-6,7-dihydro-4H-pyrazolo[1,5-a]pyrazine-5-carboxamide

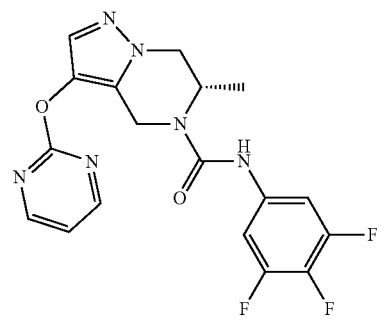 [SMILES: C[C@H]1Cn2ncc(Oc3ncccn3)c2CN1C(=O)Nc1cc(F)c(F)c(F)c1]

Preparation of (6S)-6-methyl-3-pyrimidin-2-yloxy-N-(3,4,5-trifluorophenyl)-6,7-dihydro-4H-pyrazolo[1,5-a]pyrazine-5-carboxamide (Example 8)

The title compound was prepared in analogy to the preparation of Example 3 by using 2-chloropyrimidine instead of 3-bromotetrahedronfuran. Example 8 (3.4 mg) was obtained as a white solid. LCMS (M+H$^+$): 405. $^1$H NMR (400 MHz, DMSO-d$_6$) δ ppm 9.06 (s, 1H), 8.68 (d, J=4.8 Hz, 2H), 7.56 (s, 1H), 7.44 (dd, J=6.6, 10.9 Hz, 2H), 7.30 (t, J=4.8 Hz, 1H), 5.00-4.90 (m, 1H), 4.91 (d, J=16.6 Hz, 1H), 4.33-4.20 (m, 2H), 4.12 (d, J=12.4 Hz, 1H), 1.15 (d, J=6.8 Hz, 3H).

Example 9

(6S)-3-[(5-fluoro-2-pyridyl)oxy]-6-methyl-N-(3,4,5-trifluorophenyl)-6,7-dihydro-4H-pyrazolo[1,5-a]pyrazine-5-carboxamide

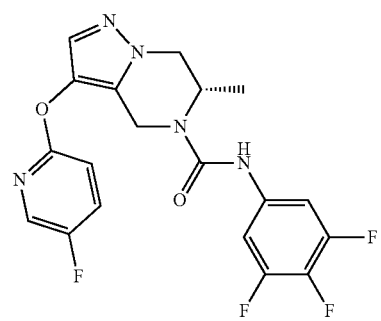 [SMILES: C[C@H]1Cn2ncc(Oc3ccc(F)cn3)c2CN1C(=O)Nc1cc(F)c(F)c(F)c1]

Preparation of (6S)-3-[(5-fluoro-2-pyridyl)oxy]-6-methyl-N-(3,4,5-trifluorophenyl)-6,7-dihydro-4H-pyrazolo[1,5-a]pyrazine-5-carboxamide (Example 9)

The title compound was prepared in analogy to the preparation of Example 3 by using 2,5-difluoropyridine instead of 3-bromotetrahedronfuran. Example 9 (10.4 mg) was obtained as a white solid. LCMS (M+H$^+$): 422. $^1$H NMR (400 MHz, DMSO-d₆) δ ppm 9.12 (s, 1H), 8.16 (d, J=3.1 Hz, 1H), 7.83 (ddd, J=3.1, 7.9, 9.0 Hz, 1H), 7.51 (s, 1H), 7.45 (dd, J=6.5, 10.8 Hz, 2H), 7.13 (dd, J=3.5, 9.0 Hz, 1H), 5.00-4.90 (m, 1H), 4.89 (d, J=16.8 Hz, 1H), 4.27 (d, J=16.8 Hz, 1H), 4.29-4.21 (m, 1H), 4.14 (d, J=12.8 Hz, 1H), 1.15 (d, J=6.8 Hz, 3H).

Example 10

N-(3-chloro-4-fluoro-phenyl)-6-methyl-3-tetrahydrofuran-3-ylsulfonyl-6,7-dihydro-4H-pyrazolo[1,5-a]pyrazine-5-carboxamide

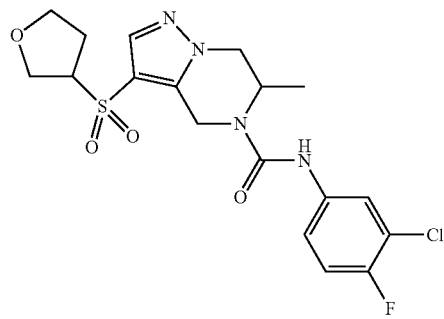 [SMILES: CC1Cn2ncc(S(=O)(=O)C3CCOC3)c2CN1C(=O)Nc1ccc(F)c(Cl)c1]

The title compound was prepared according to the following scheme:

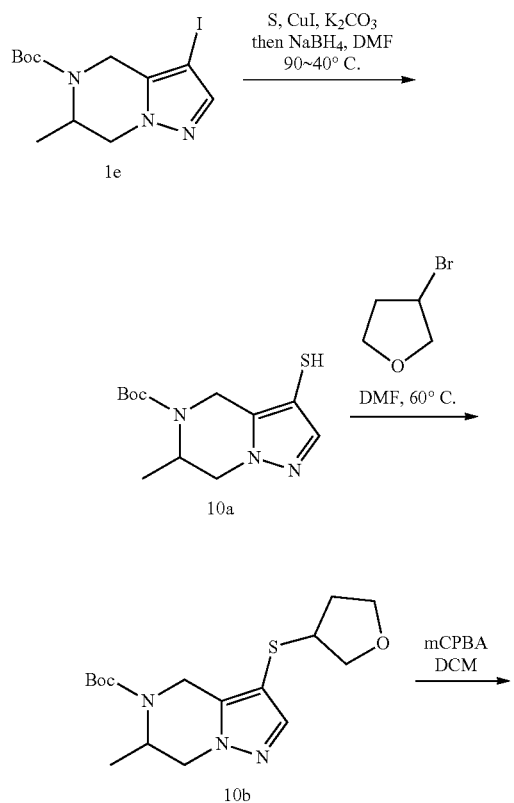

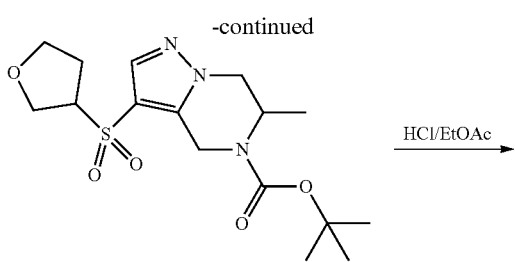

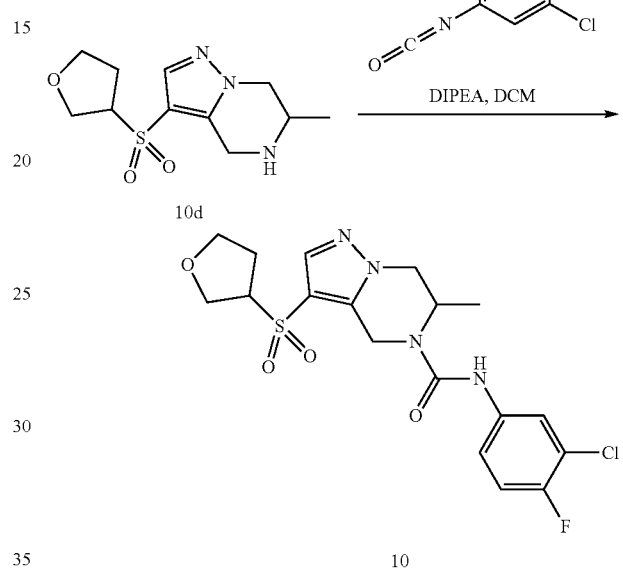

Step 1: Preparation of tert-butyl 6-methyl-3-sulfanyl-6,7-dihydro-4H-pyrazolo[1,5-a]pyrazine-5-carboxylate (compound 10a)

To a solution of tert-butyl 3-iodo-6-methyl-6,7-dihydro-4H-pyrazolo[1,5-a]pyrazine-5-carboxylate (compound 1e, 1.1 g, 3.0 mmol) in DMF (10.0 mL) was added sulfur (0.29 g, 9.0 mmol), CuI (57.0 mg, 0.3 mmol) and K₂CO₃ (0.83 g, 6.0 mmol). The reaction mixture was stirred at 90° C. for 12 hours, then cooled to 0° C. To the solution was added NaBH₄ (0.34 g, 9.0 mmol). The resulting mixture was stirred at 40° C. for 5 hours and used directly in next step.

Step 2: Preparation of tert-butyl 6-methyl-3-tetrahydrofuran-3-ylsulfanyl-6,7-dihydro-4H-pyrazolo[1,5-a]pyrazine-5-carboxylate (compound 10b)

To the crude solution of tert-butyl 6-methyl-3-sulfanyl-6,7-dihydro-4H-pyrazolo[1,5-a]pyrazine-5-carboxylate (compound 10a, 269.0 mg, 1.0 mmol) in DMF (3.0 mL) was added 3-bromotetrahedronfuran (150.0 mg, 1.0 mmol) at room temperature. After being stirred at 60° C. for 2 hours, the reaction mixture was filtered, the filtrate was purified by prep-HPLC to afford compound 10b (60.0 mg) as a colorless oil. LCMS (M+H⁺): 340.

Step 3: Preparation of tert-butyl 6-methyl-3-tetrahydrofuran-3-ylsulfonyl-6,7-dihydro-4H-pyrazolo[1,5-a]pyrazine-5-carboxylate (compound 10c)

To a solution of tert-butyl 6-methyl-3-tetrahydrofuran-3-ylsulfanyl-6,7-dihydro-4H-pyrazolo[1,5-a]pyrazine-5-carboxylate (compound 10b, 60.0 mg, 0.193 mmol) in DCM (5.0 mL) was added mCPBA (100.1 mg, 0.579 mmol) at 0° C. The mixture was stirred at room temperature for 2 hours, then quenched by addition of aq. sodium sulfite solution. The reaction mixture was extracted with DCM, dried over $Na_2SO_4$ and concentrated to afford compound 10c (60.0 mg) as a colorless oil.

Step 4: Preparation of 6-methyl-3-tetrahydrofuran-3-ylsulfonyl-4,5,6,7-tetrahydropyrazolo[1,5-a]pyrazine (compound 10d)

To a solution of tert-butyl 6-methyl-3-tetrahydrofuran-3-ylsulfonyl-6,7-dihydro-4H-pyrazolo[1,5-a]pyrazine-5-carboxylate (compound 10c, 60.0 mg, 0.163 mmol) in EtOAc (5 mL) was added HCl/EA (4 M, 5.0 mL). The reaction mixture was stirred at room temperature for 1 hour, then solvent was removed to afford compound 10d (49.7 mg, crude) as a white solid.

Step 5: Preparation of N-(3-chloro-4-fluoro-phenyl)-6-methyl-3-tetrahydrofuran-3-ylsulfonyl-6,7-dihydro-4H-pyrazolo[1,5-a]pyrazine-5-carboxamide (Example 10)

To a solution of 6-methyl-3-tetrahydrofuran-3-ylsulfonyl-4,5,6,7-tetrahydropyrazolo[1,5-a]pyrazine (compound 10d, 40.0 mg, 0.131 mmol) and DIPEA (50.7 mg, 0.393 mmol) in DCM (3.0 mL) was added 2-chloro-1-fluoro-4-isocyanato-benzene (24.7 mg, 0.144 mmol) at 0° C. The mixture was stirred at room temperature for 30 min, then solvent was removed under reduced pressure. The residue was purified by prep-HPLC to afford Example 10 (14 mg) as a white solid. LCMS (M+H$^+$): 443. $^1$H NMR (400 MHz, DMSO-d$_6$) δ ppm 9.13 (s, 1H), 8.02 (s, 1H), 7.74 (dd, J=2.4, 6.8 Hz, 1H), 7.45-7.35 (m, 1H), 7.38-7.30 (m, 1H), 5.28 (d, J=18.3 Hz, 0.5H), 5.27 (d, J=18.3 Hz, 0.5H), 4.98-4.86 (m, 1H), 4.51 (d, J=18.2 Hz, 0.5H), 4.50 (d, J=18.2 Hz, 0.5H), 4.36-4.31 (m, 1H), 4.26-4.13 (m, 2H), 4.05-3.95 (m, 1H), 3.90-3.84 (m, 1H), 3.80-3.71 (m, 1H), 3.69-3.62 (m, 1H), 2.21-2.14 (m, 2H), 1.15 (d, J=6.7 Hz, 1.5H), 1.14 (d, J=6.7 Hz, 1.5H).

Example 11

N-(3-chloro-4-fluoro-phenyl)-3-cyclopentylsulfonyl-6-methyl-6,7-dihydro-4H-pyrazolo[1,5-a]pyrazine-5-carboxamide

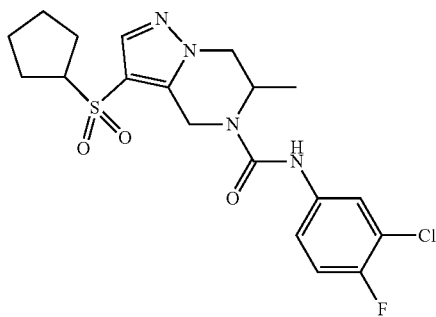 [SMILES: CC1Cn2ncc(S(=O)(=O)C3CCCC3)c2CN1C(=O)Nc1ccc(F)c(Cl)c1]

Preparation of N-(3-chloro-4-fluoro-phenyl)-3-cyclopentylsulfonyl-6-methyl-6,7-dihydro-4H-pyrazolo[1,5-a]pyrazine-5-carboxamide (Example 11)

The title compound was prepared in analogy to the preparation of Example 10 by using bromocyclopentane instead of 3-bromotetrahedronfuran. Example 11 (47 mg) was obtained as a white solid. LCMS (M+H$^+$): 441. $^1$H NMR (400 MHz, DMSO-d6) δ ppm 9.12 (s, 1H), 7.96 (s, 1H), 7.74 (dd, J=2.6, 6.8 Hz, 1H), 7.43 (ddd, J=2.6, 4.3, 9.0 Hz, 1H), 7.36-7.31 (m, 1H), 5.27 (d, J=18.3 Hz, 1H), 4.98-4.88 (m, 1H), 4.49 (d, J=18.3 Hz, 1H), 4.37-4.30 (m, 1H), 4.23 (d, J=12.8 Hz, 1H), 3.76 (quin, J=7.8 Hz, 1H), 1.90-1.83 (m, 4H), 1.68-1.52 (m, 4H), 1.15 (d, J=6.9 Hz, 3H).

Example 12

N-(3-chloro-4-fluoro-phenyl)-3-isopropylsulfonyl-6-methyl-6,7-dihydro-4H-pyrazolo[1,5-a]pyrazine-5-carboxamide

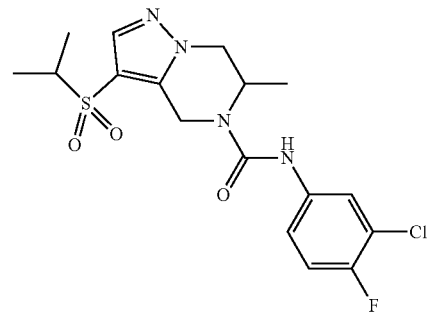 [SMILES: CC1Cn2ncc(S(=O)(=O)C(C)C)c2CN1C(=O)Nc1ccc(F)c(Cl)c1]

Preparation of N-(3-chloro-4-fluoro-phenyl)-3-isopropylsulfonyl-6-methyl-6,7-dihydro-4H-pyrazolo[1,5-a]pyrazine-5-carboxamide (Example 12)

The title compound was prepared in analogy to the preparation of Example 10 by using 2-bromopropane instead of 3-bromotetrahedronfuran. Example 12 (50 mg) was obtained as a white solid. LCMS (M+H$^+$): 415. $^1$H NMR (400 MHz, DMSO-d$_6$) δ ppm 9.12 (s, 1H), 7.92 (s, 1H), 7.74 (dd, J=2.6, 6.8 Hz, 1H), 7.45-7.40 (m, 1H), 7.37-7.30 (m, 1H), 5.25 (d, J=18.3 Hz, 1H), 4.94-4.86 (m, 1H), 4.46 (d, J=18.3 Hz, 1H), 4.34 (dd, J=4.4, 12.8 Hz, 1H), 4.23 (d, J=12.8 Hz, 1H), 3.36 (quin, J=6.8 Hz, 1H), 1.21 (d, J=6.8 Hz, 6H), 1.15 (d, J=6.8 Hz, 3H).

Example 13

N-(3-chloro-4-fluoro-phenyl)-3-isobutylsulfonyl-6-methyl-6,7-dihydro-4H-pyrazolo[1,5-a]pyrazine-5-carboxamide

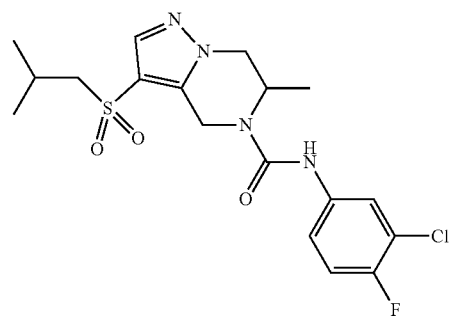 [SMILES: CC(C)CS(=O)(=O)c1cnn2c1CN(C(=O)Nc1ccc(F)c(Cl)c1)C(C)C2]

Preparation of N-(3-chloro-4-fluoro-phenyl)-3-isobutylsulfonyl-6-methyl-6,7-dihydro-4H-pyrazolo[1,5-a]pyrazine-5-carboxamide (Example 13)

The title compound was prepared in analogy to the preparation of Example 10 by using 1-bromo-2-methyl-propane instead of 3-bromotetrahedronfuran. Example 13 (34 mg) was obtained as a white solid. LCMS (M+H$^+$): 429. $^1$H NMR (400 MHz, DMSO-d$_6$) δ ppm 9.13 (s, 1H), 7.95 (s, 1H), 7.74 (dd, J=2.5, 6.9 Hz, 1H), 7.43 (ddd, J=2.6, 4.3, 9.0 Hz, 1H), 7.37-7.31 (m, 1H), 5.27 (d, J=18.3 Hz, 1H), 4.94-4.86 (m, 1H), 4.51 (d, J=18.3 Hz, 1H), 4.36-4.29 (m, 1H), 4.25-4.20 (m, 1H), 3.23 (dd, J=2.9, 6.3 Hz, 2H), 2.14-2.00 (m, 1H), 1.15 (d, J=6.9 Hz, 3H), 1.01 (d, J=2.6 Hz, 3H), 0.99 (d, J=2.6 Hz, 3H).

Example 14

(6S)-N-(3-chloro-4-fluoro-phenyl)-6-methyl-3-tetrahydrofuran-3-ylsulfonyl-6,7-dihydro-4H-pyrazolo[1,5-a]pyrazine-5-carboxamide The title compound was prepared according to the following scheme:

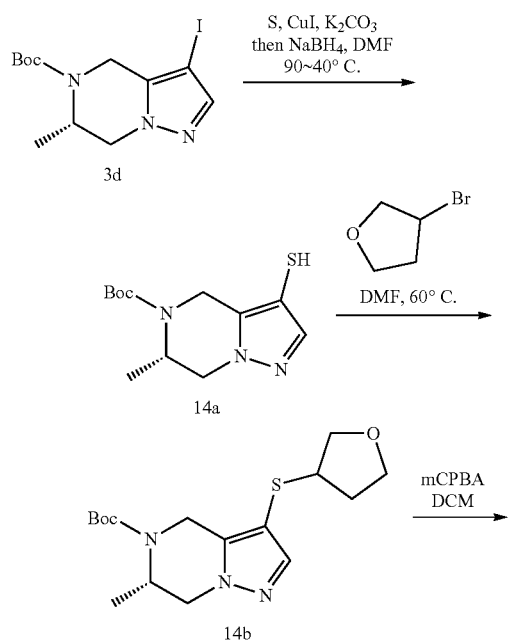

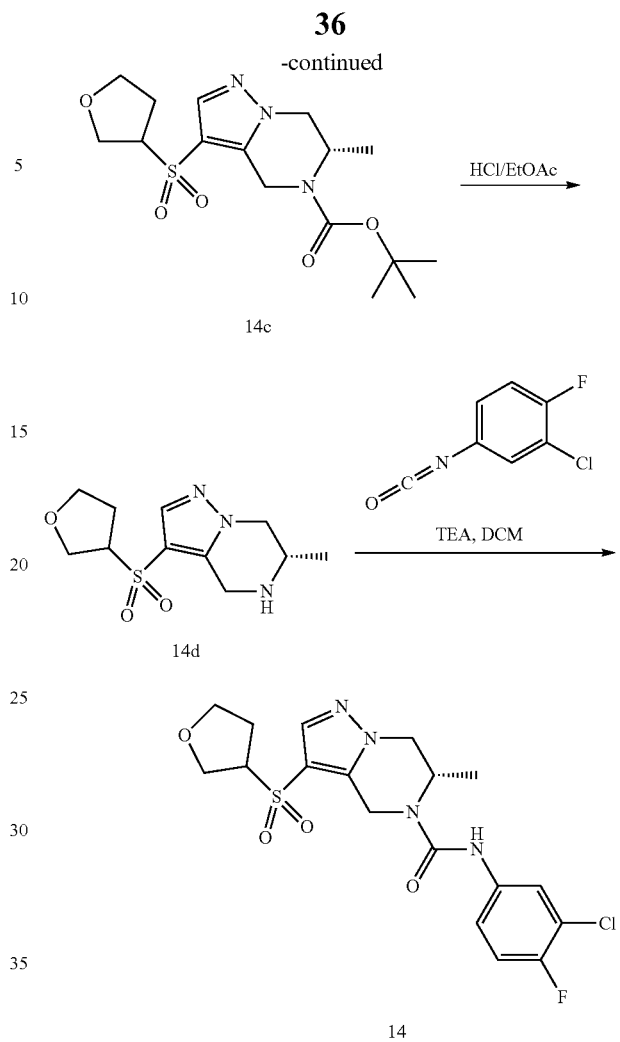

Step 1: Preparation of tert-butyl (6S)-6-methyl-3-sulfanyl-6,7-dihydro-4H-pyrazolo[1,5-a]pyrazine-5-carboxylate (compound 14a)

To a solution of tert-butyl (6S)-3-iodo-6-methyl-6,7-dihydro-4H-pyrazolo[1,5-a]pyrazine-5-carboxylate (compound 3d, 1.5 g, 4.13 mmol) in DMF (15.0 mL) was added S (0.4 g, 12.4 mmol), CuI (77.83 mg, 0.41 mmol) and K$_2$CO$_3$ (1.14 g, 8.26 mmol) at room temperature. The reaction mixture was stirred at 90° C. for 12 hours until starting material was consumed. NaBH$_4$ (0.47 g, 12.4 mmol) was added at 0° C. The resulting mixture was then stirred at 40° C. for 12 hours. Compound 14a was detected by LCMS. The reaction mixture was stored under N$_2$ and used directly in next step. LCMS (M+H$^+$): 270.

Step 2: Preparation of tert-butyl (6S)-6-methyl-3-tetrahydrofuran-3-ylsulfanyl-6,7-dihydro-4H-pyrazolo[1,5-a]pyrazine-5-carboxylate (compound 14b)

To a solution of tert-butyl (6S)-6-methyl-3-sulfanyl-6,7-dihydro-4H-pyrazolo[1,5-a]pyrazine-5-carboxylate (compound 14a, 900.0 mg, 3.34 mmol) in DMF (30.0 mL) was added 3-bromotertahedronfuran (504.5 mg, 3.34 mmol) at room temperature. The reaction mixture was stirred for at 60° C. for 12 hours, then cooled to room temperature, quenched by water (30.0 mL), and extracted with DCM (30.0 mL) three times. The combine organic layer was washed with water and brine, dried over anhydrous sodium sulfate and concentrated. The residue was purified by prep-HPLC to give compound 14b (0.3 g) as a yellow oil. LCMS (M+H$^+$): 340.

Step 3: Preparation of tert-butyl (6S)-6-methyl-3-tetrahydrofuran-3-ylsulfonyl-6,7-dihydro-4H-pyrazolo[1,5-a]pyrazine-5-carboxylate (compound 14c)

To a solution of tert-butyl (6S)-6-methyl-3-tetrahydrofuran-3-ylsulfanyl-6,7-dihydro-4H-pyrazolo[1,5-a]pyrazine-5-carboxylate (compound 14b, 300.0 mg, 0.88 mmol) in DCM (10.0 mL) was added mCPBA (455.6 mg, 2.64 mmol) at 0° C. The reaction mixture was stirred for 5 hours at room temperature. LCMS showed the starting material was consumed. Sodium sulfite solution (5.0 mL) was added and the mixture was extracted with DCM (30.0 mL) twice. The combined organic layer was washed with brine, dried with Na$_2$SO$_4$ and concentrated to afford crude compound 14c (200.0 mg) as a colorless oil. LCMS (M+H$^+$):372.

Step 4: Preparation of (6S)-6-methyl-3-tetrahydrofuran-3-ylsulfonyl-4,5,6,7-tetrahydropyrazolo[1,5-a]pyrazine (compound 14d)

To a solution of tert-butyl (6S)-6-methyl-3-tetrahydrofuran-3-ylsulfonyl-6,7-dihydro-4H-pyrazolo[1,5-a]pyrazine-5-carboxylate (compound 14c, 200.0 mg, 0.54 mmol) in EtOAc (10.0 mL) was added HCl/EtOAc (4 M, 10.0 mL). The reaction mixture was stirred at room temperature for 3 hours, then solvent was removed to give crude compound 14d (150.0 mg, crude) as a white solid which was used directly in next step.

Step 5: Preparation of (6S)-N-(3-chloro-4-fluoro-phenyl)-6-methyl-3-tetrahydrofuran-3-ylsulfonyl-6,7-dihydro-4H-pyrazolo[1,5-a]pyrazine-5-carboxamide (Example 14)

To a solution of (6S)-6-methyl-3-tetrahydrofuran-3-ylsulfonyl-4,5,6,7-tetrahydropyrazolo[1,5-a]pyrazine (compound 14d, 30.0 mg, 0.10 mmol) in CH$_2$Cl$_2$ (5.0 mL) was added Et$_3$N (50.5 mg, 0.50 mmol) and 2-chloro-1-fluoro-4-isocyanato-benzene (20.6 mg, 0.12 mmol) at room temperature. The reaction mixture was stirred at room temperature for 5 hours, then solvent was removed. The residue was purified by prep-HPLC to give Example 14 (15.3 mg) as a white solid. LCMS (M+H$^+$): 443. $^1$H NMR (METHANOL-d$_4$, 400 MHz) δ ppm 7.94 (s, 1H), 7.55-7.65 (m, 1H), 7.29-7.36 (m, 1H), 7.17 (t, J=9.0 Hz, 1H), 5.34 (d, J=18.4 Hz, 0.5H), 5.33 (d, J=18.4 Hz, 0.5H), 5.02-4.94 (m, 1H), 4.61-4.70 (m, 1H), 4.33-4.41 (m, 1H), 4.30-4.15 (m, 2H), 4.10-4.01 (m, 1H), 3.96-3.82 (m, 2H), 3.75-3.65 (m, 1H), 2.30-2.20 (m, 2H), 1.25 (d, J=6.9, Hz, 3H).

Example 15

(6S)-N-(3-chloro-4-fluoro-phenyl)-6-methyl-3-tetrahydropyran-4-ylsulfonyl-6,7-dihydro-4H-pyrazolo[1,5-a]pyrazine-5-carboxamide

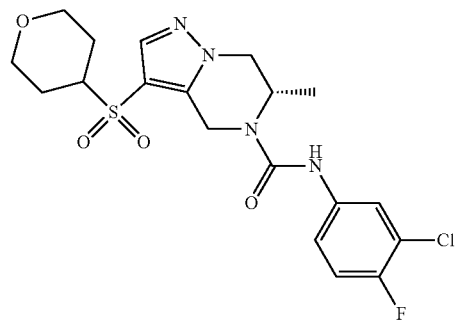 [SMILES: C[C@H]1Cn2ncc(S(=O)(=O)C3CCOCC3)c2CN1C(=O)Nc1ccc(F)c(Cl)c1]

Preparation of (6S)-N-(3-chloro-4-fluoro-phenyl)-6-methyl-3-tetrahydropyran-4-ylsulfonyl-6,7-dihydro-4H-pyrazolo[1,5-a]pyrazine-5-carboxamide (Example 15)

The title compound was prepared in analogy to the preparation of Example 14 by using 4-bromotetrahedron-pyran instead of 3-bromotetrahedronfuran. Example 15 (37 mg) was obtained as an off-white solid. LCMS (M+H$^+$): 457. $^1$H NMR (400 MHz, METHANOL-d$_4$) δ ppm 7.87 (s, 1H), 7.60 (dd, J=2.5, 6.7 Hz, 1H), 7.35-7.29 (m, 1H), 7.16 (t, J=9.0 Hz, 1H), 5.31 (d, J=18.2 Hz, 1H), 5.00-4.94 (m, 1H), 4.62 (d, J=18.2 Hz, 1H), 4.42-4.34 (m, 1H), 4.28-4.22 (m, 1H), 4.01 (d, J=11.9 Hz, 2H), 3.47-3.33 (m, 4H), 1.99-1.89 (m, 2H), 1.80-1.67 (m, 2H), 1.25 (d, J=6.9 Hz, 3H).

Example 16

(6S)-6-methyl-3-tetrahydrofuran-3-ylsulfonyl-N-(3,4,5-trifluorophenyl)-6,7-dihydro-4H-pyrazolo[1,5-a]pyrazine-5-carboxamide

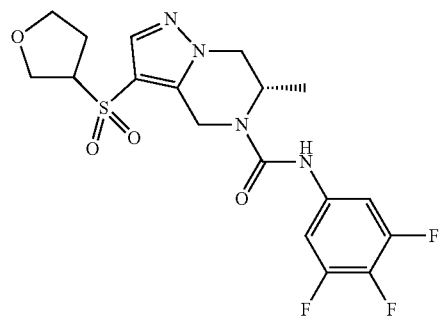 [SMILES: C[C@H]1Cn2ncc(S(=O)(=O)C3CCOC3)c2CN1C(=O)Nc1cc(F)c(F)c(F)c1]

Preparation of (6S)-6-methyl-3-tetrahydrofuran-3-ylsulfonyl-N-(3,4,5-trifluorophenyl)-6,7-dihydro-4H-pyrazolo[1,5-a]pyrazine-5-carboxamide (Example 16)

To a solution of (6S)-6-methyl-3-tetrahydrofuran-3-ylsulfonyl-4,5,6,7-tetrahydropyrazolo[1,5-a]pyrazine (compound 14d, 29.4 mg 0.20 mmol) in DCM (5.0 mL) was added DIPEA (51.6 mg 0.40 mmol) and a solution of triphosgene (17.8 mg 0.06 mmol) in DCM (1.0 mL) while keeping inner temperature 0° C. to 5° C. After being stirred at room temperature for 2 hours, the solution of 3,4,5-trifluoroaniline (30.0 mg 0.10 mmol) in DCM (1.0 mL) was added. The resulting mixture was stirred at room temperature for another 5 hours, solvent was then removed under reduced pressure. The residue was purified by prep-HPLC to give Example 16 (12.6 mg) as a white solid. LCMS (M+H$^+$): 445. $^1$H NMR (METHANOL-d$_4$, 400 MHz) δ ppm 7.94 (s, 1H), 7.27 (dd, J=10.3, 6.4 Hz, 2H), 5.34 (d, J=18.0 Hz, 0.5H), 5.33 (d, J=18.0, 0.5H), 5.01-4.94 (m, 1H), 4.65 (d, J=18.1 Hz, 0.5H), 4.64 (d, J=18.1 Hz, 0.5H), 4.40-4.32 (m, 1H), 4.24 (d, J=13.1 Hz, 1H), 4.23-4.18 (m, 1H), 4.10-4.01 (m, 1H), 3.95-3.80 (m, 2H), 3.79-3.69 (m, 1H), 2.36-2.22 (m, 2H), 1.25 (d, J=6.9, 1.1 Hz, 1.5H), 1.24 (d, J=6.9, 1.1 Hz, 1.5H).

Example 17

(6S)-N-(2-chloro-4-pyridyl)-6-methyl-3-tetrahydrofuran-3-ylsulfonyl-6,7-dihydro-4H-pyrazolo[1,5-a]pyrazine-5-carboxamide

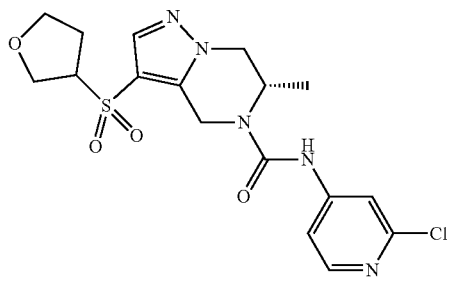 [SMILES: C[C@H]1Cn2ncc(S(=O)(=O)C3CCOC3)c2CN1C(=O)Nc1ccnc(Cl)c1]

Preparation of (6S)-N-(2-chloro-4-pyridyl)-6-methyl-3-tetrahydrofuran-3-ylsulfonyl-6,7-dihydro-4H-pyrazolo[1,5-a]pyrazine-5-carboxamide (Example 17)

To a solution of 2-chloropyridin-4-amine (25.7 mg 0.20 mmol) in DCM (5.0 mL) was added pyridine (51.6 mg 0.40 mmol) and then a solution of phenyl chloroformate (37.6 mg 0.24 mmol) in DCM (1.0 mL) at 0° C. The reaction mixture was stirred at room temperature for 3 hours, then quenched by sat NH$_4$Cl, diluted with EtOAc (50 mL). The organic layer was washed with sat NH$_4$Cl and brine, dried over Na$_2$SO$_4$ and concentrated. The residue was dissolved in DMAc (3.0 mL), to which was added (6S)-6-methyl-3-tetrahydrofuran-3-ylsulfonyl-4,5,6,7-tetrahydropyrazolo[1,5-a]pyrazine (compound 14d, 30.0 mg 0.10 mmol) and Et$_3$N (30.3 mg, 0.30 mmol) in DMAc (2.0 mL). The reaction mixture was stirred at room temperature for 3 hours, then purified by prep-HPLC to give Example 17 (18 mg) as a white solid. LCMS (M+H$^+$): 426. $^1$H NMR (METHANOL-d$_4$, 400 MHz) δ ppm 8.15 (d, J=5.6 Hz, 1H), 7.96 (s, 1H), 7.69 (s, 0.5H), 7.68 (s, 0.5H), 7.47 (d, J=5.6 Hz, 0.5H), 7.46 (d, J=5.6 Hz, 0.5H), 5.39 (d, J=18.0 Hz, 0.5H), 5.38 (d, J=18.0 Hz, 0.5H), 5.05-4.95 (m, 1H), 4.70 (d, J=18.0 Hz, 1H), 4.48-4.38 (m, 1H), 4.30-4.15 (m, 2H), 4.12-4.02 (m, 1H), 3.99-3.90 (m, 2H), 3.78-3.72 (m, 1H), 2.37-2.25 (m, 2H), 1.28 (d, J=6.9 Hz, 1.5H), 1.27 (d, J=6.9 Hz, 1.5H).

Example 18

(6S)-N-(2-chloro-4-pyridyl)-3-isopropylsulfonyl-6-methyl-6,7-dihydro-4H-pyrazolo[1,5-a]pyrazine-5-carboxamide The title compound was prepared according to the following scheme:

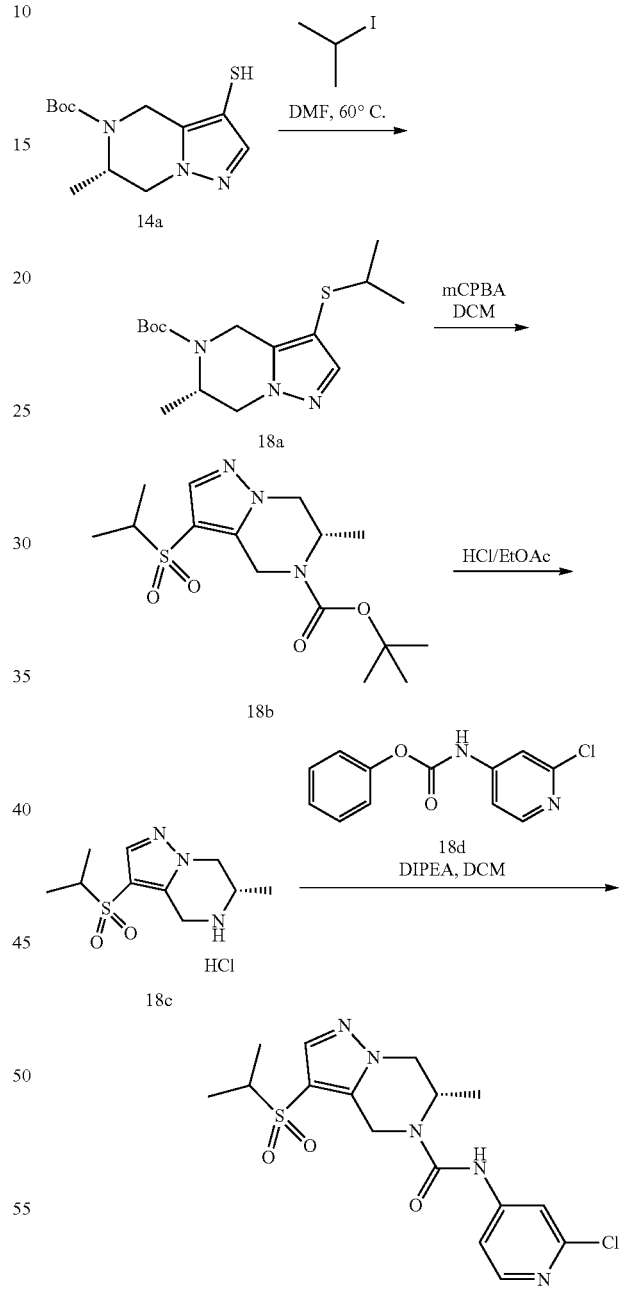

Step 1: Preparation of tert-butyl (6S)-3-isopropylsulfanyl-6-methyl-6,7-dihydro-4H-pyrazolo[1,5-a]pyrazine-5-carboxylate (compound 18a)

To a solution of tert-butyl (6S)-6-methyl-3-sulfanyl-6,7-dihydro-4H-pyrazolo[1,5-a]pyrazine-5-carboxylate (compound 14a, 600.0 mg, 2.23 mmol) in DMF (15.0 mL) was added 2-iodopropane (170.0 mg, 2.23 mmol). The mixture was stirred at 60° C. for 12 hours, then filtered. The filtrate was concentrated and the residue was purified by prep-HPLC to give compound 18a (200.0 mg) as a yellow oil. LCMS (M+H$^+$): 312.

Step 2: Preparation of tert-butyl (6S)-3-isopropylsulfonyl-6-methyl-6,7-dihydro-4H-pyrazolo[1,5-a]pyrazine-5-carboxylate (compound 18b)

To a solution of tert-butyl (6S)-3-isopropylsulfanyl-6-methyl-6,7-dihydro-4H-pyrazolo[1,5-a]pyrazine-5-carboxylate (compound 18a, 200.0 mg, 0.64 mmol) in DCM (20.0 mL) was added mCPBA (332.5 mg, 1.93 mmol) at 0° C. The reaction mixture was stirred at room temperature for 5 hours. Sodium sulfite solution (10.0 mL) was added. The mixture was extracted with DCM (10.0 mL) twice. The combined organic layer was washed with brine, dried over Na$_2$SO$_4$, and concentrated to afford crude product (150.0 mg) as a colorless oil. About 70.0 mg of crude product was used in next step, the other 80.0 mg was purified by prep-HPLC to give compound 18b (54 mg) as a white solid. LCMS (M+H$^+$): 344. $^1$H NMR (400 MHz, METHANOL-d$_4$) δ ppm 7.85 (s, 1H), 5.20 (d, J=18.7 Hz, 1H), 4.89-4.83 (m, 1H), 4.47 (d, J=18.7 Hz, 1H), 4.32-4.26 (m, 1H), 4.21-4.16 (m, 1H), 3.31-3.25 (m, 1H), 1.51 (s, 9H), 1.31 (d, J=6.8 Hz, 3H), 1.30 (d, J=6.8 Hz, 3H), 1.19 (d, J=7.0 Hz, 3H).

Step 3: Preparation of (6S)-3-isopropylsulfonyl-6-methyl-4,5,6,7-tetrahydropyrazolo[1,5-a]pyrazine (compound 18c)

To a solution of tert-butyl (6S)-3-isopropylsulfonyl-6-methyl-6,7-dihydro-4H-pyrazolo[1,5-a]pyrazine-5-carboxylate (compound 18b, 70.0 mg, 0.20 mmol) in EtOAc (10.0 mL) was added HCl/EtOAc (4 M, 10.0 mL). The reaction mixture was stirred at room temperature for 3 hours, then solvent was removed to give crude compound 18c (60.0 mg, crude) as a white solid.

Step 4: Preparation of (6S)-N-(2-chloro-4-pyridyl)-3-isopropylsulfonyl-6-methyl-6,7-dihydro-4H-pyrazolo[1,5-a]pyrazine-5-carboxamide (Example 18)

To a solution of (6S)-3-isopropylsulfonyl-6-methyl-4,5,6,7-tetrahydropyrazolo[1,5-a]pyrazine (compound 18c, 30.0 mg 0.11 mmol) in DMAc (5.0 mL) was added Et$_3$N (44.5 mg 0.44 mmol) and phenyl N-(2-chloro-4-pyridyl)carbamate (compound 18d, 35.6 mg, 0.14 mmol). The reaction mixture was stirred at room temperature for 5 hours, then concentrated. The residue was purified by prep-HPLC to give Example 18 (9 mg) as a white solid. LCMS (M+H$^+$): 398. $^1$HNMR (400 MHz, METHANOL-d$_4$) δ ppm 8.14 (d, J=6.0 Hz, 1H), 7.87 (s, 1H), 7.67 (d, J=2.0 Hz, 1H), 7.45 (dd, J=2.0, 6.0 Hz, 1H), 5.34 (d, J=18.4 Hz, 1H), 5.04-4.94 (m, 1H), 4.65 (d, J=18.4 Hz, 1H), 4.39 (dd, J=4.4, 12.8 Hz, 1H), 4.25 (d, J=12.8 Hz, 1H), 3.36-3.32 (m, 1H), 1.32 (d, J=6.8 Hz, 3H), 1.31 (d, J=6.8 Hz, 3H), 1.26 (d, J=6.9 Hz, 3H).

Example 19

(6S)-N-(2-chloro-4-pyridyl)-3-cyclopentylsulfonyl-6-methyl-6,7-dihydro-4H-pyrazolo[1,5-a]pyrazine-5-carboxamide

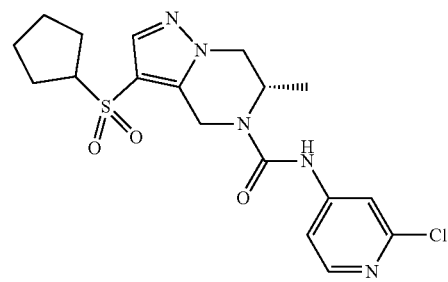 [SMILES: C[C@H]1Cn2ncc(S(=O)(=O)C3CCCC3)c2CN1C(=O)Nc1ccnc(Cl)c1]

Preparation of (6S)-N-(2-chloro-4-pyridyl)-3-cyclopentylsulfonyl-6-methyl-6,7-dihydro-4H-pyrazolo[1,5-a]pyrazine-5-carboxamide (Example 19)

The title compound was prepared in analogy to Example 18 by using 3-bromocyclopentane instead of 2-iodopropane. Example 19 (10 mg) was obtained as a white solid. LCMS (M+H$^+$): 424. $^1$H NMR (400 MHz, METHANOL-d$_4$) δ ppm 8.13 (d, J=6.0 Hz, 1H), 7.90 (s, 1H), 7.67 (d, J=1.8 Hz, 1H), 7.44 (dd, J=2.0, 5.6 Hz, 1H), 5.35 (d, J=18.2 Hz, 1H), 4.99 (m, 1H), 4.67 (d, J=18.2 Hz, 1H), 4.43-4.33 (m, 1H), 4.25 (d, J=12.8 Hz, 1H), 3.77-3.65 (m, 1H), 2.06-1.91 (m, 4H), 1.80-1.63 (m, 4H), 1.26 (d, J=6.9 Hz, 3H).

Example 20

(6S)-3-isopropylsulfonyl-6-methyl-N-(3,4,5-trifluorophenyl)-6,7-dihydro-4H-pyrazolo[1,5-a]pyrazine-5-carboxamide

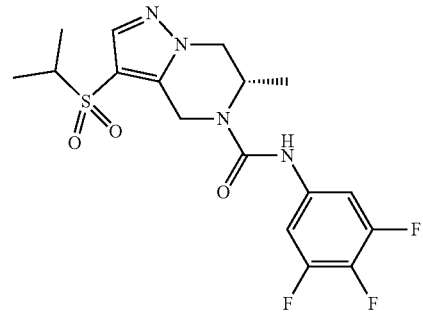 [SMILES: CC(C)S(=O)(=O)c1cnn2c1CN(C(=O)Nc1cc(F)c(F)c(F)c1)[C@@H](C)C2]

Preparation of (6S)-3-isopropylsulfonyl-6-methyl-N-(3,4,5-trifluorophenyl)-6,7-dihydro-4H-pyrazolo[1,5-a]pyrazine-5-carboxamide (Example 20)

To a solution 3,4,5-trifluoroaniline (32.4 mg 0.22 mmol) in DCM (5.0 ml) was added DIPEA (56.8 mg 0.44 mmol) and triphosgene (20.8 mg 0.07 mmol) in DCM (1.0 mL) while keeping inner temperature at 0° C. to 5° C. The reaction mixture was stirred at room temperature for 2 hours, then (6S)-3-isopropylsulfonyl-6-methyl-4,5,6,7-tetrahydropyrazolo[1,5-a]pyrazine (compound 18c, 30.0 mg 0.11 mmol) in DCM (1.0 mL) was added. The resulting mixture was stirred at room temperature for another 5 hours, then solvent was removed under reduced pressure. The residue was purified by prep-HPLC to give Example 20 (10 mg) as a white solid. LCMS (M+H$^+$): 417. $^1$H NMR (400 MHz, METHANOL-d$_4$) δ ppm 7.89 (s, 1H), 7.35-7.25 (m, 2H), 5.32 (d, J=18.2 Hz, 1H), 5.03-4.95 (m, 1H), 4.64 (d, J=18.1 Hz, 1H), 4.39 (dd, J=4.4, 12.8 Hz, 1H), 4.26 (d, J=12.8 Hz, 1H), 3.34-3.38 (m, 1H), 1.34 (d, J=6.9 Hz, 3H), 1.33 (d, J=6.9 Hz, 3H), 1.27 (d, J=6.9 Hz, 3H).

Example 21

(6S)-N-[2-(difluoromethyl)-4-pyridyl]-3-isopropyl-sulfonyl-6-methyl-6,7-dihydro-4H-pyrazolo[1,5-a]pyrazine-5-carboxamide

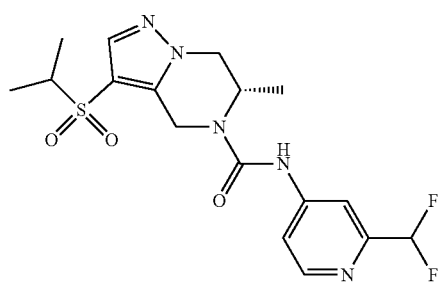 [SMILES: CC(C)S(=O)(=O)c1cnn2c1CN(C(=O)Nc1ccnc(C(F)F)c1)[C@@H](C)C2]

The title compound was prepared according to the following scheme:

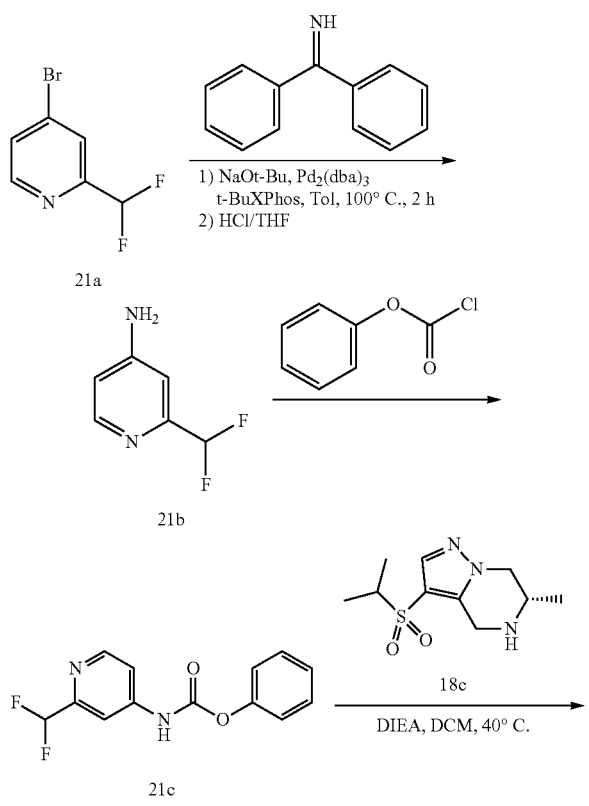

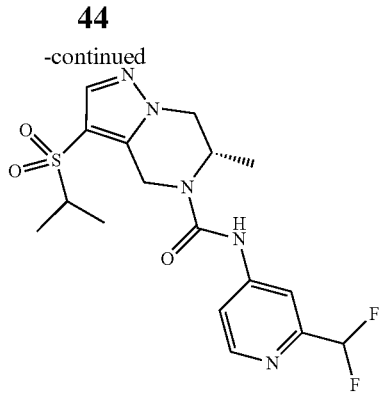

Step 1: Preparation of 2-(difluoromethyl)pyridin-4-amine (compound 21b)

To a solution of 4-bromo-2-(difluoromethyl)pyridine (compound 21a, 416 mg, 2.0 mmol) and diphenylmethanimine (725 mg, 4 mmol) in toluene (15.0 mL) was added Pd$_2$(dba)$_3$ (91.6 mg, 100 μmol), t-BuXPhos (84.9 mg, 200 μmol) and NaOt-Bu (577 mg, 6 mmol). The resulting mixture was flushed with nitrogen, sealed, heated to 100° C. and stirred for 2 hours. The reaction mixture was then cooled to room temperature, diluted with ethyl acetate, washed with water and brine, dried over Na$_2$SO$_4$ and concentrated. The residue was dissolved in THF (4.0 mL) and concentrated HCl (0.5 mL, 6 mmol) was added. The mixture was stirred at room temperature for 1 hour, then concentrated to give a crude compound 21b (620 mg, crude) which was used directly in next step. LCMS (M+H$^+$): 145.

Step 2: Preparation of phenyl N-[2-(difluoromethyl)-4-pyridyl]carbamate (compound 21c)

To a solution of 2-(difluoromethyl)pyridin-4-amine (compound 21b, 620 mg, crude) was added DIPEA (754 mg, 1.0 mL, 5.83 mmol) and phenylchloroformate (313 mg, 251 μL, 2 mmol). The reaction mixture was stirred at room temperature for 1 hour, then concentrated. The residue was purified by column chromatography to give compound 21c (264 mg) as a brown solid. LCMS (M+H$^+$): 265.

Step 3: Preparation of (6S)-N-[2-(difluoromethyl)-4-pyridyl]-3-isopropylsulfonyl-6-methyl-6,7-dihydro-4H-pyrazolo[1,5-a]pyrazine-5-carboxamide (Example 21)

To a solution of (6S)-3-isopropylsulfonyl-6-methyl-4,5,6,7-tetrahydropyrazolo[1,5-a]pyrazine (compound 18c, 36 mg, 150 μmol) in DMF (3.0 mL) was added DIPEA (377 mg, 0.5 mL, 2.92 mmol) and phenyl (2-(difluoromethyl)pyridin-4-yl)carbamate (compound 21c, 47.6 mg, 180 μmol). The resulting mixture was stirred at room temperature overnight and then directly purified by prep-HPLC to give Example 21 (39 mg) as a white solid. LCMS (M+H$^+$): 414. $^1$H NMR (400 MHz, CHLOROFORM-d) δ ppm 8.49 (d, J=5.5 Hz, 1H), 7.81 (s, 1H), 7.75-7.69 (m, 2H), 7.64-7.58 (m, 1H), 6.60 (t, J=55.6 Hz, 1H), 5.25 (d, J=17.6 Hz, 1H), 5.21-5.10 (m, 1H), 4.65 (d, J=17.6 Hz, 1H), 4.34 (dd, J=4.5, 13.1 Hz, 1H), 4.19 (d, J=12.8 Hz, 1H), 3.20 (quin, J=6.8 Hz, 1H), 1.35 (d, J=6.9 Hz, 3H), 1.34 (d, J=6.9 Hz, 3H), 1.26 (d, J=7.0 Hz, 3H).

Example 22

(6S)-3-cyclopropylsulfonyl-6-methyl-N-(3,4,5-trifluorophenyl)-6,7-dihydro-4H-pyrazolo[1,5-a]pyrazine-5-carboxamide

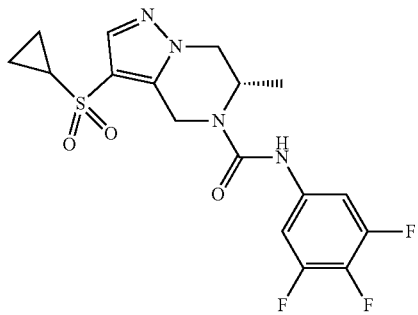 [SMILES: C[C@H]1Cn2ncc(S(=O)(=O)C3CC3)c2CN1C(=O)Nc1cc(F)c(F)c(F)c1]

The title compound was prepared according to the following scheme:

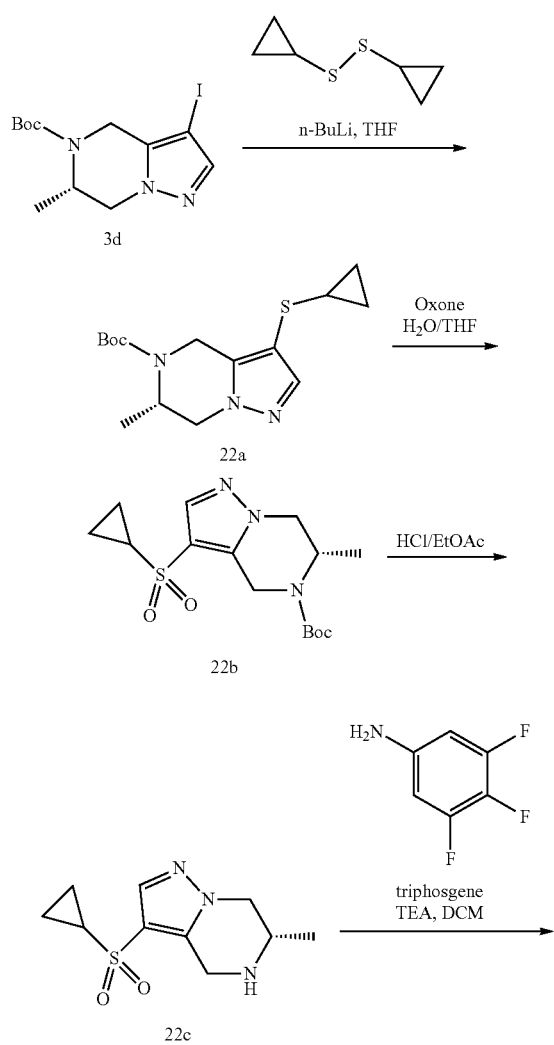

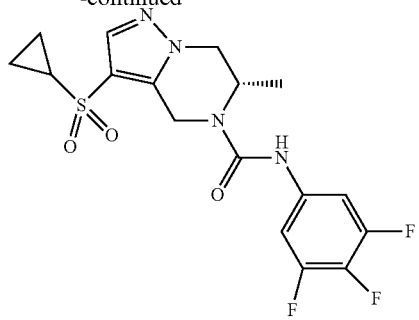

22

Step 1: Preparation of tert-butyl (6S)-3-cyclopropylsulfanyl-6-methyl-6,7-dihydro-4H-pyrazolo[1,5-a]pyrazine-5-carboxylate (compound 22a)

To the solution of tert-butyl (6S)-3-iodo-6-methyl-6,7-dihydro-4H-pyrazolo[1,5-a]pyrazine-5-carboxylate (compound 3d, 200.0 mg, 0.55 mmol) in THF (5.0 mL) was added n-BuLi (0.44 mL, 1.1 mmol) at −78° C. under $N_2$, the reaction mixture was stirred at −78° C. for 1 hour. Then (cyclopropyldisulfanyl)cyclopropane (121.2 mg 0.83 mmol) was added. The resulting mixture was warmed to 0° C. and stirred for 1 hour, then stirred at room temperature for another 12 hours, then concentrated to provide crude compound 22a (200.0 mg) which was used directly in the next step. LCMS (M+H$^+$): 310.

Step 2: Preparation of tert-butyl (6S)-3-cyclopropylsulfonyl-6-methyl-6,7-dihydro-4H-pyrazolo[1,5-a]pyrazine-5-carboxylate (compound 22b)

To a solution of tert-butyl (6S)-3-cyclopropylsulfanyl-6-methyl-6,7-dihydro-4H-pyrazolo[1,5-a]pyrazine-5-carboxylate (compound 22a, 200.0 mg, 0.65 mmol) in $H_2O$/THF (10.0 mL, v/v=1/1) was added oxone (197.6 mg, 1.3 mmol) at room temperature under $N_2$.

The reaction mixture was stirred at room temperature for 5 hours, then diluted with EtOAc. The organic layer was washed with sat $NH_4Cl$ and brine, dried over $Na_2SO_4$ and concentrated to give crude compound 22b (30.0 mg) as a yellow oil which was used directly in next step. LCMS (M+H$^+$): 342.

Step 3: Preparation of (6S)-3-cyclopropylsulfonyl-6-methyl-4,5,6,7-tetrahydropyrazolo[1,5-a]pyrazine (compound 22c)

To a solution of tert-butyl (6S)-3-cyclopropylsulfonyl-6-methyl-6,7-dihydro-4H-pyrazolo[1,5-a]pyrazine-5-carboxylate (compound 22b, 30.0 mg, 0.09 mmol) in EtOAc (5 mL) was added HCl/EtOAc (4 M, 5.0 mL). The reaction mixture was stirred at room temperature for 1 hour, then concentrated to provide crude compound 22c (30.0 mg crude) as a yellowish solid.

Step 4: Preparation of (6S)-3-cyclopropylsulfonyl-6-methyl-N-(3,4,5-trifluorophenyl)-6,7-dihydro-4H-pyrazolo[1,5-a]pyrazine-5-carboxamide (Example 27)

To a solution of 3,4,5-trifluoroaniline (32.6 mg 0.22 mmol) and DIPEA (56.76 mg 0.44 mmol) in DCM (5.0 ml)

was added triphosgene (20.77 mg 0.07 mmol) in DCM (1.0 mL) dropwise while keeping inner temperature at 0° C. to 5° C. After being stirred at room temperature for 1 hour, (6S)-3-cyclopropylsulfonyl-6-methyl-4,5,6,7-tetrahydropyrazolo[1,5-a]pyrazine (compound 22c, 30.0 mg 0.11 mmol) in DCM (3.0 mL) was added. The reaction mixture was stirred at room temperature for 3 hours, then solvent was removed to provide a crude product which was purified by prep-HPLC to give Example 27 (5.0 mg) as a white solid. LCMS (M+H+): 415. $^1$H NMR (400 MHz, CHLOROFORM-d) δ ppm 7.77 (s, 1H), 7.18-6.99 (m, 2H), 6.83 (br. s., 1H), 5.14-5.00 (m, 2H), 4.64 (d, J=17.3 Hz, 1H), 4.28 (d, J=9.0 Hz, 1H), 4.19-4.10 (m, 1H), 2.50 (m, 1H), 1.34-1.26 (m, 2H), 1.19 (d, J=6.4 Hz, 3H), 1.07-1.00 (m, 2H).

Example 23

(6S)-N-(3-chloro-4-fluoro-phenyl)-6-methyl-3-pyrrolidin-1-ylsulfonyl-6,7-dihydro-4H-pyrazolo[1,5-a]pyrazine-5-carboxamide The title compound was prepared according to the following scheme:

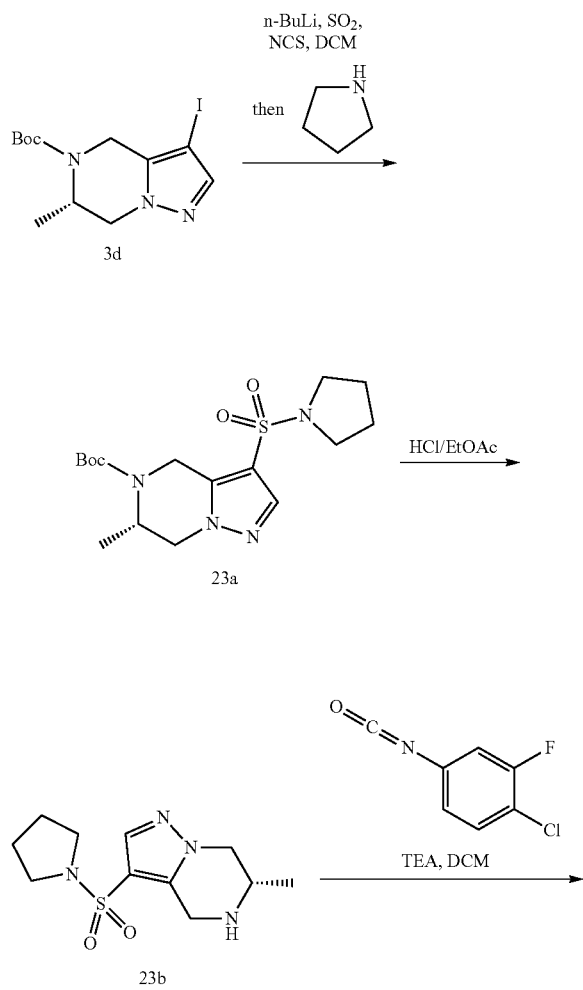

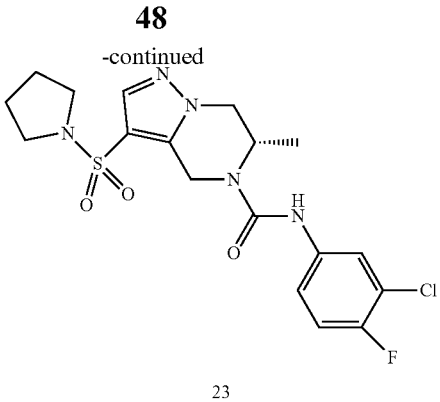

Step 1: Preparation of tert-butyl (6S)-6-methyl-3-pyrrolidin-1-ylsulfonyl-6,7-dihydro-4H-pyrazolo[1,5-a]pyrazine-5-carboxylate (compound 23a)

To a solution of tert-butyl (6S)-3-iodo-6-methyl-6,7-dihydro-4H-pyrazolo[1,5-a]pyrazine-5-carboxylate (compound 3d, 363.2 mg, 1.0 mmol) in Et$_2$O (10.0 m) was added n-BuLi (0.44 mL, 1.1 mmol) at −60° C. under N$_2$. After being stirred at −60° C. for 1 hour, the reaction mixture was charged with SO$_2$ (15.0 mL), warmed to room temperature and stirred for another hour. Then solvent was removed, the residue was dissolved in DCM (10.0 mL), to which was added NCS (146.9 mg, 1.1 mmol). After the reaction mixture was stirred at room temperature for 3 hours, pyrrolidine (78.2 mg, 1.1 mmol) was added. The resulting mixture was stirred at room temperature for 12 hours, then concentrated. The residue was purified by prep-HPLC to give compound 23a (50.0 mg) as a white solid. LCMS (M+H+): 371.

Step 2: Preparation of (6S)-6-methyl-3-pyrrolidin-1-ylsulfonyl-4,5,6,7-tetrahydropyrazolo[1,5-a]pyrazine (compound 23b)

To a solution of tert-butyl (6S)-6-methyl-3-pyrrolidin-1-ylsulfonyl-6,7-dihydro-4H-pyrazolo[1,5-a]pyrazine-5-carboxylate (compound 23a, 50.0 mg, 0.135 mmol) in EtOAc (5.0 mL) was added HCl/EtOAc (5.0 mL). The reaction mixture was stirred at room temperature for 2 hours, then solvent was removed under reduced pressure to give crude compound 23b (30.0 mg, crude) as a white solid. LCMS (M+H+): 271.

Step 3: Preparation of (6S)-N-(3-chloro-4-fluoro-phenyl)-6-methyl-3-pyrrolidin-1-ylsulfonyl-6,7-dihydro-4H-pyrazolo[1,5-a]pyrazine-5-carboxamide (Example 23)

To a solution of (6S)-6-methyl-3-pyrrolidin-1-ylsulfonyl-4,5,6,7-tetrahydropyrazolo[1,5-a]pyrazine (compound 23b, 30.0 mg, 0.098 mmol) in DCM (5.0 mL) was added DIPEA (37.9 mg, 0.294 mmol) and 1-chloro-2-fluoro-4-isocyanatobenzene (16.7 mg, 0.098 mmol) at 0° C. The reaction mixture was stirred at room temperature for 1 hour, then solvent was removed to give a crude product which was purified by prep-HPLC to afford Example 23 (14.0 mg) as a white solid. LCMS (M+H+): 442. $^1$H NMR (400 MHz, METHANOL-d$_4$) δ ppm 7.90 (s, 1H), 7.62 (dd, J=2.6, 6.7 Hz, 1H), 7.37-7.30 (m, 1H), 7.18 (t, J=9.0 Hz, 1H), 5.33 (d, J=18.1 Hz, 1H), 4.69-4.61 (m, 2H), 4.43-4.34 (m, 1H), 4.29-4.22 (m, 1H), 3.27 (t, J=6.7 Hz, 4H), 1.85 (m, 4H), 1.27 (d, J=6.9 Hz, 3H).

Example 24

(6S)-N-(3-chloro-4-fluoro-phenyl)-3-(dimethylsulfamoyl)-6-methyl-6,7-dihydro-4H-pyrazolo[1,5-a]pyrazine-5-carboxamide

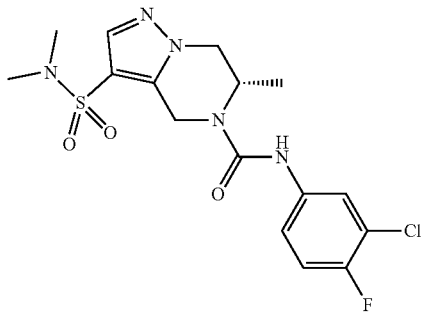 [SMILES: C[C@H]1Cn2ncc(S(=O)(=O)N(C)C)c2CN1C(=O)Nc1ccc(F)c(Cl)c1]

Preparation of (6S)-N-(3-chloro-4-fluoro-phenyl)-3-(dimethylsulfamoyl)-6-methyl-6,7-dihydro-4H-pyrazolo[1,5-a]pyrazine-5-carboxamide (Example 24)

The title compound was prepared in analogy to the preparation of Example 23 by using dimethylamine instead of pyrrolidine. Example 24 (10 mg) was obtained as a white solid. LCMS (M+H$^+$): 416. $^1$H NMR (400 MHz, METHANOL-d$_4$) δ ppm 7.87 (s, 1H), 7.62 (dd, J=2.6, 6.7 Hz, 1H), 7.36-7.31 (m, 1H), 7.21-7.16 (m, 1H), 5.32 (d, J=17.7 Hz, 1H), 4.66-4.60 (m, 2H), 4.43-4.37 (m, 1H), 4.29-4.24 (m, 1H), 2.75 (s, 6H), 1.27 (d, J=6.9 Hz, 3H).

Example 25

(6S)-N-(3-chloro-4-fluoro-phenyl)-3-(isopropylsulfamoyl)-6-methyl-6,7-dihydro-4H-pyrazolo[1,5-a]pyrazine-5-carboxamide

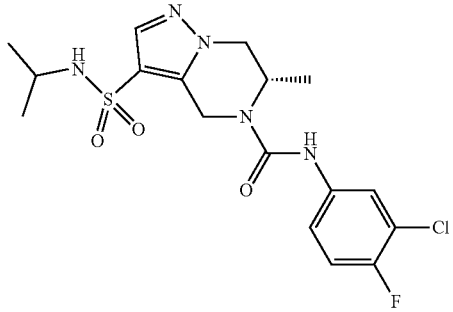 [SMILES: CC(C)NS(=O)(=O)c1cnn2c1CN(C(=O)Nc1ccc(F)c(Cl)c1)[C@@H](C)C2]

Preparation of (6S)-N-(3-chloro-4-fluoro-phenyl)-3-(isopropylsulfamoyl)-6-methyl-6,7-dihydro-4H-pyrazolo[1,5-a]pyrazine-5-carboxamide (Example 25)

The title compound was prepared in analogy to the preparation of Example 23 by using isopropylamine instead of pyrrolidine. Example 24 (10 mg) was obtained as a white solid. LCMS (M+H$^+$): 430. $^1$H NMR (400 MHz, METHANOL-d$_4$) δ ppm 7.82 (s, 1H), 7.65-7.58 (m, 1H), 7.37-7.27 (m, 1H), 7.17 (t, J=8.8 Hz, 1H), 5.34-5.24 (d, J=18.0 Hz, 1H), 5.00-4.91 (m, 1H), 4.59 (d, J=18.4 Hz, 1H), 4.42-4.31 (m, 1H), 4.22 (d, J=13.2 Hz, 1H), 3.50-3.37 (m, 1H), 1.24 (d, J=6.9 Hz, 3H), 1.10 (d, J=6.4 Hz, 3H), 1.08 (d, J=6.4 Hz, 3H).

Example 26

(6S)-N-(3-chloro-4-fluoro-phenyl)-6-methyl-3-[[(3S)-tetrahydrofuran-3-yl]sulfamoyl]-6,7-dihydro-4H-pyrazolo[1,5-a]pyrazine-5-carboxamide

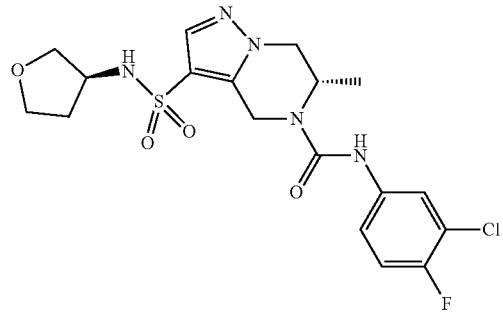 [SMILES: C[C@H]1Cn2ncc(S(=O)(=O)N[C@H]3CCOC3)c2CN1C(=O)Nc1ccc(F)c(Cl)c1]

Preparation of (6S)-N-(3-chloro-4-fluoro-phenyl)-6-methyl-3-[[(3S)-tetrahydrofuran-3-yl]sulfamoyl]-6,7-dihydro-4H-pyrazolo[1,5-a]pyrazine-5-carboxamide (Example 26)

The title compound was prepared in analogy to the preparation of Example 23 by using (3S)-tetrahydrofuran-3-amine instead of pyrrolidine. Example 26 (15 mg) was obtained as a white solid. LCMS (M+H$^+$): 458. $^1$H NMR (400 MHz, METHANOL-d$_4$) δ ppm 7.84 (s, 1H), 7.64-7.58 (m, 1H), 7.37-7.28 (m, 1H), 7.17 (t, J=8.8 Hz, 1H), 5.30 (d, J=18.0 Hz, 1H), 4.99-4.91 (m, 1H), 4.59 (d, J=18.4 Hz, 1H), 4.41-4.31 (m, 1H), 4.23 (d, J=12.8 Hz, 1H), 3.94-3.88 (m, 1H), 3.87-3.81 (m, 1H), 3.80-3.76 (m, 1H), 3.73-3.69 (m, 1H), 3.62-3.50 (m, 1H), 2.15-2.04 (m, 1H), 1.81-1.72 (m, 1H), 1.25 (d, J=6.9 Hz, 3H).

Example 27

(6S)-3-[(2-hydroxy-1,1-dimethyl-ethyl)sulfamoyl]-6-methyl-N-(3,4,5-trifluorophenyl)-6,7-dihydro-4H-pyrazolo[1,5-a]pyrazine-5-carboxamide

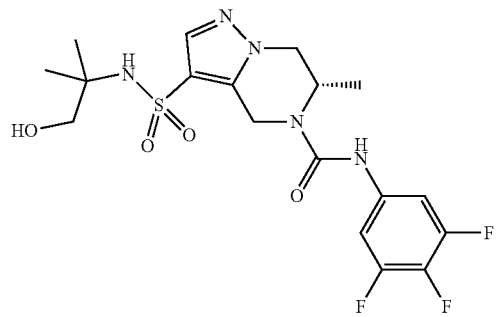 [SMILES: C[C@H]1Cn2ncc(S(=O)(=O)NC(C)(C)CO)c2CN1C(=O)Nc1cc(F)c(F)c(F)c1]

The title compound was prepared according to the following scheme:

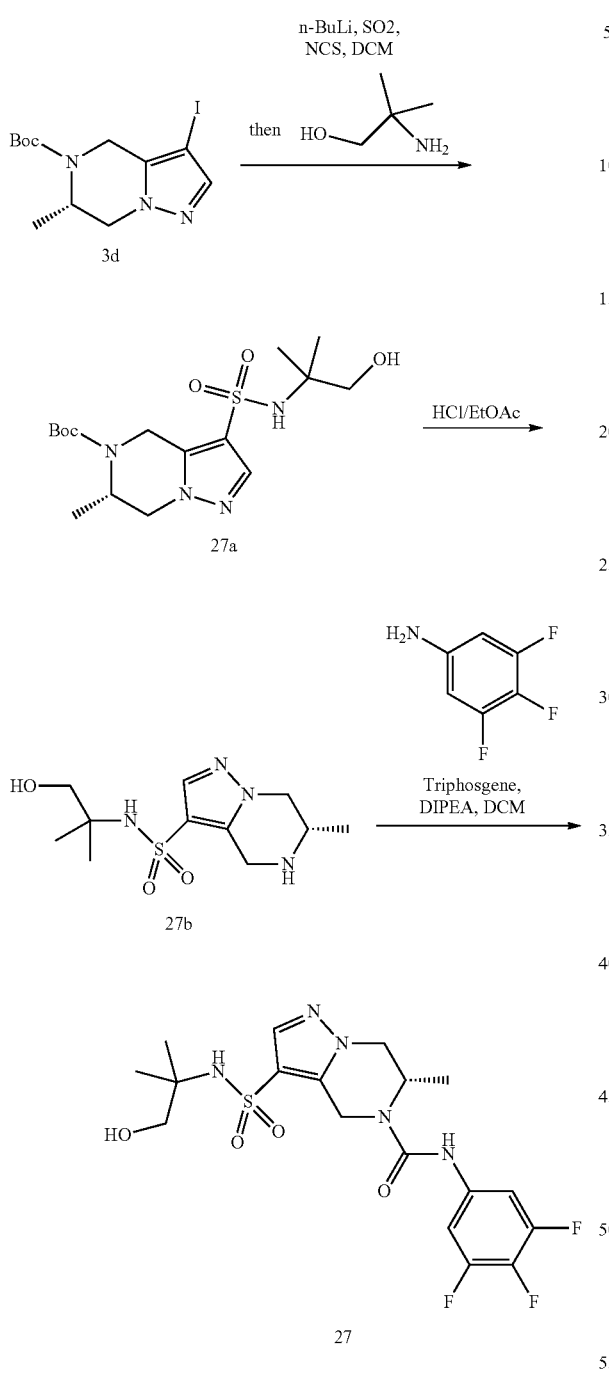

Preparation of (6S)-N-(2-hydroxy-1,1-dimethyl-ethyl)-6-methyl-4,5,6,7-tetrahydropyrazolo[1,5-a]pyrazine-3-sulfonamide (compound 27b)

The title compound was prepared in analogy to (6S)-6-methyl-3-pyrrolidin-1-ylsulfonyl-4,5,6,7-tetrahydropyrazolo[1,5-a]pyrazine (compound 23b) by using 2-amino-2-methyl-propan-1-ol instead of pyrrolidine. Crude compound 27b (60.0 mg) was obtained as light-green solid.

Preparation of (6S)-3-[(2-hydroxy-1,1-dimethyl-ethyl)sulfamoyl]-6-methyl-N-(3,4,5-trifluorophenyl)-6,7-dihydro-4H-pyrazolo[1,5-a]pyrazine-5-carboxamide (Example 27)

To a solution of 3,4,5-trifluoroaniline (52.9 mg, 0.36 mmol) and DIPEA (92.1 mg, 0.72 mmol) in DCM (5.0 ml) was added triphosgene (32.6 mg, 0.11 mmol) in DCM (1.0 mL) while keeping inner temperature at 0° C. to 5° C. After being stirred at room temperature for 2 hours, (6S)-N-(2-hydroxy-1,1-dimethyl-ethyl)-6-methyl-4,5,6,7-tetrahydropyrazolo[1,5-a]pyrazine-3-sulfonamide (compound 27b, 60.0 mg, 0.18 mmol) was added. The reaction mixture was stirred at room temperature for 5 hours, then solvent was removed under reduced pressure to give a crude product which was purified by prep-HPLC to afford Example 27 (9 mg) as a white solid. LCMS (M+H$^+$): 462. $^1$H NMR (400 MHz, CHLOROFORM-d) δ ppm 7.85 (s, 1H), 7.23-7.11 (m, 3H), 5.29 (s, 1H), 5.21-5.08 (m, 1H), 5.13 (d, J=17.2 Hz, 1H), 4.63 (d, J=17.2 Hz, 1H), 4.32 (dd, J=4.4, 12.8 Hz, 1H), 4.19 (d, J=12.8 Hz, 1H), 3.52 (dd, J=11.2, 24.4 Hz, 2H), 1.26 (s, 3H), 1.24 (s, 3H), 1.23 (d, J=6.8 Hz, 3H).

Example 28

(6S)-3-(3,3-difluoropyrrolidin-1-yl)sulfonyl-6-methyl-N-(3,4,5-trifluorophenyl)-6,7-dihydro-4H-pyrazolo[1,5-a]pyrazine-5-carboxamide

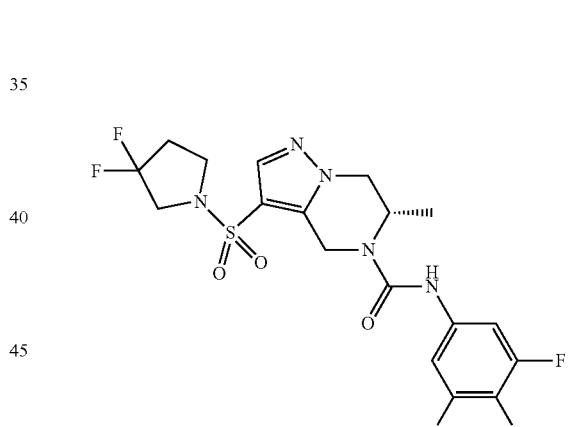

Preparation of (6S)-3-(3,3-difluoropyrrolidin-1-yl)sulfonyl-6-methyl-N-(3,4,5-trifluorophenyl)-6,7-dihydro-4H-pyrazolo[1,5-a]pyrazine-5-carboxamide (Example 28)

The title compound was prepared in analogy to the preparation of Example 27 by using difluoropyrrolidine instead of 2-amino-2-methyl-propan-1-ol. Example 28 (8.5 mg) was obtained as a white solid. LCMS (M+H$^+$): 480. $^1$H NMR (400 MHz, METHANOL-d4) δ ppm 7.93 (s, 1H), 7.26 (dd, J=6.3, 10.2 Hz, 2H), 5.30 (d, J=18.1 Hz, 1H), 4.97-4.93 (m, 1H), 4.61 (d, J=18.4 Hz, 1H), 4.43-4.33 (m, 1H), 4.24 (d, J=12.8 Hz, 1H), 3.60 (t, J=12.8 Hz, 2H), 3.46 (t, J=7.6 Hz, 2H), 2.44-2.32 (m, 2H), 1.25 (d, J=6.9 Hz, 3H).

Example 29

(6S)-3-[(3R)-3-hydroxypyrrolidin-1-yl]sulfonyl-6-methyl-N-(3,4,5-trifluorophenyl)-6,7-dihydro-4H-pyrazolol[1,5-a]pyrazine-5-carboxamide

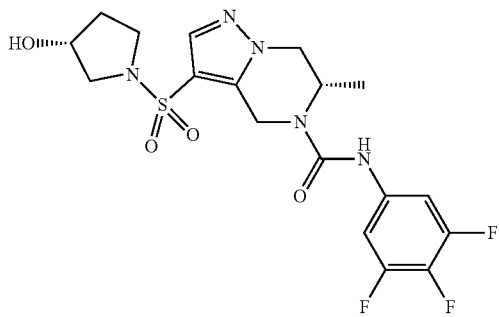 [SMILES: C[C@H]1Cn2ncc(S(=O)(=O)N3CC[C@@H](O)C3)c2CN1C(=O)Nc1cc(F)c(F)c(F)c1]

Preparation of (6S)-3-[(3R)-3-hydroxypyrrolidin-1-yl]sulfonyl-6-methyl-N-(3,4,5-trifluorophenyl)-6,7-dihydro-4H-pyrazolo[1,5-a]pyrazine-5-carboxamide (Example 29)

The title compound was prepared in analogy to the preparation of Example 27 by using (3R)-pyrrolidin-3-ol instead of 2-amino-2-methyl-propan-1-ol. Example 28 (19.2 mg) was obtained as a white solid. LCMS (M+H$^+$): 460. $^1$H NMR (400 MHz, METHANOL-d4) δ ppm 7.87 (s, 1H), 7.30-7.23 (m, 2H), 5.31 (d, J=18.0 Hz, 1H), 4.98-4.92 (m, 1H), 4.66 (d, J=18.4 Hz, 1H), 4.39-4.31 (m, 2H), 4.21 (d, J=12.8 Hz, 1H), 3.43-3.33 (m, 3H), 3.28-3.21 (m, 1H), 2.03-1.92 (m, 1H), 1.88-1.79 (m, 1H), 1.25 (d, J=6.9 Hz, 3H).

Example 30

(6S)-6-methyl-3-[[(3R)-tetrahydrofuran-3-yl]sulfamoyl]-N-(3,4,5-trifluorophenyl)-6,7-dihydro-4H-pyrazolo[1,5-a]pyrazine-5-carboxamide

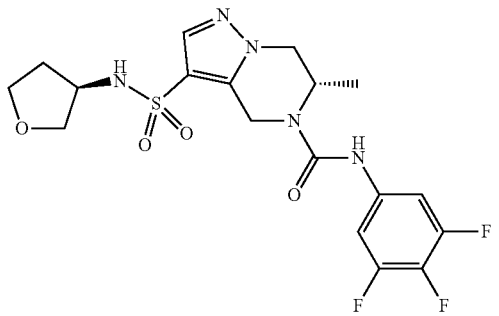 [SMILES: C[C@H]1Cn2ncc(S(=O)(=O)N[C@@H]3CCOC3)c2CN1C(=O)Nc1cc(F)c(F)c(F)c1]

Preparation of (6S)-6-methyl-3-[[(3R)-tetrahydrofuran-3-yl]sulfamoyl]-N-(3,4,5-trifluorophenyl)-6,7-dihydro-4H-pyrazolo[1,5-a]pyrazine-5-carboxamide (Example 30)

The title compound was prepared in analogy to the preparation of Example 27 by using (3R)-tetrahydrofuran-3-amine instead of 2-amino-2-methyl-propan-1-ol. Example 30 (10 mg) was obtained as a white solid. LCMS (M+H$^+$): 460. $^1$H NMR (400 MHz, METHANOL-d$_4$) δ ppm 7.84 (s, 1H), 7.31-7.23 (m, 2H), 5.30 (d, J=18.1 Hz, 1H), 4.98-4.91 (m, 1H), 4.59 (d, J=18.1 Hz, 1H), 4.40-4.32 (m, 1H), 4.22 (d, J=12.8 Hz, 1H), 3.93-3.82 (m, 2H), 3.79-3.69 (m, 2H), 3.58-3.51 (m, 1H), 2.17-2.06 (m, 1H), 1.84-1.73 (m, 1H), 1.25 (d, J=6.9 Hz, 3H).

Example 31

(6S)-3-(3,3-difluoroazetidin-1-yl)sulfonyl-6-methyl-N-(3,4,5-trifluorophenyl)-6,7-dihydro-4H-pyrazolo[1,5-a]pyrazine-5-carboxamide

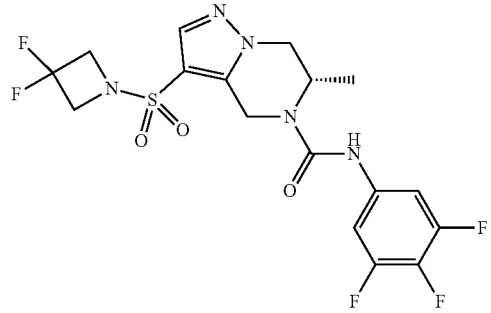 [SMILES: C[C@H]1Cn2ncc(S(=O)(=O)N3CC(F)(F)C3)c2CN1C(=O)Nc1cc(F)c(F)c(F)c1]

Preparation of (6S)-3-(3,3-difluoroazetidin-1-yl)sulfonyl-6-methyl-N-(3,4,5-trifluorophenyl)-6,7-dihydro-4H-pyrazolo[1,5-a]pyrazine-5-carboxamide (Example 31)

The title compound was prepared in analogy to the preparation of Example 27 by using 3,3-difluoroazetidine instead of 2-amino-2-methyl-propan-1-ol. Example 31 (22.5 mg) was obtained as a white solid. LCMS (M+H$^+$): 466. $^1$H NMR (400 MHz, METHANOL-d$_4$) δ ppm 8.01 (s, 1H), 7.31-7.23 (m, 2H), 5.30 (d, J=18.2 Hz, 1H), 5.00-4.94 (m, 1H), 4.62 (d, J=18.2 Hz, 1H), 4.38 (m, 1H), 4.28 (d, J=12.0 Hz, 1H), 4.25-4.14 (m, 4H), 1.26 (d, J=6.9 Hz, 3H).

Example 32

(6S)-6-methyl-3-morpholinosulfonyl-N-(3,4,5-trifluorophenyl)-6,7-dihydro-4H-pyrazolo[1,5-a]pyrazine-5-carboxamide

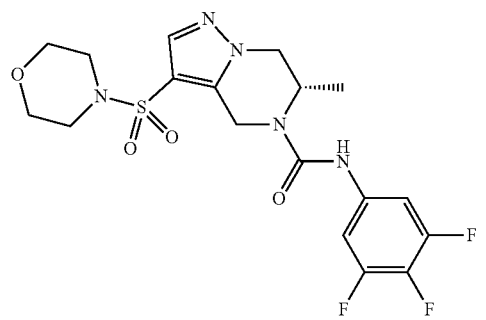 [SMILES: C[C@H]1Cn2ncc(S(=O)(=O)N3CCOCC3)c2CN1C(=O)Nc1cc(F)c(F)c(F)c1]

Preparation of (6S)-6-methyl-3-morpholinosulfonyl-N-(3,4,5-trifluorophenyl)-6,7-dihydro-4H-pyrazolo[1,5-a]pyrazine-5-carboxamide (Example 32)

The title compound was prepared in analogy to the preparation of Example 27 by using morpholine instead of 2-amino-2-methyl-propan-1-ol. Example 32 (4.0 mg) was obtained as a white solid. LCMS (M+H⁺): 460. ¹H NMR (400 MHz, METHANOL-d₄) δ ppm 7.84 (s, 1H), 7.30-7.23 (m, 2H), 5.27 (d, J=18.2 Hz, 1H), 5.00-4.90 (m, 1H), 4.59 (d, J=18.0 Hz, 1H), 4.42-4.34 (m, 1H), 4.25 (d, J=12.8 Hz, 1H), 3.75 (t, J=4.7 Hz, 4H), 3.02 (dd, J=3.1, 5.2 Hz, 4H), 1.26 (d, J=6.8 Hz, 3H).

Example 33

(6S)-3-[(3S)-3-hydroxypyrrolidin-1-yl]sulfonyl-6-methyl-N-(3,4,5-trifluorophenyl)-6,7-dihydro-4H-pyrazolo[1,5-a]pyrazine-5-carboxamide

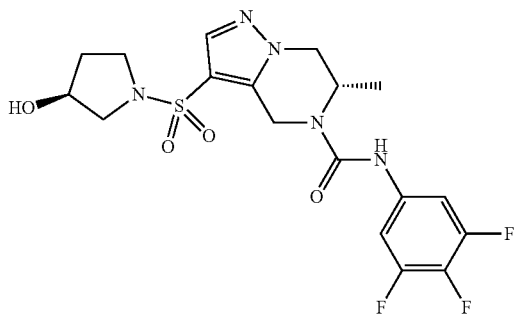 [SMILES: C[C@H]1Cn2ncc(S(=O)(=O)N3CC[C@H](O)C3)c2CN1C(=O)Nc1cc(F)c(F)c(F)c1]

Preparation of (6S)-3-[(3S)-3-hydroxypyrrolidin-1-yl]sulfonyl-6-methyl-N-(3,4,5-trifluorophenyl)-6,7-dihydro-4H-pyrazolo[1,5-a]pyrazine-5-carboxamide (Example 33)

The title compound was prepared in analogy to preparation of Example 27 by using (3S)-pyrrolidin-3-ol instead of 2-amino-2-methyl-propan-1-ol. Example 33 (5 mg) was obtained as a white solid. LCMS (M+H⁺): 460. ¹H NMR (400 MHz, METHANOL-d₄) δ ppm 7.86 (s, 1H), 7.29-7.23 (m, 2H), 5.30 (d, J=17.9 Hz, 1H), 4.99-4.90 (m, 1H), 4.63 (d, J=18.1 Hz, 1H), 4.38-4.31 (m, 2H), 4.22 (d, J=12.8 Hz, 1H), 3.42-3.33 (m, 3H), 3.23-3.18 (m, 1H), 2.04-1.92 (m, 1H), 1.88-1.79 (m, 1H), 1.24 (d, J=6.9 Hz, 3H).

Example 34

(6S)-3-(3-hydroxycyclopentyl)sulfonyl-6-methyl-N-(3,4,5-trifluorophenyl)-6,7-dihydro-4H-pyrazolo[1,5-a]pyrazine-5-carboxamide

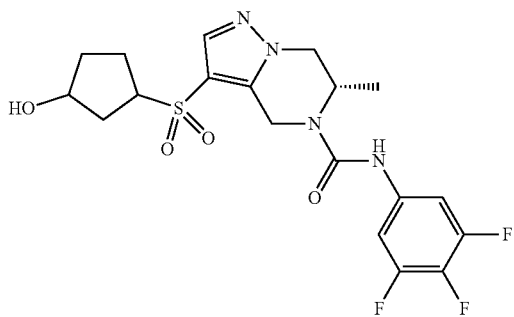 [SMILES: C[C@H]1Cn2ncc(S(=O)(=O)C3CCC(O)C3)c2CN1C(=O)Nc1cc(F)c(F)c(F)c1]

The title compound was prepared according to the following scheme:

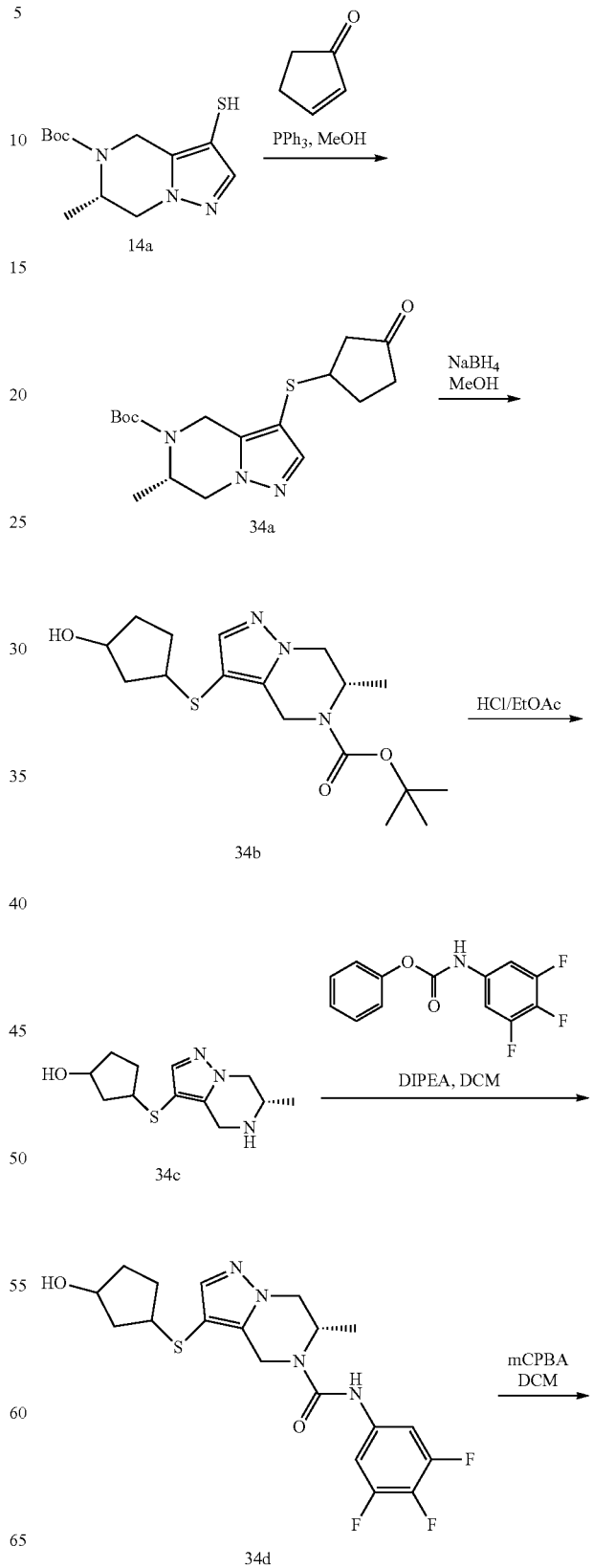

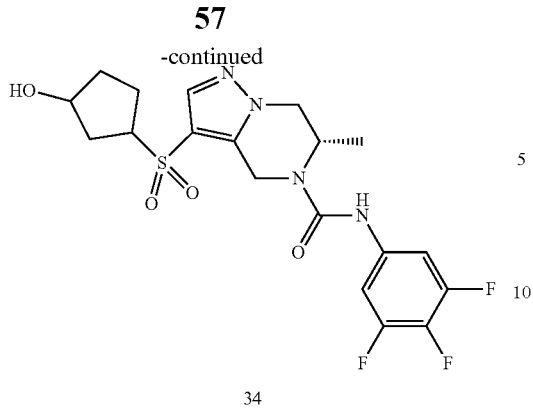

34

Step 1: Preparation of tert-butyl (6S)-6-methyl-3-(3-oxocyclopentyl)sulfanyl-6,7-dihydro-4H-pyrazolo[1,5-a]pyrazine-5-carboxylate (compound 34a)

To the mixture of tert-butyl (6S)-6-methyl-3-sulfanyl-6,7-dihydro-4H-pyrazolo[1,5-a]pyrazine-5-carboxylate (compound 14a, 200.0 mg, 0.37 mmol) and cyclopent-2-en-1-one (61.2 mg, 0.74 mmol) in MeOH (5.0 mL) was added PPh$_3$ (195.5 mg, 0.74 mmol) at room temperature. After stirred at room temperature for 16 hours, the reaction solvent was removed under reduced pressure. The residue was purified by prep-HPLC to give compound 34a (55.0 mg) as a gray solid. LCMS (M+H$^+$): 352.

Step 2: Preparation of tert-butyl (6S)-3-(3-hydroxycyclopentyl)sulfanyl-6-methyl-6,7-dihydro-4H-pyrazolo[1,5-a]pyrazine-5-carboxylate (compound 34b)

To a solution of tert-butyl (6S)-6-methyl-3-(3-oxocyclopentyl)sulfanyl-6,7-dihydro-4H-pyrazolo[1,5-a]pyrazine-5-carboxylate (compound 34a, 55.0 mg, 0.156 mmol) in MeOH (5.0 mL) was added NaBH$_4$ (5.8 mg, 0.156 mmol) at 0° C. The reaction mixture was warmed to room temperature and stirred for 2 hours. Then solvent was removed under reduced pressure and the residue was purified by prep-HPLC to give compound 34b (35.0 mg) as a white solid. LCMS (M+H$^+$): 354.

Step 3: Preparation of 3-[[(6S)-6-methyl-4,5,6,7-tetrahydropyrazolo[1,5-a]pyrazin-3-yl]sulfanyl]cyclopentanol (compound 34c)

To a solution of tert-butyl (6S)-3-(3-hydroxycyclopentyl)sulfanyl-6-methyl-6,7-dihydro-4H-pyrazolo[1,5-a]pyrazine-5-carboxylate (compound 34b, 35.0 mg, 0.10 mmol) in EtOAc (5.0 mL) was added HCl/EtOAc (4 M, 5.0 mL). The reaction mixture was stirred at room temperature for 2 hours, then solvent was removed under reduced pressure to give crude compound 34c (30.0 mg, crude) as a white solid. LCMS (M+H$^+$): 254.

Step 4: Preparation of (6S)-3-(3-hydroxycyclopentyl)sulfanyl-6-methyl-N-(3,4,5-trifluorophenyl)-6,7-dihydro-4H-pyrazolo[1,5-a]pyrazine-5-carboxamide (compound 34d)

To a solution of 3-[[(6S)-6-methyl-4,5,6,7-tetrahydropyrazolo[1,5-a]pyrazin-3-yl]sulfanyl]cyclopentanol (compound 34c, 30.0 mg, 0.118 mmol) in DMF (5.0 mL) was added DIPEA (30.6 mg, 0.237 mmol) and phenyl N-(3,4,5-trifluorophenyl)carbamate (31.6 mg, 0.118 mol). The reaction mixture was stirred at 120° C. for 2 hours, then concentrated to give a crude product which was purified by prep-TLC to give compound 34d (30.0 mg) as a yellow solid. LCMS (M+H$^+$): 427.

Step 5: Preparation of (6S)-3-(3-hydroxycyclopentyl)sulfonyl-6-methyl-N-(3,4,5-trifluorophenyl)-6,7-dihydro-4H-pyrazolo[1,5-a]pyrazine-5-carboxamide (Example 34)

To a solution of (6S)-3-(3-hydroxycyclopentyl)sulfanyl-6-methyl-N-(3,4,5-trifluorophenyl)-6,7-dihydro-4H-pyrazolo[1,5-a]pyrazine-5-carboxamide (compound 34d, 30.0 mg, 0.070 mmol) in DCM (5.0 mL) was added mCPBA (24.3 mg, 0.141 mol). The reaction mixture was stirred at room temperature for 2 hours, then solvent was removed under reduced pressure. The residue was purified by prep-HPLC to give Example 34 (9.0 mg) as a yellow solid. LCMS (M+H$^+$): 459. $^1$H NMR (400 MHz, CHLOROFORM-d) δ ppm 7.90 (s, 1H), 7.29-7.24 (m, 2H), 5.32 (d, J=24.0 Hz, 1H), 4.98-4.94 (m, 1H), 4.65 (d, J=24.0 Hz, 1H), 4.39-4.38 (m, 1H), 4.40-4.30 (m, 1H), 4.26-4.15 (m, 2H), 3.75-3.67 (m, 1H), 2.25-2.11 (m, 2H), 1.95-1.84 (m, 3H), 1.89-1.84 (m, 1H), 1.25 (d, J=9.2 Hz, 3H).

Example 35

3-acetamido-N-(3-chloro-4-fluoro-phenyl)-6,7-dihydro-4H-pyrazolo[1,5-a]pyrazine-5-carboxamide

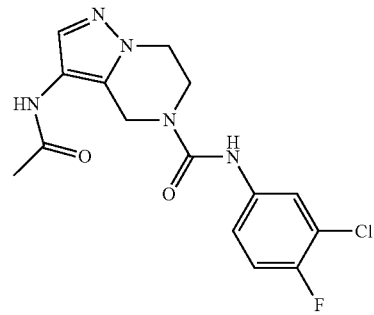 [SMILES: CC(=O)Nc1cnn2c1CN(C(=O)Nc1ccc(F)c(Cl)c1)CC2]

The title compound was prepared according to the following scheme:

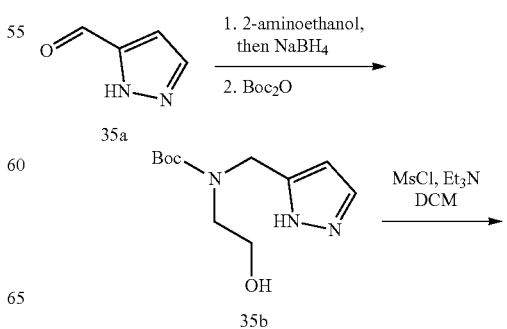

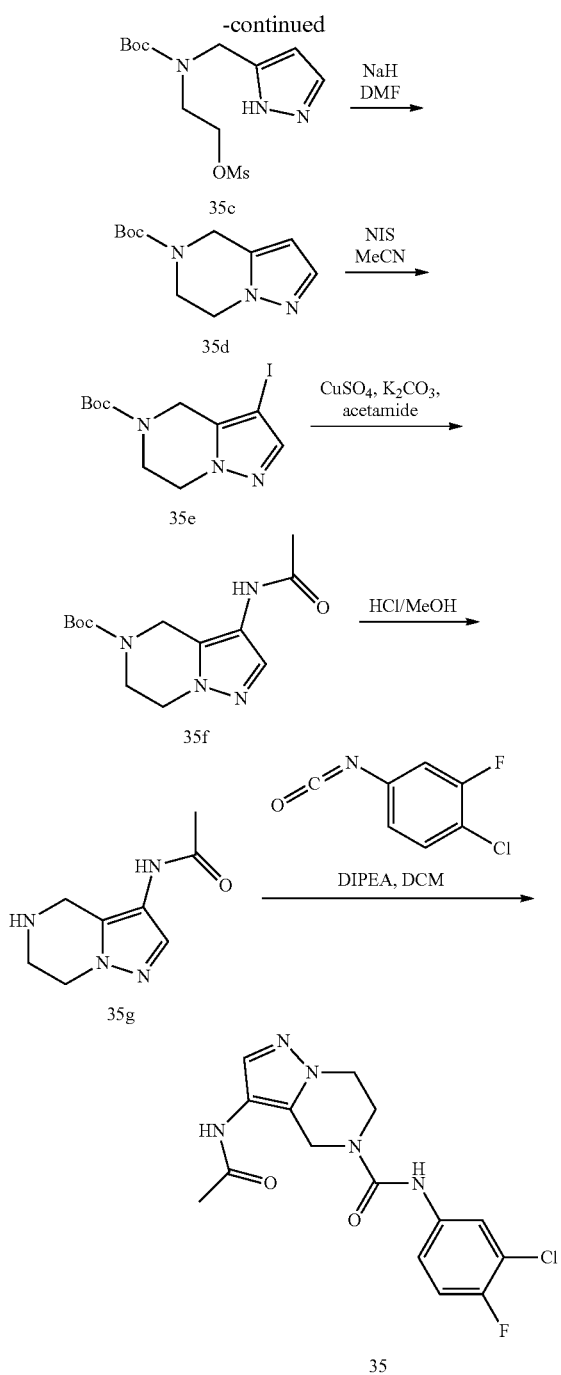

Step 1: Preparation of tert-butyl N-(2-hydroxyethyl)-N-(1H-pyrazol-5-ylmethyl)carbamate (compound 35b)

To a solution of 1H-pyrazole-5-carbaldehyde (compound 35a, 54.0 g, 562.5 mmol) in MeOH (300 mL) was added 2-aminoethanol (41.2 g, 675 mmol), and the reaction mixture was stirred at room temperature for 1 hour. NaBH₄ (25.9 g, 675.0 mmol) was then added at 0° C. and the reaction mixture was stirred for another hour. H₂O (300 mL) and Boc₂O (147.1 g, 675.0 mmol) were added to the reaction mixture, then the resulting mixture was stirred at room temperature for 12 hours, and extracted with EtOAc (600 mL). The organic layer was dried over Na₂SO₄, filtered and concentrated. The residue was purified by column chromatography (eluting with 20%~50% EtOAc in petroleum ether) to afford compound 35b (80 g) as a colorless oil.

Step 2: Preparation of 2-[tert-butoxycarbonyl(1H-pyrazol-5-ylmethyl)amino]ethyl methanesulfonate (compound 35c)

To a solution of tert-butyl N-(2-hydroxyethyl)-N-(1H-pyrazol-5-ylmethyl)carbamate (compound 35b, 80.0 g, 117.2 mmol) and Et₃N (100.5 g, 995.6 mmol) in DCM (800 mL) was added MsCl (57.3 g, 497.8 mmol) slowly at 0° C. The resulting mixture was stirred at room temperature for 2 hours, washed with water (500 mL) and brine (500 mL), dried over Na₂SO₄ and concentrated to afford compound 35c (100 g, crude) which was used directly in next step.

Step 3: Preparation of tert-butyl 6,7-dihydro-4H-pyrazolo[1,5-a]pyrazine-5-carboxylate (compound 35d)

To a solution of 2-[tert-butoxycarbonyl(1H-pyrazol-5-ylmethyl)amino]ethyl methanesulfonate (compound 35c, 100.0 g, 313.4 mmol) in DMF (1 L) was added NaH (15.0 g, 376.2 mmol) in portions at 0° C. The resulting reaction mixture was stirred at room temperature for 12 hours, then poured into water (2 L) and extracted with EtOAc (1 L) twice. The combined organic layer was dried over Na₂SO₄, and then concentrated to afford compound 35d (18.0 g). LCMS (M+H⁺): 224.

Step 4: Preparation of tert-butyl 3-iodo-6,7-dihydro-4H-pyrazolo[1,5-a]pyrazine-5-carboxylate (compound 35e)

To a solution of tert-butyl 6,7-dihydro-4H-pyrazolo[1,5-a]pyrazine-5-carboxylate (compound 35d, 3.3 g, 14.8 mmol) in CH₃CN (40 mL) was added NIS (5.0 g, 22.1 mmol) slowly. The reaction mixture was stirred at room temperature for 16 hours and then diluted with EtOAc (50 mL), and washed with brine (50 mL). The organic layer was dried over Na₂SO₄ and concentrated. The residue was purified by column chromatography (eluting with 10%~80% EtOAc in petroleum ether) to afford compound 35e (4.8 g) as a white solid. LCMS (M+H⁺): 350. ¹H NMR (400 MHz, chloroform-d) δ ppm 7.53 (s, 1H), 4.53 (br, 2H), 4.20 (t, J=5.27 Hz, 2H), 3.89 (t, J=5.14 Hz, 2H), 1.53 (s, 9H).

Step 5: Preparation of tert-butyl 3-acetamido-6,7-dihydro-4H-pyrazolo[1,5-a]pyrazine-5-carboxylate (compound 35f)

To a solution of tert-butyl 3-iodo-6,7-dihydro-4H-pyrazolo[1,5-a]pyrazine-5-carboxylate (compound 35e, 349.1 mg, 1.0 mmol) in acetamide (295.0 mg, 5.0 mmol) was added CuSO₄ (191.5 mg, 1.2 mmol) and K₂CO₃ (345.5 mg, 2.5 mmol) at room temperature. The reaction mixture was stirred at 130° C. for 5 hours, then diluted with DCM (100.0 mL) and filtered. The filtrate was concentrated, and the residue was purified by prep-HPLC to afford compound 35f (14.0 mg) as a yellow solid. LCMS (M+H⁺): 281.

Step 6: Preparation of N-(4,5,6,7-tetrahydropyrazolo[1,5-a]pyrazin-3-yl)acetamide (compound 35g)

To a solution of tert-Butyl 3-acetamido-6,7-dihydro-4H-pyrazolo[1,5-a]pyrazine-5-carboxylate (compound 35f, 14.0 mg, 0.05 mmol) in EtOAc (5.0 mL) was added HCl/EA (5.0 ml). The reaction mixture was stirred at room temperature for 1 hour, then solvent was removed under reduced pressure to give crude compound 35g (10.8 mg) as a white solid. LCMS (M+H⁺): 181.

Step 7: Preparation of 3-acetamido-N-(3-chloro-4-fluoro-phenyl)-6,7-dihydro-4H-pyrazolo[1,5-a]pyrazine-5-carboxamide (Example 35)

To a solution of N-(4,5,6,7-tetrahydropyrazolo[1,5-a] pyrazin-3-yl)acetamide (compound 35g, 10.8 mg, 0.05 mmol) in DCM (2.0 ml) was added DIPEA (13.0 mg, 0.1 mmol) and 1-chloro-2-fluoro-4-isocyanato-benzene (8.5 mg, 0.05 mmol) at 0° C. The reaction mixture was stirred at room temperature for 1 hour, then solvent was removed under reduced pressure. The residue was purified by prep-HPLC to afford Example 35 (6.0 mg) as a white solid. LCMS (M+H⁺): 352. ¹H NMR (300 MHz, DMSO-d₆) δ ppm 9.59 (s, 1H), 9.09 (s, 1H), 7.80-7.67 (m, 1H), 7.52 (s, 1H), 7.48-7.39 (m, 1H), 7.36-7.26 (m, 1H), 4.63 (s, 2H), 4.14-4.09 (m, 2H), 3.93-3.85 (m, 2H), 1.98 (s, 3H).

Example 36

N-(3-chloro-4-fluoro-phenyl)-3-(cyclopentanecarbonylamino)-6,7-dihydro-4H-pyrazolo[1,5-a]pyrazine-5-carboxamide

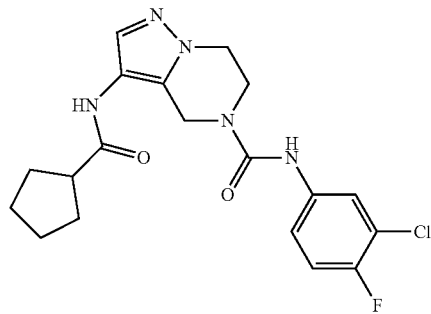 [SMILES: O=C(Nc1cnn2c1CN(C(=O)Nc1ccc(F)c(Cl)c1)CC2)C1CCCC1]

The title compound is prepared according to the following scheme:

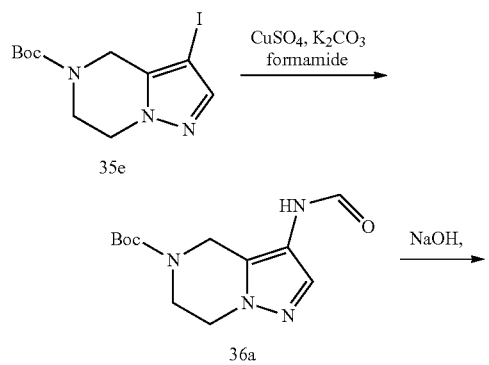

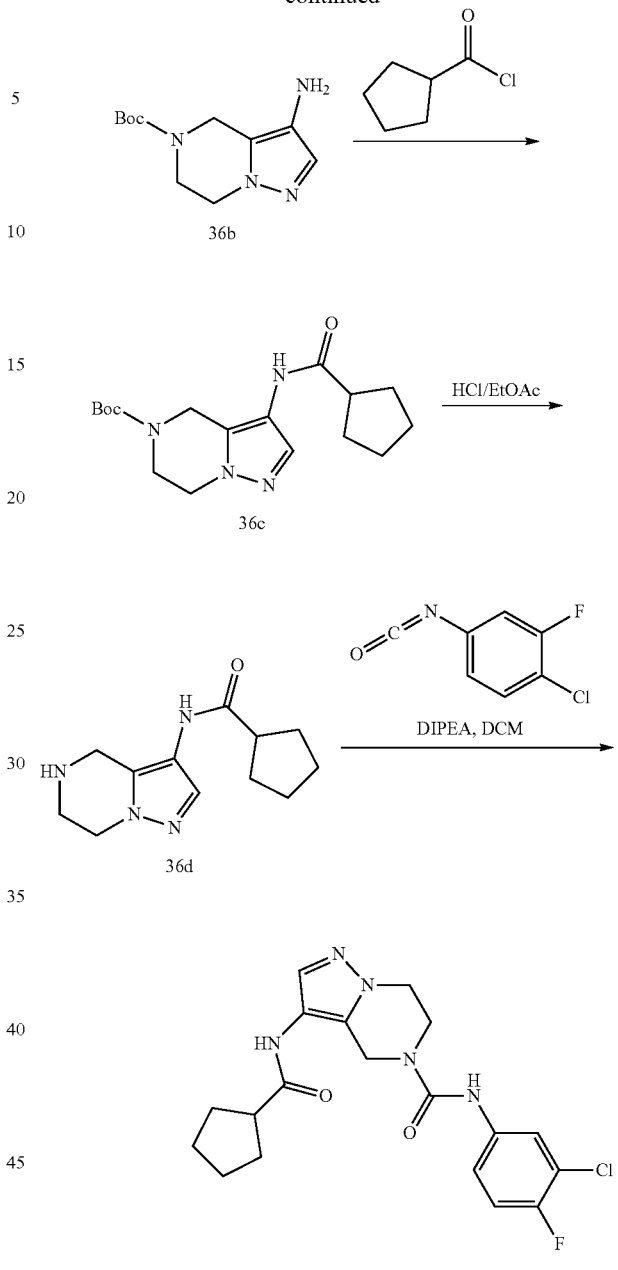

Step 1: Preparation of tert-butyl 3-formamido-6,7-dihydro-4H-pyrazolo[1,5-a]pyrazine-5-carboxylate (compound 36a)

To a solution of tert-butyl 3-iodo-6,7-dihydro-4H-pyrazolo[1,5-a]pyrazine-5-carboxylate (compound 35e, 1.0 g, 2.86 mmol) in formamide (643.5 mg, 14.3 mmol) was added CuSO₄ (547.4 mg, 3.43 mmol) and K₂CO₃ (986.7 mg, 7.15 mmol) at room temperature. The reaction mixture was stirred at 130° C. for 5 hours. After cooling, ice cold water (30.0 mL) was added. The resulting mixture was extracted with DCM (20.0 mL) three times, the combined organic layer was dried over anhydrous sodium sulfate and concentrated to give compound 36a (1.1 g, crude) which was used directly in next step. LCMS (M+H⁺): 267.

Step 2: Preparation of tert-butyl 3-amino-6,7-dihydro-4H-pyrazolo[1,5-a]pyrazine-5-carboxylate (compound 36b)

To a solution of tert-butyl 3-formamido-6,7-dihydro-4H-pyrazolo[1,5-a]pyrazine-5-carboxylate (compound 36a, 1.1 g, crude) in EtOH (5.0 ml) was added NaOH (820.0 mg, 20.5 mmol) in H$_2$O (2.0 mL) at room temperature. The reaction mixture was stirred at 100° C. for 3 hours. After cooling, ice cold water (30 mL) was added, the resulting mixture was extracted with DCM (20.0 mL) three times, the combined organic layer was dried over anhydrous sodium sulfate and concentrated to give a crude product which was purified by prep-HPLC to afford compound 36b (20.0 mg) as a brown solid. LCMS (M+H$^+$): 239.

Step 3: Preparation of tert-butyl 3-(cyclopentanecarbonylamino)-6,7-dihydro-4H-pyrazolo[1,5-a]pyrazine-5-carboxylate (compound 36c)

To a solution of tert-butyl 3-amino-6,7-dihydro-4H-pyrazolo[1,5-a]pyrazine-5-carboxylate (compound 36b, 20.0 mg, 0.084 mmol) and DIPEA (32.5 mg, 0.252 mmol) in DCM (4.0 mL) was added cyclopentanecarbonyl chloride (13.2 mg, 0.1 mmol) at 0° C. The reaction mixture was stirred at room temperature for 2 hours, then solvent was removed and the residue was purified by prep-HPLC to afford compound 36c (15.0 mg) as a white solid. LCMS (M+H$^+$): 335

Step 4: Preparation of N-(4,5,6,7-tetrahydropyrazolo[1,5-a]pyrazin-3-yl)cyclopentanecarboxamide (compound 36d)

To a solution of HCl/EA (4 M, 5.0 ml) was added tert-butyl 3-(cyclopentanecarbonylamino)-6,7-dihydro-4H-pyrazolo[1,5-a]pyrazine-5-carboxylate (compound 36c, 15.0 mg, 0.045 mmol). The reaction mixture was stirred at room temperature for 1 hour, then solvent was removed to afford compound 36d (12.2 mg, crude) as a white solid. LCMS (M+H$^+$): 235.

Step 5: Preparation of N-(3-chloro-4-fluoro-phenyl)-3-(cyclopentanecarbonylamino)-6,7-dihydro-4H-pyrazolo[1,5-a]pyrazine-5-carboxamide (Example 36)

To a solution of N-(4,5,6,7-tetrahydropyrazolo[1,5-a]pyrazin-3-yl)cyclopentanecarboxamide (compound 36d, 12.0 mg, 0.044 mmol) in DCM (3.0 mL) was added DIPEA (17.0 mg, 0.132 mmol) and 1-chloro-2-fluoro-4-isocyanatobenzene (8.2 mg, 0.048 mmol) at room temperature. The reaction mixture was stirred at room temperature for 30 min, then concentrated to give a crude product which was purified by prep-TLC (DCM:MeOH=10:1) to afford Example 36 (15.0 mg) as a white solid. LCMS (M+H$^+$): 406. $^1$H NMR (400 MHz, DMSO-d$_6$) δ ppm 9.55 (s, 1H), 9.15 (s, 1H), 7.81-7.73 (m, 1H), 7.56 (s, 1H), 7.48-7.42 (m, 1H), 7.36-7.27 (m, 1H), 4.64 (s, 2H), 4.14-4.11 (m, 2H), 3.97-3.94 (m, 2H), 2.81-2.72 (m, 1H), 1.88-1.78 (m, 2H), 1.73-1.64 (m, 4H), 1.59-1.51 (m, 2H).

Example 37

Benzyl N-methyl-N-[(6S)-6-methyl-5-[(3,4,5-trifluorophenyl)carbamoyl]-6,7-dihydro-4H-pyrazolo[1,5-a]pyrazin-3-yl]carbamate

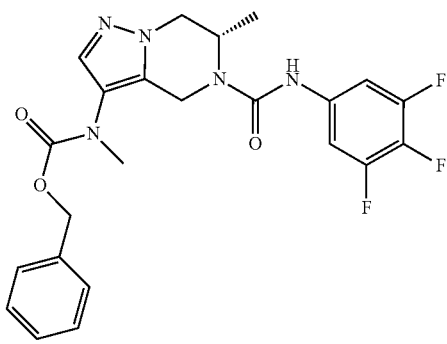 [SMILES: C[C@H]1Cn2ncc(N(C)C(=O)OCc3ccccc3)c2CN1C(=O)Nc1cc(F)c(F)c(F)c1]

The title compound was prepared according to the following scheme:

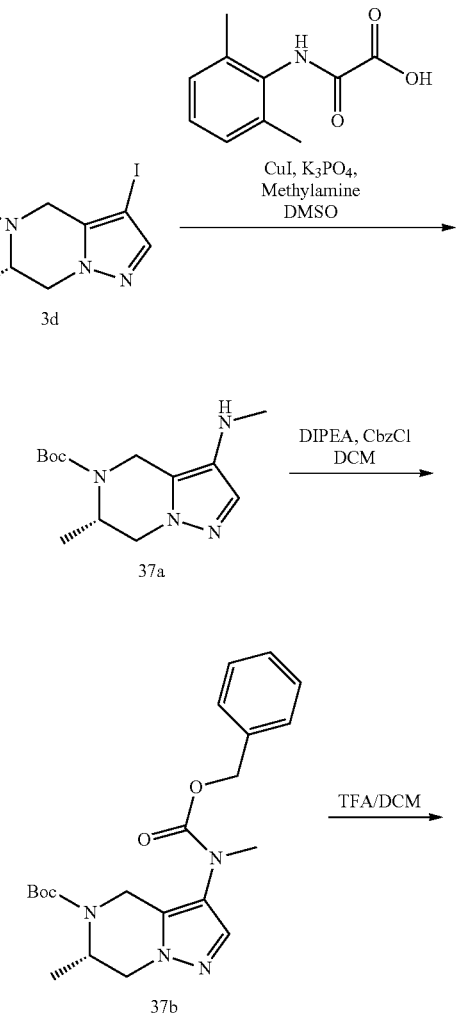

-continued

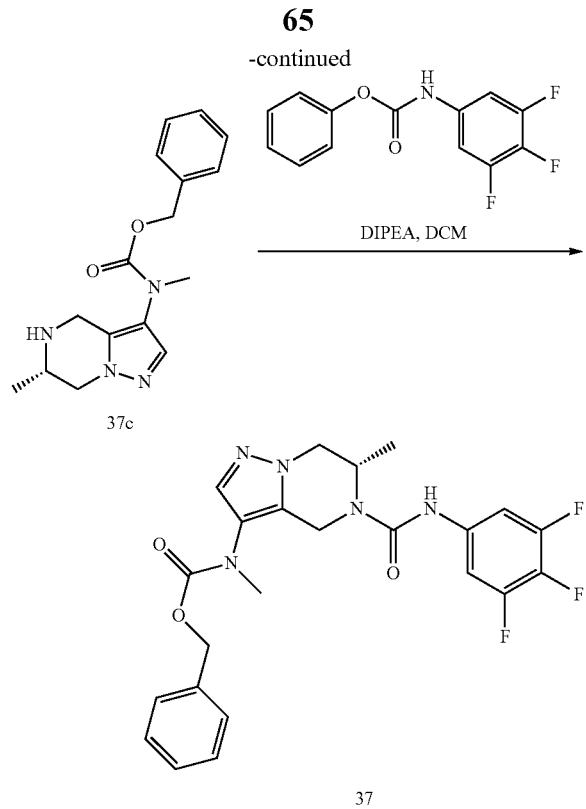

Step 1: Preparation of tert-butyl (6S)-6-methyl-3-(methylamino)-6,7-dihydro-4H-pyrazolo[1,5-a]pyrazine-5-carboxylate (compound 37a)

To a mixture of tert-butyl (6S)-3-iodo-6-methyl-6,7-dihydro-4H-pyrazolo[1,5-a]pyrazine-5-carboxylate (300 mg, 826 µmol), $K_3PO_4$ (351 mg, 1.65 mmol), CuI (31.5 mg, 165 µmol) and 2-((2,6-dimethylphenyl)amino)-2-oxoacetic acid (63.8 mg, 330 µmol) in DMSO (5.0 mL) was added methylamine solution (2M in THF, 1.6 mL). The reaction mixture was flushed with nitrogen, sealed and stirred at 120° C. for 2 hours. Another portion of methylamine (2M THF solution, 0.8 mL) solution was added and the reaction mixture was stirred at 120° C. for another hour. The reaction mixture was then diluted with EtOAc, washed with water and brine, dried over sodium sulfate, concentrated to give compound 37a (210 mg, crude) as a yellow oil which was used directly in next step. LCMS (M+H$^+$): 267.

Step 2: Preparation of tert-butyl (6S)-3-[benzyloxycarbonyl(methyl)amino]-6-methyl-6,7-dihydro-4H-pyrazolo[1,5-a]pyrazine-5-carboxylate (compound 37b)

To a solution of tert-butyl (6S)-6-methyl-3-(methylamino)-6,7-dihydro-4H-pyrazolo[1,5-a]pyrazine-5-carboxylate (compound 37a, 160 mg, crude) and DMAP (220 mg, 1.8 mmol) in DCM (10 mL) was added benzylchloroformate (205 mg, 1.2 mmol) at 0° C. After being stirred at room temperature for 30 min, the reaction was quenched with sat. NH$_4$Cl, then diluted with EtOAc. The organic layer was washed with 1N HCl and brine, dried over sodium sulfate and concentrated to give compound 37b (230 mg, crude) which was used directly in next step. LCMS (M+H$^+$): 401.

Step 3: Preparation of benzyl N-methyl-N-[(6S)-6-methyl-4,5,6,7-tetrahydropyrazolo[1,5-a]pyrazin-3-yl]carbamate (compound 37c)

To a solution of tert-butyl (6S)-3-[benzyloxycarbonyl(methyl)amino]-6-methyl-6,7-dihydro-4H-pyrazolo[1,5-a]pyrazine-5-carboxylate (compound 37b, 230 mg, crude) in DCM (8.0 mL) was added TFA (2.0 mL) dropwise at 0° C. The reaction mixture was stirred at room temperature for 1 hour, then solvent was removed under reduced pressure. The residue was further dried under reduced pressure to give compound 37c (300 mg, crude) as a brown oil. LCMS (M+H$^+$): 301.

Step 4: Preparation of benzyl N-methyl-N-[(6S)-6-methyl-5-[(3,4,5-trifluorophenyl)carbamoyl]-6,7-dihydro-4H-pyrazolo[1,5-a]pyrazin-3-yl]carbamate (Example 37)

To a solution of benzyl N-methyl-N-[(6S)-6-methyl-4,5,6,7-tetrahydropyrazolo[1,5-a]pyrazin-3-yl]carbamate (compound 37c, 300 mg, crude) in DCM (10 m) was added DIPEA (0.74 mL, 4.1 mmol) and phenyl (3,4,5-trifluorophenyl)carbamate (241 mg, 0.90 mmol). The reaction mixture was heated and stirred at 45° C. for 3 hours, then solvent was removed to give the crude product which was purified by prep-HPLC to afford Example 37 (100 mg) as a light yellow powder. LCMS (M+H$^+$): 474. $^1$H NMR (400 MHz, METHANOL-d$_4$) δ ppm 7.52-7.39 (m, 1H), 7.37-7.06 (m, 7H), 5.22-5.02 (m, 1H), 4.96-4.78 (m, 2H), 4.72-4.63 (m, 1H), 4.39-3.86 (m, 3H), 3.15 (s, 3H), 1.15 (d, J=5.3 Hz, 1H), 0.86 (d, J=5.3 Hz, 2H).

Example 38

(6S)-3-[acetyl(methyl)amino]-6-methyl-N-(3,4,5-trifluorophenyl)-6,7-dihydro-4H-pyrazolo[1,5-a]pyrazine-5-carboxamide

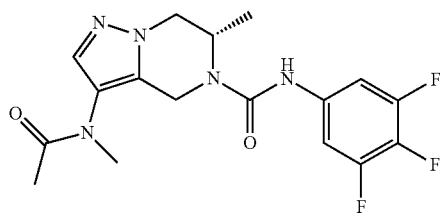 [SMILES: CC(=O)N(C)c1cnn2c1CN(C(=O)Nc1cc(F)c(F)c(F)c1)[C@@H](C)C2]

Preparation of (6S)-3-[acetyl(methyl)amino]-6-methyl-N-(3,4,5-trifluorophenyl)-6,7-dihydro-4H-pyrazolo[1,5-a]pyrazine-5-carboxamide (Example 38)

The title compound was prepared in analogy to Example 37 by using acetyl chloride instead of benzylchloroformate. Example 38 (67 mg) was obtained as a white solid. LCMS (M+1): 382. $^1$H NMR (400 MHz, METHANOL-d$_4$) δ ppm 7.60 (s, 1H), 7.31 (dd, J=6.4, 10.3 Hz, 2H), 5.03 (m, 1H), 5.02 (d, J=16.6 Hz, 1H), 4.48 (d, J=16.6 Hz, 1H), 4.39-4.27 (m, 1H), 4.23-4.11 (m, 1H), 3.21 (s, 3H), 1.95 (s, 3H), 1.24 (d, J=6.8 Hz, 3H).

Example 39

(6S)-3-[2-methoxyethylsulfonyl(methyl)amino]-6-methyl-N-(3,4,5-trifluorophenyl)-6,7-dihydro-4H-pyrazolo[1,5-a]pyrazine-5-carboxamide

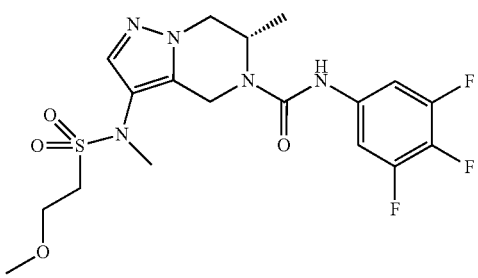 [SMILES: COCCS(=O)(=O)N(C)c1cnn2c1CN(C(=O)Nc1cc(F)c(F)c(F)c1)[C@@H](C)C2]

The title compound was prepared according to the following scheme:

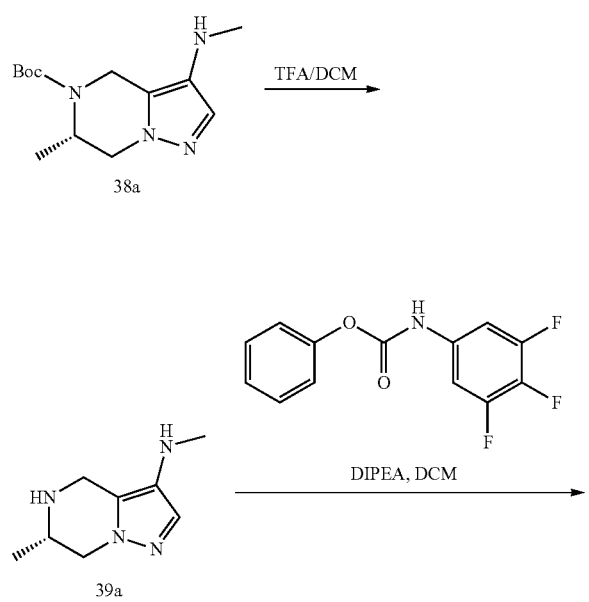

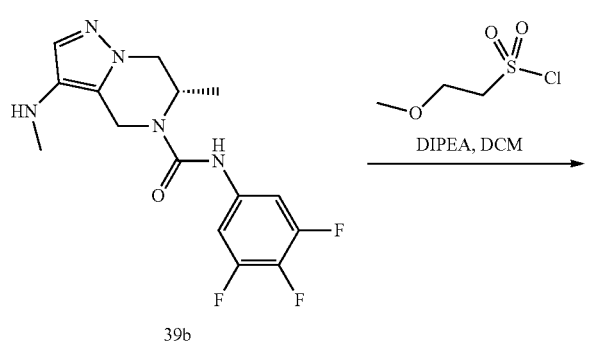

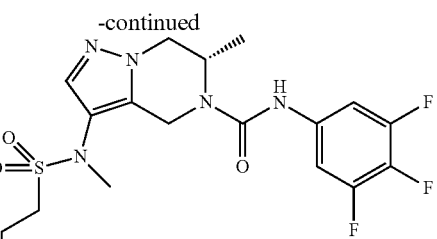

39

Step 1: Preparation of (6S)-N,6-dimethyl-4,5,6,7-tetrahydropyrazolo[1,5-a]pyrazin-3-amine (compound 39a)

To a solution of (S)-tert-butyl 6-methyl-3-(methylamino)-6,7-dihydropyrazolo[1,5-a]pyrazine-5(4H)-carboxylate (compound 38a, 1.8 g, 6.76 mmol) in DCM (30 mL) was added TFA (10 mL) at room temperature. The reaction mixture was stirred at room temperature for 2 hours, then solvent was removed and the residue was further dried under reduced pressure to give crude compound 39a (2.3 g, crude) as a brown oil which was used directly in next step. LCMS (M+H$^+$): 167.

Step 2: Preparation of (6S)-6-methyl-3-(methylamino)-N-(3,4,5-trifluorophenyl)-6,7-dihydro-4H-pyrazolo[1,5-a]pyrazine-5-carboxamide (compound 39b)

To a solution of (6S)-N,6-dimethyl-4,5,6,7-tetrahydropyrazolo[1,5-a]pyrazin-3-amine (compound 39a, 2.3 g, crude) in DCM (50 ML) and DIPEA (4.37 g, 33.8 mmol) was added phenyl (3,4,5-trifluorophenyl)carbamate (2.71 g, 10.1 mmol) in DCM (10 mL) dropwise. The mixture was stirred at 45° C. for 4 hours, then diluted with EtOAc and washed with sat NH$_4$Cl and brine. The organic layer was dried over Na$_2$SO$_4$ and concentrated to give compound 39b (2.4 g, crude) as a brown oil which was used directly in next step. LCMS (M+H$^+$): 340.

Step 3: Preparation of (6S)-3-[2-methoxyethylsulfonyl(methyl)amino]-6-methyl-N-(3,4,5-trifluorophenyl)-6,7-dihydro-4H-pyrazolo[1,5-a]pyrazine-5-carboxamide (Example 39)

To a solution of (6S)-6-methyl-3-(methylamino)-N-(3,4,5-trifluorophenyl)-6,7-dihydro-4H-pyrazolo[1,5-a]pyrazine-5-carboxamide (compound 39b, 120 mg, crude) and DIPEA (229 mg, 1.77 mmol) in DCM was added 2-methoxyethanesulfonyl chloride (168 mg, 1.06 mmol) at 0° C. The mixture was stirred at room temperature for 2 hours, then quenched with sat NH$_4$Cl, diluted with EtOAc and concentrated to give a crude product which was purified by prep-HPLC to give Example 39 (20 mg) as a white powder. LCMS (M+H$^+$): 462. $^1$H NMR (400 MHz, METHANOL-d4) δ ppm 7.73 (s, 1H), 7.30 (dd, J=6.4, 10.4 Hz, 2H), 5.09 (d, J=17.0 Hz, 1H), 5.03-4.95 (m, 1H), 4.59 (d, J=17.0 Hz, 1H), 4.38-4.19 (m, 1H), 4.15 (d, J=12.1 Hz, 1H), 3.86-3.73 (m, 2H), 3.42 (s, 3H), 3.41-3.35 (m, 2H), 3.27 (s, 3H), 1.23 (d, J=7.0 Hz, 3H).

Example 40

(6S)-3-[ethylsulfonyl(methyl)amino]-6-methyl-N-(3,4,5-trifluorophenyl)-6,7-dihydro-4H-pyrazolo[1,5-a]pyrazine-5-carboxamide

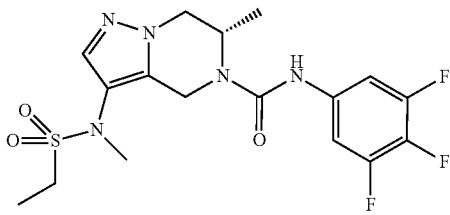 [SMILES: CCS(=O)(=O)N(C)c1cnn2c1CN(C(=O)Nc1cc(F)c(F)c(F)c1)[C@@H](C)C2]

Preparation of (6S)-3-[ethylsulfonyl(methyl)amino]-6-methyl-N-(3,4,5-trifluorophenyl)-6,7-dihydro-4H-pyrazolo[1,5-a]pyrazine-5-carboxamide (Example 40)

The title compound was prepared in analogy to the preparation of Example 39 by using ethanesulfonyl chloride instead of 2-methoxyethanesulfonyl chloride. Example 40 (33 mg) was obtained as a white solid. LCMS (M+H$^+$): 432. $^1$H NMR (400 MHz, METHANOL-$d_4$) δ ppm 7.74 (s, 1H), 7.30 (dd, J=6.3, 10.3 Hz, 2H), 5.09 (d, J=16.9 Hz, 1H), 5.03-4.94 (m, 1H), 4.60 (d, J=17.0 Hz, 1H), 4.29 (dd, J=4.3, 12.7 Hz, 1H), 4.19-4.08 (m, 1H), 3.29 (s, 3H), 3.18 (dq, J=2.9, 7.4 Hz, 2H), 1.38 (t, J=7.4 Hz, 3H), 1.22 (d, J=6.8 Hz, 3H).

Example 41

(6S)-3-[cyclopropylsulfonyl(methyl)amino]-6-methyl-N-(3,4,5-trifluorophenyl)-6,7-dihydro-4H-pyrazolo[1,5-a]pyrazine-5-carboxamide

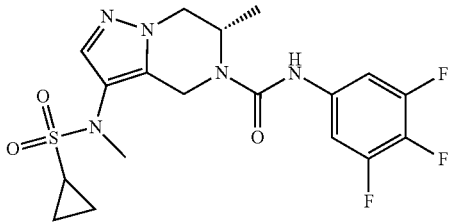 [SMILES: C[C@H]1Cn2ncc(N(C)S(=O)(=O)C3CC3)c2CN1C(=O)Nc1cc(F)c(F)c(F)c1]

Preparation of (6S)-3-[cyclopropylsulfonyl(methyl)amino]-6-methyl-N-(3,4,5-trifluorophenyl)-6,7-dihydro-4H-pyrazolo[1,5-a]pyrazine-5-carboxamide (Example 41)

The title compound was prepared in analogy to the preparation of Example 39 by using cyclopropanesulfonyl chloride instead of 2-methoxyethanesulfonyl chloride. Example 41 (29 mg) was obtained as a white solid. LCMS (M+H$^+$): 444. $^1$H NMR (400 MHz, METHANOL-$d_4$) δ ppm 7.78 (s, 1H), 7.30 (dd, J=6.4, 10.4 Hz, 2H), 5.07 (d, J=16.9 Hz, 1H), 5.03-4.93 (m, 1H), 4.59 (d, J=16.9 Hz, 1H), 4.29 (dd, J=4.3, 12.8 Hz, 1H), 4.20-4.08 (m, 1H), 3.31 (s, 3H), 2.64 (tt, J=5.0, 7.7 Hz, 1H), 1.22 (d, J=6.8 Hz, 3H), 1.13-0.91 (m, 4H).

Example 42

HBV Inhibition Assays

Cell Line and Culture Conditions:

HepG2.2.15 is a stably-transfected cell line containing the HBV genome. It is derived from the hepatoblastoma cell line Hep G2 (American Type Culture Collection, ATCC® HB-8065™) by the published procedures described in reference: M A Selles et al. Proc. Natl. Acad. Sci. USA 1987, 84, 1005-1009. The cell line was maintained in Dulbecco's modified Eagle's medium (DMEM)-F12 medium supplemented with 10% fetal bovine serum, 20 mM L-glutamine, 0.1 mM NEAA, 50 U/mL penicillin, 50 μg/mL streptomycin, and 0.3 mg/mL of G418.

Anti-HBV Activity In Vitro:

HepG2.2.15 cells were seeded into 96-well plates at a density of 3×10$^4$ cells per well in 100 μL DMEM/F12 media (Life Science, Cat. #: 11320-033) supplemented with 2.5% fetal bovine serum, 20 mM L-glutamine, 0.1 mM NEAA, 50 U/mL penicillin, 50 U/mL streptomycin and cultured overnight at 37° C. The test compounds were serially half-log diluted in DMSO, then diluted 100 times in culture media. 100 μL diluted solution of tested compounds were added into the plates to reach 0.5% final concentration of DMSO in every well. Five days after compound treatment, culture supernatant was collected for further analysis.

For quantitative PCR detection of extracellular HBV DNA, culture supernatant was processed by 500 μg/mL Proteinase K (Sigma, Cat. #: P2308) digestion at 50° C. for 1 hour. After heat inactivation of the enzyme at 95° C. for 15 minutes, the samples were subjected to HBV DNA quantification by qPCR. The effective compound concentration at which HBV replication inhibited by 50% (EC$_{50}$) was determined.

The Examples of the present invention were tested in the above assays as described herein and found to have EC$_{50}$ of about 0.008 μM to about 1 μM in HepG2.2.15 assay as shown in Table 1 below.

TABLE 1

| Activity of compounds of this invention in HepG2.2.15 assay | |
|---|---|
| Example No | EC$_{50}$ (μM) |
| 1 | 0.018 |
| 2 | 0.008 |
| 3 | 0.151 |
| 4 | 0.107 |
| 5 | 0.434 |
| 6 | 0.310 |
| 7 | 0.984 |
| 8 | 0.713 |
| 9 | 0.240 |
| 10 | 0.032 |
| 11 | 0.011 |
| 12 | 0.011 |
| 13 | 0.024 |
| 14 | 0.055 |
| 15 | 0.097 |
| 16 | 0.077 |
| 17 | 0.871 |
| 18 | 0.471 |
| 19 | 0.134 |

TABLE 1-continued

| Activity of compounds of this invention in HepG2.2.15 assay | |
|---|---|
| Example No | EC$_{50}$ (µM) |
| 20 | 0.021 |
| 21 | 0.272 |
| 22 | 0.078 |
| 23 | 0.078 |
| 24 | 0.142 |
| 25 | 0.082 |
| 26 | 0.365 |
| 27 | 0.156 |
| 28 | 0.168 |
| 29 | 0.146 |
| 30 | 0.156 |
| 31 | 0.022 |
| 32 | 0.179 |
| 33 | 0.145 |
| 34 | 0.096 |
| 37 | 0.475 |
| 38 | 0.457 |
| 39 | 0.664 |
| 40 | 0.169 |
| 41 | 0.086 |

The invention claimed is:

1. A compound of formula (I),

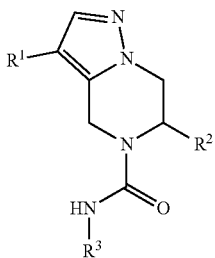

wherein:
R$^1$ is
—OR$^4$, wherein R$^4$ is C$_{1-6}$alkyl, C$_{3-7}$cycloalkyl, tetrahydrofuranyl, tetrahydropyranyl, oxopyrrolidinyl, C$_{1-6}$alkylsulfonylpiperidinyl, pyridinyl, halopyridinyl or pyrimidinyl;
—SO$_2$R$^5$, wherein R$^5$ is C$_{1-6}$alkyl, C$_{3-7}$cycloalkyl, hydroxyC$_{3-7}$cycloalkyl, C$_{1-6}$alkylamino, (C$_{1-6}$alkyl)$_2$amino, hydroxyC$_{1-6}$alkylamino, tetrahydrofuranylamino, pyrrolidinyl, halopyrrolidinyl, hydroxypyrrolidinyl, morpholinyl, haloazetidinyl, tetrahydrofuranyl or tetrahydropyranyl; or
—NR$^6$R$^7$, wherein R$^6$ and R$^7$ are independently selected from H, C$_{1-6}$alkyl, C$_{1-6}$alkylcarbonyl, C$_{3-7}$cycloalkylcarbonyl, benzyloxycarbonyl, C$_{1-6}$alkoxyC$_{1-6}$alkylsulfonyl, C$_{1-6}$alkylsulfonyl and C$_{3-7}$cycloalkylsulfonyl;
R$^2$ is H or C$_{1-6}$alkyl; and
R$^3$ is
phenyl, wherein said phenyl is unsubstituted or substituted once, twice or three times by halogen; or
pyridinyl, wherein said pyridinyl is unsubstituted or substituted by halogen or haloC$_{1-6}$alkyl;
or a pharmaceutically acceptable salt, enantiomer or diastereomer thereof.

2. A compound according to claim 1, wherein:
R$^1$ is isopropoxy, cyclopentoxy, tetrahydrofuranyloxy, tetrahydropyranyloxy, oxopyrrolidinyloxy, methylsulfonylpiperidinyloxy, pyridinyloxy, fluoropyridinyloxy, pyrimidinyloxy, cyclopentylsulfonyl, cyclopropylsulfonyl, difluoroazetidinylsulfonyl, difluoropyrrolidinylsulfonyl, dimethylaminosulfonyl, hydroxycyclopentylsulfonyl, hydroxydimethylethylaminosulfonyl, hydroxypyrrolidinylsulfonyl, isobutylsulfonyl, isopropylsulfonyl, isopropylaminosulfonyl, morpholinylsulfonyl, pyrrolidinylsulfonyl, tetrahydrofuranylsulfonyl, tetrahydrofuranylaminosulfonyl, tetrahydropyranylsulfonyl, acetylamino, acetyl(methyl)amino, cyclopentylcarbonylamino, benzyloxycarbonyl(methyl)amino, methoxyethylsulfonyl(methyl)amino, ethylsulfonyl(methyl)amino or cyclopropylsulfonyl(methyl)amino;
R$^2$ is H or methyl; and
R$^3$ is fluorochlorophenyl, trifluorophenyl, chloropyridinyl or difluoromethylpyridinyl; or a pharmaceutically acceptable salt, enantiomer or diastereomer thereof.

3. A compound according to claim 1, wherein:
R$^1$ is —OR$^4$, wherein R$^4$ is C$_{1-6}$alkyl, C$_{3-7}$cycloalkyl, tetrahydrofuranyl, tetrahydropyranyl, oxopyrrolidinyl, C$_{1-6}$alkylsulfonylpiperidyl, pyridinyl, halopyridinyl or pyrimidinyl;
R$^2$ is C$_{1-6}$alkyl; and
R$^3$ is phenyl, wherein said phenyl is unsubstituted or substituted once, twice or three times by halogen;
or a pharmaceutically acceptable salt, enantiomer or diastereomer thereof.

4. A compound according to claim 3, wherein:
R$^1$ is isopropoxy, cyclopentoxy, tetrahydrofuranyloxy, tetrahydropyranyloxy, oxopyrrolidinyloxy, methylsulfonylpiperidinyloxy, pyridinyloxy, fluoropyridinyloxy or pyrimidinyloxy;
R$^2$ is methyl; and
R$^3$ is fluorochlorophenyl or trifluorophenyl;
or a pharmaceutically acceptable salt, enantiomer or diastereomer thereof.

5. A compound according to claim 3, selected from:
N-(3-chloro-4-fluoro-phenyl)-3-isopropoxy-6-methyl-6,7-dihydro-4H-pyrazolo[1,5-a]pyrazine-5-carboxamide;
N-(3-chloro-4-fluoro-phenyl)-3-(cyclopentoxy)-6-methyl-6,7-dihydro-4H-pyrazolo[1,5-a]pyrazine-5-carboxamide;
(6S)-N-(3-chloro-4-fluoro-phenyl)-6-methyl-3-tetrahydrofuran-3-yloxy-6,7-dihydro-4H-pyrazolo[1,5-a]pyrazine-5-carboxamide;
(6S)-N-(3-chloro-4-fluoro-phenyl)-6-methyl-3-tetrahydropyran-4-yloxy-6,7-dihydro-4H-pyrazolo[1,5-a]pyrazine-5-carboxamide;
(6S)-N-(3-chloro-4-fluoro-phenyl)-6-methyl-3-(2-oxopyrrolidin-3-yl)oxy-6,7-dihydro-4H-pyrazolo[1,5-a]pyrazine-5-carboxamide;
(6S)-N-(3-chloro-4-fluoro-phenyl)-6-methyl-3-[(1-methylsulfonyl-4-piperidyl)oxy]-6,7-dihydro-4H-pyrazolo[1,5-a]pyrazine-5-carboxamide;
(6S)-6-methyl-3-(2-pyridyloxy)-N-(3,4,5-trifluorophenyl)-6,7-dihydro-4H-pyrazolo[1,5-a]pyrazine-5-carboxamide;
(6S)-6-methyl-3-pyrimidin-2-yloxy-N-(3,4,5-trifluorophenyl)-6,7-dihydro-4H-pyrazolo[1,5-a]pyrazine-5-carboxamide; and
(6S)-3-[(5-fluoro-2-pyridyl)oxy]-6-methyl-N-(3,4,5-trifluorophenyl)-6,7-dihydro-4H-pyrazolo[1,5-a]pyrazine-5-carboxamide;

or a pharmaceutically acceptable salt, enantiomer or diastereomer thereof.

6. A compound according to claim 1, wherein:
R$^1$ is —SO$_2$R$^5$, wherein R$^5$ is C$_{1-6}$alkyl, C$_{3-7}$cycloalkyl, hydroxyC$_{3-7}$cycloalkyl, C$_{1-6}$alkylamino, (C$_{1-6}$alkyl)$_2$amino, hydroxyC$_{1-6}$alkylamino, tetrahydrofuranylamino, pyrrolidinyl, halopyrrolidinyl, hydroxypyrrolidinyl, morpholinyl, haloazetidinyl, tetrahydrofuranyl or tetrahydropyranyl;
R$^2$ is C$_{1-6}$alkyl; and R$^3$ is
phenyl, wherein said phenyl is unsubstituted or substituted once, twice or three times by halogen; or
pyridinyl, wherein said pyridinyl is unsubstituted or substituted by halogen or haloC$_{1-6}$alkyl;
or a pharmaceutically acceptable salt, enantiomer or diastereomer thereof.

7. A compound according to claim 6, wherein:
R$^1$ is cyclopentylsulfonyl, cyclopropylsulfonyl, difluoroazetidinylsulfonyl, difluoropyrrolidinylsulfonyl, dimethylaminosulfonyl, hydroxycyclopentylsulfonyl, hydroxydimethylethylaminosulfonyl, hydroxypyrrolidinylsulfonyl, isobutylsulfonyl, isopropylsulfonyl, isopropylaminosulfonyl, morpholinylsulfonyl, pyrrolidinylsulfonyl, tetrahydrofuranylsulfonyl, tetrahydrofuranylaminosulfonyl or tetrahydropyranylsulfonyl;
R$^2$ is methyl; and
R$^3$ is fluorochlorophenyl, trifluorophenyl, chloropyridinyl or difluoromethylpyridinyl; or a pharmaceutically acceptable salt, enantiomer or diastereomer thereof.

8. A compound according to claim 6, selected from:
N-(3-chloro-4-fluoro-phenyl)-6-methyl-3-tetrahydrofuran-3-ylsulfonyl-6,7-dihydro-4H-pyrazolo[1,5-a]pyrazine-5-carboxamide;
N-(3-chloro-4-fluoro-phenyl)-3-cyclopentylsulfonyl-6-methyl-6,7-dihydro-4H-pyrazolo[1,5-a]pyrazine-5-carboxamide;
N-(3-chloro-4-fluoro-phenyl)-3-isopropylsulfonyl-6-methyl-6,7-dihydro-4H-pyrazolo[1,5-a]pyrazine-5-carboxamide;
N-(3-chloro-4-fluoro-phenyl)-3-isobutylsulfonyl-6-methyl-6,7-dihydro-4H-pyrazolo[1,5-a]pyrazine-5-carboxamide;
(6S)-N-(3-chloro-4-fluoro-phenyl)-6-methyl-3-tetrahydrofuran-3-ylsulfonyl-6,7-dihydro-4H-pyrazolo[1,5-a]pyrazine-5-carboxamide;
(6S)-N-(3-chloro-4-fluoro-phenyl)-6-methyl-3-tetrahydropyran-4-ylsulfonyl-6,7-dihydro-4H-pyrazolo[1,5-a]pyrazine-5-carboxamide;
(6S)-6-methyl-3-tetrahydrofuran-3-ylsulfonyl-N-(3,4,5-trifluorophenyl)-6,7-dihydro-4H-pyrazolo[1,5-a]pyrazine-5-carboxamide;
(6S)-N-(2-chloro-4-pyridyl)-6-methyl-3-tetrahydrofuran-3-ylsulfonyl-6,7-dihydro-4H-pyrazolo[1,5-a]pyrazine-5-carboxamide;
(6S)-N-(2-chloro-4-pyridyl)-3-isopropylsulfonyl-6-methyl-6,7-dihydro-4H-pyrazolo[1,5-a]pyrazine-5-carboxamide;
(6S)-N-(2-chloro-4-pyridyl)-3-cyclopentylsulfonyl-6-methyl-6,7-dihydro-4H-pyrazolo[1,5-a]pyrazine-5-carboxamide;
(6S)-3-isopropylsulfonyl-6-methyl-N-(3,4,5-trifluorophenyl)-6,7-dihydro-4H-pyrazolo[1,5-a]pyrazine-5-carboxamide;
(6S)-N-[2-(difluoromethyl)-4-pyridyl]-3-isopropylsulfonyl-6-methyl-6,7-dihydro-4H-pyrazolo[1,5-a]pyrazine-5-carboxamide;
(6S)-3-cyclopropylsulfonyl-6-methyl-N-(3,4,5-trifluorophenyl)-6,7-dihydro-4H-pyrazolo[1,5-a]pyrazine-5-carboxamide;
(6S)-N-(3-chloro-4-fluoro-phenyl)-6-methyl-3-pyrrolidin-1-ylsulfonyl-6,7-dihydro-4H-pyrazolo[1,5-a]pyrazine-5-carboxamide;
(6S)-N-(3-chloro-4-fluoro-phenyl)-3-(dimethylsulfamoyl)-6-methyl-6,7-dihydro-4H-pyrazolo[1,5-a]pyrazine-5-carboxamide;
(6S)-N-(3-chloro-4-fluoro-phenyl)-3-(isopropylsulfamoyl)-6-methyl-6,7-dihydro-4H-pyrazolo[1,5-a]pyrazine-5-carboxamide;
(6S)-N-(3-chloro-4-fluoro-phenyl)-6-methyl-3-[[(3S)-tetrahydrofuran-3-yl]sulfamoyl]-6,7-dihydro-4H-pyrazolo[1,5-a]pyrazine-5-carboxamide;
(6S)-3-[(2-hydroxy-1,1-dimethyl-ethyl)sulfamoyl]-6-methyl-N-(3,4,5-trifluorophenyl)-6,7-dihydro-4H-pyrazolo[1,5-a]pyrazine-5-carboxamide;
(6S)-3-(3,3-difluoropyrrolidin-1-yl)sulfonyl-6-methyl-N-(3,4,5-trifluorophenyl)-6,7-dihydro-4H-pyrazolo[1,5-a]pyrazine-5-carboxamide;
(6S)-3-[(3R)-3-hydroxypyrrolidin-1-yl]sulfonyl-6-methyl-N-(3,4,5-trifluorophenyl)-6,7-dihydro-4H-pyrazolo[1,5-a]pyrazine-5-carboxamide;
(6S)-6-methyl-3-[[(3R)-tetrahydrofuran-3-yl]sulfamoyl]-N-(3,4,5-trifluorophenyl)-6,7-dihydro-4H-pyrazolo[1,5-a]pyrazine-5-carboxamide;
(6S)-3-(3,3-difluoroazetidin-1-yl)sulfonyl-6-methyl-N-(3,4,5-trifluorophenyl)-6,7-dihydro-4H-pyrazolo[1,5-a]pyrazine-5-carboxamide;
(6S)-6-methyl-3-morpholinosulfonyl-N-(3,4,5-trifluorophenyl)-6,7-dihydro-4H-pyrazolo[1,5-a]pyrazine-5-carboxamide;
(6S)-3-[(3S)-3-hydroxypyrrolidin-1-yl]sulfonyl-6-methyl-N-(3,4,5-trifluorophenyl)-6,7-dihydro-4H-pyrazolo[1,5-a]pyrazine-5-carboxamide; and
(6S)-3-(3-hydroxycyclopentyl)sulfonyl-6-methyl-N-(3,4,5-trifluorophenyl)-6,7-dihydro-4H-pyrazolo[1,5-a]pyrazine-5-carboxamide;
or a pharmaceutically acceptable salt, enantiomer or diastereomer thereof.

9. A compound according to claim 1, wherein
R$^1$ is —NR$^6$R$^7$, wherein R$^6$ and R$^7$ are independently selected from H, C$_{1-6}$alkyl, C$_{1-6}$alkylcarbonyl, C$_{3-7}$cycloalkylcarbonyl, benzyloxycarbonyl, C$_{1-6}$alkoxyC$_{1-6}$alkylsulfonyl, C$_{1-6}$alkylsulfonyl and C$_{3-7}$cycloalkylsulfonyl;
R$^2$ is H or C$_{1-6}$alkyl; and
R$^3$ is phenyl, wherein said phenyl is unsubstituted or substituted once, twice or three times by halogen;
or a pharmaceutically acceptable salt, enantiomer or diastereomer thereof.

10. A compound according to claim 6, wherein:
R$^1$ is acetylamino, acetyl(methyl)amino, cyclopentylcarbonylamino, benzyloxycarbonyl(methyl)amino, methoxyethylsulfonyl(methyl)amino, ethylsulfonyl(methyl)amino or cyclopropylsulfonyl(methyl)amino;
R$^2$ is H or methyl; and
R$^3$ is fluorochlorophenyl or trifluorophenyl;
or a pharmaceutically acceptable salt, enantiomer or diastereomer thereof.

11. A compound according to claim 9, selected from:
3-acetamido-N-(3-chloro-4-fluoro-phenyl)-6,7-dihydro-4H-pyrazolo[1,5-a]pyrazine-5-carboxamide;
N-(3-chloro-4-fluoro-phenyl)-3-(cyclopentanecarbonylamino)-6,7-dihydro-4H-pyrazolo[1,5-a]pyrazine-5-carboxamide;

benzyl N-methyl-N-[(6S)-6-methyl-5-[(3,4,5-trifluorophenyl)carbamoyl]-6,7-dihydro-4H-pyrazolo[1,5-a]pyrazin-3-yl]carbamate;

(6S)-3-[acetyl(methyl)amino]-6-methyl-N-(3,4,5-trifluorophenyl)-6,7-dihydro-4H-pyrazolo[1,5-a]pyrazine-5-carboxamide;

(6S)-3-[2-methoxyethylsulfonyl(methyl)amino]-6-methyl-N-(3,4,5-trifluorophenyl)-6,7-dihydro-4H-pyrazolo[1,5-a]pyrazine-5-carboxamide;

(6S)-3-[ethylsulfonyl(methyl)amino]-6-methyl-N-(3,4,5-trifluorophenyl)-6,7-dihydro-4H-pyrazolo[1,5-a]pyrazine-5-carboxamide; and (6S)-3-[cyclopropylsulfonyl(methyl)amino]-6-methyl-N-(3,4,5-trifluorophenyl)-6,7-dihydro-4H-pyrazolo[1,5-a]pyrazine-5-carboxamide;

or a pharmaceutically acceptable salt, enantiomer or diastereomer thereof.

12. A process for preparing a compound according to claim 1, or a pharmaceutically acceptable salt, enantiomer or diastereomer thereof, the process comprising any one of the following steps:

a) reacting a compound of formula (V)

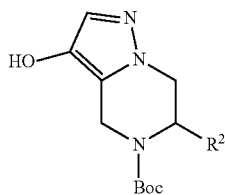

(V)

with an alkyl halide $R^4X$ and an acid followed by urea formation with amine $R^3NH_2$ in the presence of a phosgene equivalent;

b) reacting a compound of formula (VIII)

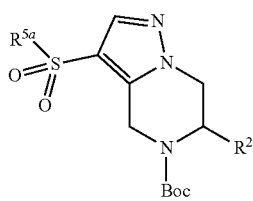

(VIII)

with an acid followed by urea formation with amine $R^3NH_2$ in the presence of a phosgene equivalent;

c) reacting a compound of formula (IX)

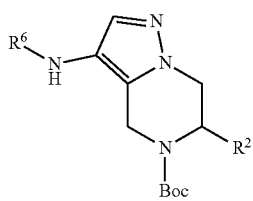

(IX)

with an acid followed by urea formation with amine $R^3NH_2$ in the presence of a phosgene equivalent;

d) reacting a compound of formula (X)

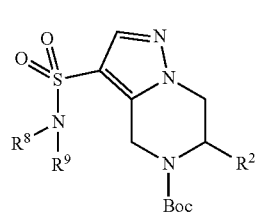

(X)

with an acid followed by urea formation with amine $R^3NH_2$ in the presence of a phosgene equivalent;

e) reacting a compound of formula (XII)

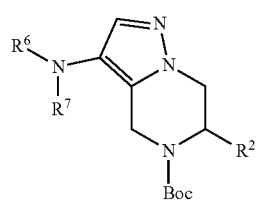

(XII)

with an acid followed by urea formation with amine $R^3NH_2$ in the presence of a phosgene equivalent;

f) reacting a compound of formula (XIII)

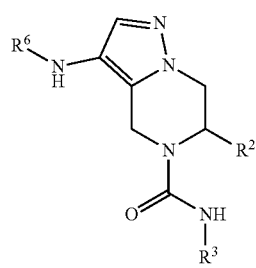

(XIII)

with an acyl chloride or sulfonyl chloride $R^7Cl$;

wherein:

$R^{5a}$ is $C_{1-6}$alkyl, $C_{3-7}$cycloalkyl, hydroxy$C_{3-7}$cycloalkyl, tetrahydrofuranyl or tetrahydropyranyl;

$R^8$ and $R^9$ are independently selected from H, $C_{1-6}$alkyl, tetrahydrofuranyl and hydroxy$C_{1-6}$alkyl, or $R^8$ and $R^9$ together with the nitrogen atom they are attached to form a 3-7 membered heterocyclyl; and X is halogen.

13. A pharmaceutical composition comprising a compound according to claim 1, or a pharmaceutically acceptable salt, enantiomer or diastereomer thereof, and a therapeutically inert carrier.

14. A compound according to claim 1, or a pharmaceutically acceptable salt, enantiomer or diastereomer thereof, when manufactured according to a process comprising any one of the following steps:

a) reacting a compound of formula (V)

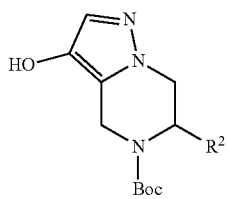

(V)

with an alkyl halide R⁴X and an acid followed by urea formation with amine R³NH₂ in the presence of a phosgene equivalent;

b) reacting a compound of formula (VIII)

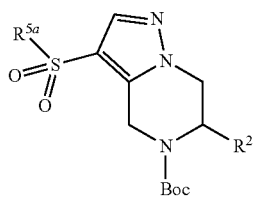

(VIII)

with an acid followed by urea formation with amine R³NH₂ in the presence of a phosgene equivalent;

c) reacting a compound of formula (IX)

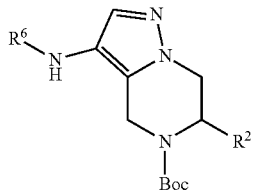

(IX)

with an acid followed by urea formation with amine R³NH₂ in the presence of a phosgene equivalent;

d) reacting a compound of formula (X)

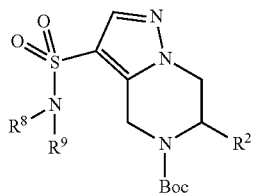

(X)

with an acid followed by urea formation with amine R³NH₂ in the presence of a phosgene equivalent;

e) reacting a compound of formula (XII)

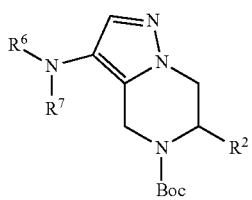

(XII)

with an acid followed by urea formation with amine R³NH₂ in the presence of a phosgene equivalent;

f) reacting a compound of formula (XIII)

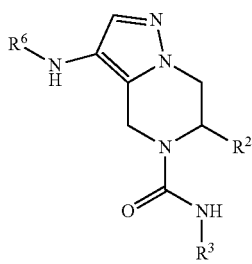

(XIII)

with an acyl chloride or sulfonyl chloride R⁷Cl;

wherein:

$R^{5a}$ is $C_{1-6}$alkyl, $C_{3-7}$cycloalkyl, hydroxy$C_{3-7}$cycloalkyl, tetrahydrofuranyl or tetrahydropyranyl;

$R^8$ and $R^9$ are independently selected from H, $C_{1-6}$alkyl, tetrahydrofuranyl and hydroxy$C_{1-6}$alkyl, or $R^8$ and $R^9$ together with the nitrogen atom they are attached to form a 3-7 membered heterocyclyl; and X is halogen.

15. A method for the treatment of hepatitis B virus infection, which method comprises administering to a patient in need thereof a therapeutically effective amount of a compound according to claim 1, or a pharmaceutically acceptable salt, enantiomer or diastereomer thereof.

* * * * *